(12) United States Patent
Forster et al.

(10) Patent No.: US 6,977,150 B2
(45) Date of Patent: Dec. 20, 2005

(54) PROCESS AND COMPOSITIONS FOR PEPTIDE, PROTEIN AND PEPTIDOMIMETIC SYNTHESIS

(75) Inventors: Anthony C. Forster, 173 Marrett Rd., Lexington, MA (US) 02421; Stephen C. Blacklow, Lincoln, MA (US)

(73) Assignee: Anthony C. Forster, Nashville, TN (US)

( * ) Notice: Subject to any disclaimer, the term of this patent is extended or adjusted under 35 U.S.C. 154(b) by 293 days.

(21) Appl. No.: 10/057,783

(22) Filed: Jan. 25, 2002

(65) Prior Publication Data

US 2004/0091955 A1 May 13, 2004

Related U.S. Application Data

(60) Provisional application No. 60/264,147, filed on Jan. 25, 2001.

(51) Int. Cl.$^7$ .............................. C12Q 1/68; C12P 21/00
(52) U.S. Cl. ......................... 435/6; 435/70.1; 435/69.1; 536/23.1; 530/300
(58) Field of Search .......................... 435/6, 70.1, 69.1; 536/23.1; 530/300; 514/2

(56) References Cited

U.S. PATENT DOCUMENTS 5,643,722 A * 7/1997 Rothschild et al. ............ 435/6

FOREIGN PATENT DOCUMENTS

WO   WO 95/11922 A1   5/1995

OTHER PUBLICATIONS

Stada et al., Nucleic Acids Res. 22, 1394–1399 (1994).*
Ganoza et al., Proc. Natl. Acad. Sci. USA 82, 1648–1652 (1985).*
Fahnestock, S. et al., "Synthesis by ribosomes of viral coat protein containing ester linkages", Nature New Biology, vol. 229, pp. 8–10 (1971).
Fahnestock S. et al., "Ribosome–catalyzed polyester formation", SCIENCE, vol. 173, pp. 340–343 (1971).
Baldini, G. et al., Mischarging *Escherichia coli* tRNAPhe with L–4'–[3–(trifluoromethyl)–3H–diazirin–3–yl] phenylalanine, a photoactivatable analogue of phenylalanine, BIOCHEMISTRY, vol. 27, No. 20, pp. 7951–7959 (1988).
Stade, K. et al., "Contacts between the growing peptide chain and the 23S RNA in the 50S ribosomal subunit," Nucleic Acids Res., vol. 22, No. 8, pp. 1394–1399 (1994).
Stade, K. et al., "Mapping the path of the nascent peptide chain through the 23S RNA in the 50S ribosomal subunit", vol. 23, No. 13, pp. 2371–22380 (1995).
Hohsaka, T. et al., "Incorporation of two different nonnatural amino acids independently into a single protein through extension of the genetic code," J. Am. Chem. Soc. 121, No. 51, pp. 12194–12195 (1999).

Hohsaka, T. et al., "Incorporation of nonnatural amino acids into proteins by using various four–base codons in an *Escherichia coli* in vitro translation system," BIOCHEMISTRY 40, No. 37, pp. 11060–11064, (2001).
Shimizu, Y. et al., "Cell–free translation reconstituted with purified components," Nat. Biotechnol. 19, pp. 751–755 (2001).
Needles, M.C. et al., "Generation and screening of an oligonucleotide–encoded synthetic peptide library," Proc. Natl. Acad. Sci. USA, vol. 90, pp. 10700–10704 (1993).
Gartner, Z.J. et al., "The generality of DNA–templated synthesis as a basis for evolving non–natural small molecules," J. Am. Chem. Soc. 123, No. 28, pp. 6961–6963 (2001).
Pavlov M.Y. et al.: "Fast recycling of *Escherichia coli* ribosomes requires both ribosome recycling factor (RRF) and release factor RF3," The EMBO Journal, Oxford University Press, vol. 16, Nr. 13, Page(s) 4134–4141 (1997) XP–001145784.
Murphy E. C. Jr. et al.: "Cell–Free Synthesis of Rauscher Murine Leukemia Virus 'Gag' and 'Gag–Pol' Precursor Polyproteins from Virion 35 S RNA in a mRNA–Dependent Translation System Derived from Mouse Tissue Culture Cells," VIROLOGY, vol. 86, Nr. 2, Page(s) 329–343 (1978) XP009005933.
Cload S. T. et al.: "Development of improved tRNAs for in vitro biosynthesis of proteins containing unnatural amino acids," Chemistry & Biology (London), vol. 3, Nr. 12, Page(s) 1033–1038 (1996) XP009005959.
Karginov A.V. et al.: "Facile characterization of translation initiation via nonsense codon suppression," Nucleic Acids Research, Oxford University Press, vol. 27, Nr. 16, Page(s) 3283–3290 (1999) XP–001145472.
Klubmann S. et al.: "Mirror–image RNA that binds D–adenosine," Nature Biotechnology, vol. 14, Nr. 9, Page(s) 1063, 1112–1115 (1996).
Nolte A. et al.: "Mirror–design of L–oligonucleotide ligands binding to L–arginine," Nature Biotechnology, vol. 14, Page(s) 1116–1119 (1996).
Gold, Larry, "Reflections on mirrors," Nature Biotechnology, vol. 14, Page(s) 1080 (1996).
Williams, K. P. et al.: "Bioactive and nuclease–resistant L–DNA ligand of vasopressin," Proc. Natl. Acad. Sci. USA, vol. 94, Page(s) 11285–11290 (1997).

(Continued)

*Primary Examiner*—Karen Cochrane Carlson
*Assistant Examiner*—Chih-Min Kam
(74) *Attorney, Agent, or Firm*—Fish & Neave IP Ropes & Gray LLP

(57) ABSTRACT

The present invention is a simplified, highly-purified, processive translation system that does not require the addition of translation factors EF-P, W, W2 or rescue. A new translation process offers new, potentially improved, routes to all peptides, proteins and peptidomimetics currently synthesized by alternative routes.

40 Claims, 22 Drawing Sheets

OTHER PUBLICATIONS

Forster, A. C. et al.: "A Simplified Reconstitution of mRNA-Directed Peptide Synthesis: Activity of the Epsilon Enhancer and an Unnatural Amino Acid," Analytical Biochemistry, vol. 297, Page(s) 60–70 (2001).

Cenatiempo, Y. et al.: "In vitro Expression of *Escherichia coli* Ribosomal Protein L10 Gene: Tripeptide Synthesis as a Measure of Functional mRNA," Archives of Biochemistry and Biophysics, vol. 218, Nr. 2, Page(s) 572–578 (1982).

Doi, N. et al.: "STABLE: protein–DNA fusion system for screening of combinatorial protein libraries in vitro," FEBS Letters, vol. 457, Page(s) 227–230 (1999).

Kung, H. et al.: "The mRNA-Directed Synthesis of the α-Peptide of β-Galactosidase, Ribosomal Proteins L12 and L10, and Elongation Factor Tu, Using Purified Translational Factors," Archives of Biochemistry and Biophysics, vol. 187, Nr. 2, Page(s) 457–463 (1978).

Ganoza, M. C. et al.: "Isolation and point of action of a factor from *Escherichia coli* required to reconstruct translation," Proc. Natl. Acad. Sci. USA, vol. 82, Page(s) 1648–1652 (1985).

Ganoza, M. C. et al.: "The ribosome as 'affinity matrix': Efficient purification scheme for translation factors," BIOCHIMIE, vol. 78, Page(s) 51–61 (1996).

Green, R. H. et al.: "Requirements for in vitro Reconstruction of Protein Synthesis," Biochemical and Biophysical Research Communications, vol. 126, Nr. 2, Page(s) 792–798 (1985).

Mattheakis, L. C. et al.: "An in vitro polysome display system for identifying ligands from very large peptide libraries," Proc. Natl. Acad. Sci. USA, vol. 91, Page(s) 9022–9026 (1994).

Nemoto N. et al.: "In vitro virus: Bonding of mRNA bearing puromycin at the 3'-terminal end to the C-terminal end of its encoded protein on the ribosome in vitro," FEBS Letters, vol. 414, Page(s) 405–408 (1997).

Noren, C. J. et al.: "A General Method for Site-Specific Incorporation of Unnatural Amino Acids into Proteins," SCIENCE, vol. 244, Page(s) 182–188 (1989).

Robakis, N. et al.: "Translational control of ribosomal protein L10 synthesis occurs prior to formation of first peptide bond," Proc. Natl. Acad. Sci. USA, vol. 78, Nr. 7, Page(s) 4261–4264 (1981).

Roberts, R. W. et al.: "RNA–peptide fusions for the in vitro selection of peptides and proteins," Proc. Natl. Acad. Sci. USA, vol. 94, Page(s) 12297–12302 (1997).

Rodnina, M. V. et al: "Hydrolysis of GTP by elongation factor G drives tRNA movement on the ribosome," NATURE, vol. 385, Page(s) 37–41 (1997).

* cited by examiner

Fig. 3

```
                      T7 RNA pol. promoter
             5' TAATACGACTCACTATAG 3'
                ||||||||||||||||||
             3' ATTATGCTGAGTGATATCCCAATTGAAATCATTCCTCCATTTTTT TAC TGG TGG CAA CTT AAG G 5
                                  ||||||||||||||||||||||||||||||||||| ||| ||| ||| ||| ||| ||| - |
mRNA MTTV                      5' pppGGGUUAACUUUAGUAAGGAGGUAAAAAAA AUG ACC ACC GUU GAA UUC C 3'
                                                epsilon        S-D       fM   T   T   V mRNA MTV                       5' pppGGGUUAACUUUAGUAAGGAGGUAAAAAAA AUG ACC GUU GAA UUC C 3'
                                                                       fM   T   V mRNA MV                        5' pppGGGUUAACUUUAGUAAGGAGGUAAAAAAA AUG GUU GAA UUC C 3'
                                                                       fM   V mRNA MVT                       5' pppGGGUUAACUUUAGUAAGGAGGUAAAAACAC AUG GUU ACC GAA UUC C 3'
                                                                        fM   V   T mRNA scramble-epsiMVT          5' pppGGGUAUUAUACUGUAAGGAGGUAAAACAC AUG GUU ACC GAA UUC C 3'
                                                                        fM   V   T mRNA ΔepsiMVT                  5' pppGG--------GUAAGGAGGUAAAACAC AUG GUU ACC GAA UUC C 3'
                                                                        fM   V   T mRNA MTKV                      5' pppGGGUUAACUUUAGUAAGGAGGUAAAAACAC AUG ACC AAA GUU GAA UU 3'
                                                                        fM   T   K   V
```

G  G    for             G  C    for             G  A    for

5' A  C  C              5' A  G  C              5' G  U  C
      U                       U                       U

Unnatural amino acid 1      Unnatural amino acid 2      Unnatural amino acid 3
     (was T)                     (was S)                     (was V)
```

Fig. 19 mRNAs for fM(V,T)$_n$

5' pppGGGUUAACUUUAGUAAGGAGGUAAAACACAUG (GUUACCGUGACUGUAGUUGUGACUACCGUAACCGUAGUGACUGUUGUAACUACCGUUGUG)$_n$AAUU 3'
   fM  V  T  V  T  V  V  V  T  T  V  T  V  V  T  T  V  V fM(V,T)$_n$ peptide products

13-mer
fMVTVTVVVTTVTV 21-mer
fMVTVTVVVTTVTVVVTTVV 41-mer
fMVTVTVVVTTVTVVVTTVVTVTVVVTTVTVVVTTVVTVVV 53-mer
fMVTVTVVVTTVTVVVTTVVTVTVVVTTVTVVVTTVVTVTVVVTTVTVVVTTV 61-mer
fMVTVTVVVTTVTVVVTTVVTVTVVVTTVTVVVTTVVTVTVVVTTVTVVVTTVVTVVTTVV 101-mer
fMVTVTVVVTTVTVVVTTVVTVTVVVTTVTVVVTTVVTVTVVVTTVTVVVTTVVTVTVVVTTVTVVVTTVVTVTVVVTTVTVVVTTVVTVTVVVTTVTVVV

PROCESS AND COMPOSITIONS FOR PEPTIDE, PROTEIN AND PEPTIDOMIMETIC SYNTHESIS

REFERENCE TO RELATED APPLICATIONS

This application claims priority to U.S. Provisional Patent Application No. 60/264,147 filed on Jan. 25, 2001, the specification of which is incorporated by reference herein.

FUNDING

Work described herein was supported in part by government funding. The United States Government has certain rights in the invention.

BACKGROUND OF THE INVENTION

The recognition and binding of ligands regulates almost all biological processes, such as immune recognition, cell signaling and communication, transcription and translation, intracellular signaling, and catalysis, i.e., enzyme reactions. There is a long-standing interest in the art to identify and synthesize natural or unnatural ligand molecules which act as agonists or which can agonize or antagonize the activity of ligands such as hormones, growth factors, and neurotransmitters; which induce B-cell (antibody-mediated) or T-cell (cell-mediated) immunity; which can catalyze chemical reactions; or which can regulate gene expression at the level of transcription or translation. A large proportion of such ligands are proteins, peptides, and peptidomimetics.

The traditional approach to ligand and drug discovery relies heavily on a mixture of serendipity and hard work. Screening natural products from animal and plant tissues, or the products of fermentation broths, or the random screening of archived synthetic molecules have been the most productive avenues for the identification of new lead compounds.

However, recent trends in the search for novel pharmacological agents have focused on the preparation of combinatorial libraries as potential sources of new leads for drug discovery. At the heart of this new field of "combinatorial chemistry" is a collection of differing molecules which can be prepared either non-biosynthetically or biosynthetically and screened for biological activity in a variety of formats. Through the use of non-biosynthetic techniques, e.g., encoding, spatially addressing and/or deconvolution, combinatorial libraries of peptides, peptidomimetics and non-peptide-based molecules can be synthesized by batch processes and, importantly, the molecular identity of individual members of the library can be ascertained in a drug screening format (e.g. Lam et al. (1993) Gene 137, 13–16; Dooley et al. (1994) Science 266, 2019–2022). While non-biosynthetic libraries have the advantage of being unrestricted to biological monomers (such as natural amino acids and nucleotides) and their derivatives, they have the disadvantage of being limited in the number of molecules that may be screened within several weeks: usually $10^5$ to $10^8$ at most, which is too few molecules for favoring the identification of high affinity ligands for a target of interest (Roberts (1999) Curr. Op. Chem. Biol. 3, 268–273; Wilson et al. (2001) PNAS 98, 3750–3755). Biosynthetic libraries, however, often do not suffer from this limitation because there are examples of such libraries that enable $10^{15}$ different peptide, RNA or DNA molecules to be screened within several weeks (Roberts, supra). This is achieved by reiterative selection and amplification of individual biosynthetic library members, often with associated mutagenesis steps (e.g. affinity maturation, mutagenic PCR, or DNA shuffling (Roberts, supra)) in a process analogous to Darwinian evolution, sometimes termed directed evolution.

Many prior methods that allowed the isolation of proteins from partially or fully randomized pools did so through an in vivo step. Methods of this sort include monoclonal antibody technology (Milstein, Sci. Amer. 243:66 (1980); and Schultz et al., J. Chem. Engng. News 68:26 (1990)), phage display (Smith, Science 228:1315 (1985); Parmley and Smith, Gene 73:305 (1988); and McCafferty et al., Nature 348:552 (1990)), peptide-lac repressor fusions (Cull et al., PNAS 89:1865 (1992)), and classical genetic selections. Each of these methods relies on a topological link between the protein and the nucleic acid, since only nucleic acids can be replicated. Thus, the information of the protein is retained and can be recovered in readable, nucleic acid form.

Alternative protein selection technologies are performed without in vivo steps. The stalled translation method, often termed ribosome display, is a technique in which selection is for some property of a nascent protein chain that is still complexed with the ribosome and its mRNA (Kawasaki U.S. Pat. No. 5,658,754; Tuerk and Gold, Science 249:505 (1990); Irvine et al., J. Mol. Biol. 222:739 (1991); Korman et al., PNAS 79:1844–1848 (1982); Mattheakis et al., PNAS 91:9022–9026 (1994); Mattheakis et al., Meth. Enzymol. 267:195 (1996); and Hanes and Pluckthun, PNAS 94:4937 (1997)). The mRNA-protein fusion method or mRNA display (Nemoto et al. (1997) FEBS Lett. 414, 405–408; Yanagawa et al. U.S. Pat. No. 6,228,994; Szostak et al. U.S. Pat. Nos. 6,281,344, 6,261,804, 6,258,558, 6,214,553, and 6,207,446; Roberts and Szostak (1997) PNAS 94, 12297–12302) covalently couples the mRNA directly to its protein product via a DNA/puromycin linker. A method for synthesizing "naked" mRNA-peptide fusions that is not compromised by the presence of stop codons is to synthesize peptides in micelles in such a way that they can dissociate from the ribosomes and then rebind to their specific mRNAs (e.g. proteins containing streptavidin sequences will bind to biotinylated mRNA; Doi and Yanagawa (1999) FEBS Lett. 457, 227–230).

The prior art "natural" (L-) peptide library techniques, however, suffer from a number of disadvantages. First, the libraries, which consist almost entirely of chiral monomers (amino acids) lack the enantiomers of the chiral monomers. For example, with L-peptide libraries, while the 20 naturally occurring amino acids provide a wide range of steric, electronic and functional groups, the chirality of the C-alpha carbon effectively limits the three-dimensional shape space which is accessible by the prior art display technology. L-peptide libraries also lack a number of common organic chemistry functional groups which may be helpful for forming non-covalent or covalent complexes with targets (e.g. alkene, alkyl urea, alkyl halide, and ketone), and lack the enormous additional shape diversity achievable with "unnatural" amino acids (either previously synthesized or theoretical). Moreover, as therapeutic agents, peptides with natural L-amino acids are often less preferable than their unnatural enantiomers (D-peptides) or analogs because L-peptides can be limited in use by poor pharmacokinetic profiles due to in vivo processing. For example, L-peptides can be rapidly degraded by proteases after administration to an animal, thus requiring a higher effective dose. Furthermore, pharmaceutical peptides can elicit strong immunogenic responses in patients, further contributing to their rapid clearance and also causing inflammatory reactions that may be toxic. One approach to preventing the degradation of the therapeutic peptide has been to generate non-hydrolyzable peptide analogs such as retro-inverso analogs (c.f., Sisto et al. U.S. Pat. No. 4,522,752), retro-enantio analogs (c.f., Goissis et al. (1976) *J Med Chem* 19:1287–90); trans-olefin derivatives (c.f., Shue et al. (1987) *Tetrahedron Letters* 28:3225); and phosphonate derivatives (c.f., Loots et al., in *Peptides: Chemistry and Biology*, (Escom Science Publishers, Leiden, 1988, p. 118). However, in most instances the backbone of the peptide is altered in order to render the peptidomimetic resistant to proteolysis. In doing so, the resulting peptidomimetic can suffer from decreased bioactivity through loss of certain binding contacts between the natural peptide backbone and target receptor, as well as changes in the steric space relative to the peptide due to alteration in dihedral angles and the like. Another problem is that almost all L-peptides do not cross biological membranes readily because of their hydrophilicity. In contrast, D-peptides and peptides containing other unnatural amino acids (peptidomimetics) such as N-methyl amino acids have increased resistance to proteases, and the peptidomimetic drug Cyclosporin A can cross membranes and is orally available, in part because it contains several N-methyl peptide linkages which are more hydrophobic than natural peptide linkages (Zawadzke and Berg (1992) *J Am Chem Soc* 114:4002; Walsh et al. (1992) *J. Biol. Chem.* 267, 13115–13118). Unfortunately, chemically synthesized (non-biosynthetic) peptidomimetic libraries, such as D-peptide libraries (Lam et al., supra; Dooley et al., supra) suffer the limitation of library size discussed above, and methodological tricks to overcome the size limit of peptidomimetic libraries, such as mirror-image phage or ribosome display (Schumacher et al. (1996) *Science* 271, 1854–1857; Eckert et al. (1999) *Cell* 99, 103–115; Forster et al. PCT publication WO97/35194, are limited by the onerous requirement of chemically synthesizing an enantiomeric target.

Proteins, peptides and peptidomimetics are currently synthesized in three different ways, each with their own inherent limitations:

1. Synthetic peptide chemistry can be used routinely for the synthesis in high yield and purity of very diverse peptidomimetics of up to about 30 residues in length (Eckert et al., supra).

However, the method is inefficient or impractical for longer products because of inefficient coupling steps, purification problems, and folding difficulties. There are also synthetic restrictions because of the need for compatible protecting groups for all of the reactive side chains in a desired product. Furthermore, synthetic peptidomimetics cannot be genetically encoded for reiterative selection, amplification, and mutation (evolution), limiting the complexity of synthetic peptidomimetic libraries to about $10^8$ molecules, too few for optimal drug discovery.

2. In vivo translation using living cells is widely used for the efficient synthesis and posttranslational modification of short or long proteins from a genetically encoded natural or recombinant DNA sequence.

However, synthesis may be inefficient if the gene product is toxic, and there may be difficult purification and refolding problems, particularly if the protein is expressed in inclusion bodies. Most importantly, the method suffers from the inability to incorporate multiple unnatural amino acids selectively or control the post-translation modification process (e.g. protease-catalysed processing or degradation).

3. In vitro translation with crude cell extracts generally overcomes the toxicity problem (but does not control post-translational modifications), may result in easier purification and folding, and allows the selective incorporation of a single unnatural amino acid per protein using an artificial suppressor tRNA (Noren et al. (1989) *Science* 244, 182–188).

However, the incorporation of an unnatural amino acid by this approach usually suffers from much lower yields than in vivo systems because it relies on inherently inefficient suppressor tRNAs competing with termination factors. Although over one hundred different unnatural amino acids have been incorporated on an individual basis (e.g. Mendel et al. (1995) *Annu. Rev. Biophys. Biomol. Struct.* 24, 435–462), this strategy has been restricted to selective incorporation of only a single unnatural amino acid per protein at only one of the three termination (nonsense) codons (the UAG codon) because of competition at amino acid (sense) codons from natural amino acids catalysed by the tRNA charging and proofreading activities of the twenty different aminoacyl tRNA synthetases, and because an attempt to use a second termination codon (UGA) failed due to readthrough by the ribosome (Cload et al. (1996) *Chem. and Biol.* 3, 1033–1038).

Many attempts to incorporate unnatural amino acids selectively at sense codons in a generalizable manner have also failed. For example, in the most commonly used method for unnatural amino acid incorporation, where a high-specific-activity, radioactive-isotope derivative of a natural amino acid is incorporated by in vitro translation to synthesize a radiolabelled protein, it is well known that the specific activity of the radioactive amino acid is always substantially reduced by competition for incorporation by the unlabelled version of the amino acid present in the crude translation system, despite withholding the unlabelled version from the added unlabelled amino acid pool. Analogous analog dilution results are obtained by the Promega company using their commercially available kit for incorporation of another reporter group, biotin-labelled lysine (literature accompanying Transcend™ non-radioactive translation systems). Furthermore, filtration of a crude translation extract to remove natural amino acids followed by supplementation with all of the natural amino acids except lysine and supplementation with a lysine tRNA charged with an amino acid analog resulted in incorporation of lysine analog to lysine at a ratio of only 1:3 to 1:4 (Crowley et al. (1993) *Cell* 73, 1101–1115). While a low selectivity of amino acid analog incorporation is sufficient for certain applications (Rothschild et al., U.S. Pat. No. 5,643,722) it is clearly incompatible with many applications such as that requiring the amplification and characterization of genetically encoded specific peptidomimetic sequences. It has proved possible to incorporate two different unnatural amino acids using two different frameshifting suppressor tRNAs (Hohsaka et al. (1999) *JACS* 121, 12194–12195), and many identical unnatural amino acids have been incorporated using an inhibitor specific for Phe aminoacyl-tRNA synthetase (Baldini et al. (1988) *Biochem.* 27, 7951–7959). However, both of these methods are not generalizable in the manner necessary for the incorporation of many different unnatural amino acids into a single peptidomimetic. In order to overcome these restrictions inherent in crude and in vivo translations, an elaborate strategy for expansion of the genetic code based on orthogonal tRNAs and orthogonal unnatural nucleic acid base pairs has been proposed, but development beyond a single in vitro-engineered termination codon (Bain et al. (1992) *Nature* 356, 537–539) has proved to be too challenging technically (Service (2000) *Science* 289, 232–235).

We envisioned that this problem potentially may be solved by using a pure in vitro translation system. Competition between unnatural amino acids and natural amino acids or termination factors could potentially be avoided by the omission of certain components such as certain amino acids, tRNAs, aminoacyl tRNA synthetases and/or termination factors. Unfortunately, the minimal requirements for mRNA-dependent polypeptide synthesis have been difficult to define because of the large number of macromolecules involved. Reconstitution of translation from purified components has been achieved for *E. coli*, but the number of translation factors required remains controversial.

The first purified translation system, constructed by the Weissbach laboratory, efficiently translated four *E. coli* mRNAs with strong dependencies on high salt-washed ribosomes, initiation factors (partial IF1 dependency), elongation factor Tu (EF-TuH), and groups of aminoacyl-tRNA synthetases, and partial dependencies on met-tRNA$_i^{fMet}$ formyltransferase and elongation factor G (EF-G), with no dependency on elongation factor Ts (EF-Ts) or termination factors (Kung et al. (1978) *Arch. Biochem. and Biophys.* 187, 457–463). Because of the difficulties in maintaining so many purified components and in removing trace contaminants, the search for additional general translation factors was facilitated by simplifying the system to di- or tripeptide synthesis from fMet-tRNA$_i^{fMet}$ and one or two elongator aminoacyl-tRNAs, thereby avoiding the requirement for aminoacyl-tRNA-synthesizing enzymes (Weissbach et al. (1984) *Biotechniques* 2, 16–22).

When a second group, led by Ganoza, extended the latter simplified approach to longer peptides using in vitro-charged total tRNA and release factors, translation of bacteriophages MS2 and f1 were found to be dependent on three additional factors, termed EF-P, W and rescue (Green et al. (1985) *Biochem. Biophys. Res. Com.* 126, 792–798; Ganoza et al. (1985) *PNAS* 82, 1648–1652). The absence of these factors resulted in innefficient processivity. For example, there was a predominance of di-, tri-, tetra- and pentapeptide pausing or premature termination products in hexapeptide synthesis reactions. A possibly related translation factor termed deaD/W2 (several kD bigger than W) and also EF-P have been cloned, are necessary for maximal growth, and are homologous to eukaryotic initiation factors (Aoki et al. (1991) *Nucleic Acids Res.* 19, 6215–6220; Aoki et al. (1997) *J. Biol. Chem.* 272, 32254–32259; Lu et al. (1999) *Int. J. Biochem. Cell Biol.* 31, 215–229).

In apparent conflict with the results of Ganoza, two other groups have reported synthesis of short peptides from aminoacyl-tRNA substrates using purified components without the addition of EF-P, W, W2 or rescue, although these two groups did not directly document the processivity of their systems or the purity of their ribosomes (Stade et al. (1995) *Nucleic Acids Res.* 23, 2371–2380; Pavlov et al. (1997) *EMBO J.* 16, 4134–4141). If the discrepancy is real, one can only speculate as to the explanation. For example, because EF-P, W, and rescue can be purified from ribosome preparations (Ganoza et al. (1996) *Biochemie* 78, 51–61), it is possible that the ribosomes used by the latter two groups, prepared by very different procedures from that used by Ganoza's group, were contaminated with EF-P, W, W2 and/or rescue. This is problematic because contamination with EF-P, W, W2 and/or rescue likely implies contamination with more abundant proteins, such as aminoacyl-tRNA synthetases and termination factors, that could cause unwanted reactions. Alternatively, EF-P, W, W2 and/or rescue may only be required for efficient processivity in Ganoza's system.

The ability to synthesize peptides or proteins from a pure translation system without added EF-P, W (sometimes called W2) and rescue is desirable, if possible, because these proteins are not well understood in terms of function, resulting in difficulty in assaying their activities and therefore following the purification of active protein. Furthermore, there is controversy with respect to the actual size of W (or W2) and whether W and W2 represent derivatives of the same proteins, and the gene for rescue is yet to be cloned.

SUMMARY OF THE INVENTION

The present invention is a simplified, highly-purified, processive translation system that does not require the addition of translation factors EF-P, W, W2 or rescue. A new translation process offers new, potentially improved, routes to all peptides and proteins currently synthesized by alternative routes. This process overcomes the limitations inherent in methods 1, 2 and 3 described above for protein, peptide and peptidomimetic synthesis.

In one preferred embodiment, the purified system can be used for the synthesis of peptide or protein ligands or catalysts, such as insulin, growth hormone or erythropoietin.

In another preferred embodiment, the purified system can be used for "pure ribosome display" and "pure mRNA display" selection experiments, in contrast to existing ribosome and mRNA display systems which rely on crude cell extracts. There are several advantages associated with performing peptide and protein display in a pure system, such as an expected lack of post-translational modification of peptides, a lack of proteases which often cause protein degradation problems, and a lack of competition from contaminants in the selection steps. Additional advantages include:

(i) The absence of ribonucleases (demonstrated by measured long-term stability of radioactive mRNA in our pure *E. coli* system (results not shown)) avoids problems associated with mRNA degradation observed in various crude systems, especially *E. coli* (Roberts, supra); it is obviously important that the mRNA not be degraded before it can be translated and selected.

(ii) It is expected that the pure reconstituted system is not contaminated by translation termination factors. Indeed, our system is stimulated by addition of termination factors. Workers using the most popular crude display systems have found it necessary to remove stop codons from mRNAs to avoid rapid release of nascent peptides before either selection or before fusion to the mRNA conjugate before selection (both fusion and selection are slow processes). The removal of stop codons usually requires special mutagenesis steps in the case of individual mRNAs, and is more problematic for natural mRNA libraries or synthetic combinatorial libraries where it is impossible to specifically mutate all stop codons. The problem with stop codons in libraries has been circumvented by either randomly generating libraries of small subdomains of proteins (which lack full-length proteins, have under-represented carboxy-terminal subdomains, encode many inappropriate boundaries with respect to ability to fold correctly, and contain an abundance of sequences from unnatural open reading frames) or by selecting out members of random libraries that contain stop codons (thereby wasting a major portion of the synthetic reaction and diversity; Cho et al. (2000) *J. Mol. Biol.* 297, 309–319). In the purified ribosome or purified mRNA display systems, the peptidyl-tRNA can remain stably associated with the ribosome for more than a day (stability is especially favored if, after translation is complete, the temperature is lowered and/or the salt concentration is increased (Schaffitzel et al. (1999) *J. Immunol. Methods* 231, 119–135)): either the ribosome stops elongating at a sense codon for which no tRNA is provided (thereby avoiding competition with termination factors altogether), or it stops at a stop codon, or it stops at the end of mRNAs lacking a stop codon. Thus, libraries of full-length translation products from natural mRNAs can be prepared with this invention, and such expression libraries can be either directly subjected to in vitro selection or they can be spacially addressed by hybridization to a DNA microchip for genomic and proteomic studies.

(iii) It is expected that the pure reconstituted system is not contaminated by the tmRNA system that degrades peptides synthesized from mRNAs lacking a stop codon. Workers using the crude system have found it important to try to inhibit this tmRNA system (Hanes and Pluckthun (1997) *PNAS* 94, 4937–4942).

In another preferred embodiment, the invention enables the mRNA-directed synthesis of specific peptidomimetics (peptide analogs) in a generalizable manner, greatly increasing the diversity and length of peptidomimetics available. Possibilities include existing peptidomimetic ligands and drugs (including non-ribosomally biosynthesized ligands, such as Cyclosporin A) and derivatives thereof.

In another embodiment, the invention enables the genetic encoding of peptidomimetic products for catalyst, ligand and drug discovery by in vitro evolution (e.g. by using pure ribosome display or pure mRNA display described above). Specific synthesis of peptidomimetics is not possible in existing crude ribosome and mRNA display methodologies because natural amino acids compete with unnatural amino acids for incorporation in crude translation systems.

The invention facilitates the isolation of peptides and peptidomimetics with desired properties. In one embodiment, the method is directed to identifying ligands for a target molecule. Exemplary target molecules include peptides, nucleic acids, carbohydrates and non-polymeric molecules, such as steroids, inositols, lipid soluble vitamins, terpenes, acetogenims, neurotransmitters, or a transition state analog. In a preferred embodiment, the target molecule is a protein. The protein target can be, to illustrate, a receptor, an enzyme, a DNA-binding protein or a protein complex, or a portion or domain thereof which retains a screenable activity.

In preferred embodiments, the subject method is used to generate variegated population of test peptides or peptidomimetics of at least $10^3$ different sequences, though more preferably at least $10^8$ different sequences, and most preferably at least $10^{15}$ different sequences.

Yet another aspect of the invention relates to compounds, such as peptides and peptidomimetics, identified by the subject method, and their uses. This also includes conjugates and derivatives of such peptides and peptidomimetics (e.g. conjugation to cationic peptide sequences that enable efficient transport across membranes of attached peptide or peptidomimetic sequences (Moore and Rosbash (2001) *Science* 294, 1841–1842).

Another aspect of the invention relates to kits for synthesis and/or evolution of peptides or peptidomimetics.

DESCRIPTION OF THE DRAWINGS

FIG. 3. Short mRNA templates. The DNA primer-template pair used to synthesize the longest mRNA is illustrated at the top. The predicted translation products from our purified system are also shown (aminoacyl tRNAs for the 3' terminal codons GAA (Glu) and UUC (Phe) were not used). bK: biotin-labeled-lysine. S-D: Shine and Dalgarno ribosome binding site. The SEQ ID NOs for the nucleic acid and their respective amino acid sequences, where applicable, are designated as follows: T7 RNA pol, promoter (SEQ ID NO: 1); reverse complement of mRNA MTTV and T7 RNA pol promoter, (SEQ ID NO:2); mRNA MTTV (SEQ ID NOS: 3 and 10); mRNA MTV (SEQ ID NOS: 4 and 11); mRNA MV (SEQ ID NOS: 5 and 12); mRNA MVT (SEQ ID NOS: 6 and 13); mRNA scramble-epsiMVT (SEQ ID NOS: 7 and 13); mRNA ΔepsiMVT (SEQ ID NOS: 8 and 13); mRNA MTKV (SEQ ID NOS: 9 and 14).

FIG. 15. Three anticodon mutants of tRNA$^{Asn}$(N) termed, from left to right, tRNA$^{Asn}$(T) (SEQ ID NOS: 25 and 28) tRNA$^{Asn}$(S) (SEQ ID NOS: 26 and 29) tRNA$^{Asn}$(V) (SEQ ID NOS: 27 and 30). The new anticodons of the tRNAs are indicated with large letters above the codons that they recognise. The genetic code has been redesigned so that the codons now specify whichever amino acid (natural or unnatural) is chosen to be ligated onto each tRNA$^{Asn-CA}$.

FIG. 19. Our spacer mRNAs (SEQ ID NO: 34) and their encoded polypeptide products: 13-mer (SEQ ID NO: 36), 21-mer (SEQ ID NO: 35), 41-mer (SEQ ID NO: 37), 53-mer (SEQ ID NO: 38, 61-mer (SEQ ID NO: 39, 101-mer (SEQ ID NO: 40).

(FIG. 18) that differs in that the mRNAs are conjugated with puromycin (Pm) to enable covalent fusion of the mRNAs to their peptide or peptidomimetic products. Thus, the mRNA-peptidomimetic fusion may be purified from other translation components before selection, enabling very short peptidomimetics to be displayed without masking by the ribosome tunnel. Since the fusion reaction is slow, it is important to omit release factors when using mRNAs containing stop codons to prevent release factor-catalysed peptide release. Typically, ribosomes are stalled by a deoxynucleotide sequence conjugated to the mRNA. We ligated mMTKV and mMTCV (FIGS. 8 and 11) to pdA$_{27}$dCdCPm (SEQ ID NO: 41) (Trilink) efficiently using a custom-synthesized "splint" DNA (TTTTTTTTTTAATTCAAC, (SEQ ID NO: 46) designed to hybridize to the ends of either mRNA and also the pdA$_{27}$dCdCPm), and T4 DNA ligase, then gel-purified the conjugates for use in fusion and selection experiments (Roberts and Szostak (1997) *PNAS* 94, 12297–12302) where X in the figure is a readily selectable amino acid such as C or bC (FIG. 9) or bK (FIG. 22).

Figure 1:
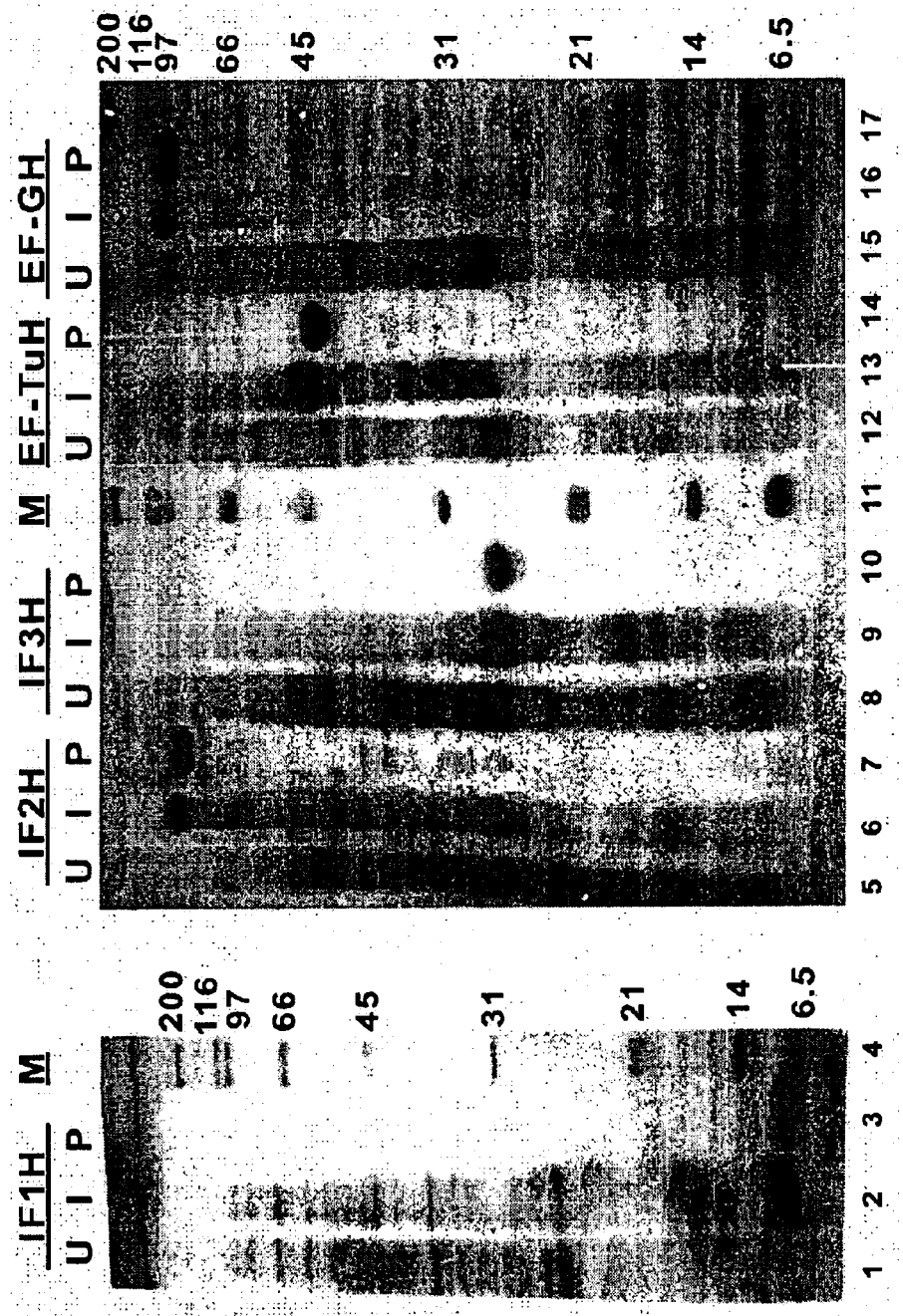
FIG. 1. Over-expression and purification of five his-tagged *E. coli* translation factors from *E. coli*. After SDS-PAGE on 15% gels, samples were stained with Coomassie Blue. U, uninduced total cells; I, IPTG-induced total cells; P, purified protein eluted from $Ni^{2+}$ beads; M, molecular weight marker proteins (sizes indicated in kD).

DETAILED DESCRIPTION OF THE INVENTION (I) Overview

The present invention relates to an in vitro translation system that has been reconstituted from purified components to enable the specific incorporation of multiple different natural and unnatural amino acid residues in a highly controlled and generalizable manner. Because of the removal of unwanted competition from certain wild-type amino acids and termination factors, the efficient and specific synthesis of genetically encoded small and long peptidomimetic molecules and libraries is possible.

This invention was developed because the long-felt need for a biosynthetic method capable of synthesizing genetically encoded peptidomimetics remained unsolved, despite considerable effort over many years by many workers skilled in the art.

This invention was also developed because of a long-felt need for a simplified highly purified translation system that does not require the addition of EF-P, W, W2 or rescue for efficient processivity. Based on the problems with processivity of translation in the most highly purified versions of such systems in the prior art and on the decades of research in the field without a clear solution, there appeared to be a low expectation of success.

(II) Definition of Terms

For convenience, certain terms employed in the specification, examples, and appended claims are collected here.

By a "protein" is meant any two or more naturally occurring amino acids, joined by one or more peptide bonds. "Protein" and "peptide" are used interchangeably herein.

The term "peptide" refers to an oligomer in which the monomers are natural amino acids (alpha-amino acids) joined together through amide bonds. Peptides are two or more amino acid monomers long, but more often are between 5 to 10 amino acid monomers long and can be even longer, i.e. up to 20 amino acids or more, although peptides longer than 20 amino acids are more likely to be called "polypeptides." The term "protein" is well known in the art and usually refers to a very large polypeptide, or set of associated homologous or heterologous polypeptides, that has some biological function. For purposes of the present invention the terms "peptide," "polypeptide," and "protein" are largely interchangeable, as all three types can be synthesized by the translation system, and so are collectively referred to as peptides.

By "peptidomimetic" is meant a peptide analog containing one or more unnatural amino acids (e.g. unnatural side chains, unnatural chiralities, N-substituted amino acids, or beta amino acids), unnatural topologies (e.g. cyclic or branched) or unnatural chemical derivatives (e.g. methylated or terminally blocked), or any molecule, other than a peptide containing natural amino acids, that is synthesized by a ribosome, including those products that have unnatural backbones and even those with partially or totally substituted amide (peptide) bonds with ester, thioester or other linkages (Mendel, supra).

By the terms "amino acid residue" and "peptide residue" is meant an amino acid or peptide molecule without the —OH of its carboxyl group (C-terminally linked) or the proton of its amino group (N-terminally linked). In general the abbreviations used herein for designating the amino acids and the protective groups are based on recommendations of the IUPAC-IUB Commission on Biochemical Nomenclature (see *Biochemistry* (1972) 11:1726–1732). Amino acid residues in peptides are abbreviated as follows: Alanine is Ala or A; Cysteine is Cys or C; Aspartic Acid is Asp or D; Glutamic Acid is Glu or E; Phenylalanine is Phe or F; Glycine is Gly or G; Histidine is His or H; Isoleucine is Ile or I; Lysine is Lys or K; Leucine is Leu or L; Methionine is Met or M; Asparagine is Asn or N; Proline is Pro or P; Glutamine is Gln or Q; Arginine is Arg or R; Serine is Ser or S; Threonine is Thr or T; Valine is Val or V; Tryptophan is Trp or W; and Tyrosine is Tyr or Y. Formyl-methionine is abbreviated as fMet or fM. By the term "residue" is meant a radical derived from the corresponding .alpha.-amino acid by eliminating the OH portion of the carboxyl group and the H portion of the α-amino group. The term "amino acid side chain" is that part of an amino acid exclusive of the —CH(NH$_2$)COOH portion, as defined by K. D. Kopple, "Peptides and Amino Acids", W. A. Benjamin Inc., New York and Amsterdam, 1966, pages 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or —H (the side chain of glycine).

In certain embodiments, the amino acids used in the application of this invention are those naturally occurring amino acids found in proteins. Particularly suitable amino acid side chains include side chains selected from those of the following 21 natural amino acids: alanine, arginine, asparagine, aspartic acid, cysteine, glutamic acid, glutamine, glycine, histidine, isoleucine, leucine, lysine, methionine, phenylalanine, proline, selenocysteine, serine, threonine, tryptophan, tyrosine, and valine. However, the present invention specifically contemplates the use of analogs, derivatives and congeners of any specific amino acid referred to herein. For example, the present invention contemplates the use of radioactive amino acid analogs, amino acid analogs wherein a side chain is lengthened or shortened while still providing a carboxyl, amino or other reactive precursor functional group for polymerization, as well as amino acid analogs having variant side chains (with appropriate functional groups). For instance, the subject peptidomimetic can include an amino acid analog as for example, β-cyanoalanine, canavanine, djenkolic acid, norleucine, 3-phosphoserine, homoserine, dihydroxyphenylalanine, 5-hydroxytryptophan, 1-methylhistidine, 3-methylhistidine, allyl glycine (or its alkyne derivative), O-methyl-serine, biotinyl-lysine, biotinyl-cysteine (or other biotin-labelled amino acids) cyclohexylalanine, homoglutamate, D-alanine (or other D-amino acids), N-methyl glycine (or other N-methyl amino acids), epsilon-N-methyl-lysine, and radio-isotope derivatives of the 21 natural amino acids or unnatural amino acids. Other naturally or non-naturally occurring amino acids which are suitable herein will be recognized by those skilled in the art and are included in the scope of the present invention.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of dissymmetry and whose molecules are not mirror images of one another. With respect to the nomenclature of a chiral center, terms "D" and "L" configuration are as defined by the IUPAC Recommendations. As to the use of the terms, diastereomer, racemate and enantiomer will be used in their normal context to describe the stereochemistry of peptide preparations.

The terms "D-amino acid" and "L-amino acid" each denote an absolute configuration by convention relative to the possible stereoisomers of glyceraldehyde. Thus, all stereoisomers that are stereochemically related to L-glyceraldehyde are designated L-, and those related to D-glyceraldehyde are designated D-, regardless of the direction of the rotation of plane of polarized light by the given isomer. In the case of threonine and isoleucine, there are two stereochemical centers, i.e., the Cα and the Cβ atoms. The D-threonine and D-isoleucine employed herein preferably have stereochemistries at both chiral sites which are opposite (enantiomeric) to the stereochemistry of the L-enantiomers of those amino acids, e.g., they are complete mirror images. Glycine is the only commonly occurring achiral amino acid. The presence of achiral amino acid residues such as glycine do not affect the designation of its chirality.

All chiral amino acids in protein synthesized de novo in nature, e.g., "naturally occurring" are L-amino acids.

A "D-enantiomer" or "D-peptide enantiomer" refers to a peptide comprised of D-amino acid residues, as opposed to L-amino acids.

The term "synthetic" refers to production by in vitro chemical or enzymatic synthesis.

By "DNA" is meant a sequence of two or more covalently bonded, naturally occurring or modified deoxyribonucleotides.

By "RNA" is meant a sequence of two or more covalently bonded, naturally occurring or modified ribonucleotides. Two examples of modified RNAs included within this term are phosphorothioate RNA, and "transfer RNA" containing natural modified bases.

By "transfer RNA" or "tRNA" is meant any RNA molecule that can deliver peptide or peptidomimetic precursors to the ribosome in a manner specified by partial base-pairing to an mRNA.

By a "translation initiation sequence" is meant any sequence which is capable of providing a functional ribosome entry site. In bacterial systems, this region is sometimes referred to as a ribosome-binding or Shine-Dalgarno sequence.

By "messenger RNA" or "mRNA" is meant any nucleic acid containing a "translation initiation sequence".

A "reconstituted translation system" refers to a reaction mixture (a) capable of performing in vitro translation, e.g., mRNA-dependent protein synthesis, and (b) characterized by having less than 10 percent of the contaminating proteins found in cell lysate translation systems or wheat germ extract translation systems, and more preferably having less than 5 percent or even less than 1 percent of such contaminating proteins. In certain preferred embodiments, the subject reconstituted translation system is generated by admixing recombinantly produced and/or purified proteins.

By a "start codon" is meant three bases which signal the beginning of a protein coding sequence. Generally, these bases are AUG (SEQ ID NO: 42) (or ATG); however, any other base triplet capable of being utilized in this manner may be substituted.

By a "stop codon" is meant three bases which signal the end of a protein coding sequence. Generally, these bases are UAG, UAA or UGA (where U may be substituted by T); however, any other base triplet capable of being utilized in this manner may be substituted.

By a "pause sequence" is meant a nucleic acid sequence which causes a ribosome to slow or stop its rate of translation, such as a DNA sequence.

By a "peptide acceptor" is meant any molecule capable of being added to the carboxyl-terminus of a growing protein chain by the catalytic activity of the ribosomal peptidyl transferase function. Typically, such molecules contain (i) a nucleotide or nucleotide-like moiety (for example, adenosine or an adenosine analog (dimethylation at the N-6 amino position is acceptable)), (ii) an amino acid or amino acid-like moiety (for example, any of the 20 D- or L-amino acids or any amino acid analog thereof (for example, 0-methyl tyrosine or any of the analogs described by Ellman et al., *Meth. Enzymol.* 202:301, 1991), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure.

By "highly selective incorporation at each codon", it is meant at least 80 percent selective incorporation of an amino acid residue at a position in the peptide or peptidomimetic corresponding to the codon, more preferably at least 90, 95 or even 98 percent selective incorporation.

By a peptide acceptor being positioned "at the 3' end" of a protein coding sequence is meant that the peptide acceptor molecule is positioned after the final codon of that protein coding sequence. This term includes, without limitation, a peptide acceptor molecule that is positioned precisely at the 3' end of the protein coding sequence as well as one which is separated from the final codon by intervening coding or non-coding sequence (for example, a sequence corresponding to a pause site). This term also includes constructs in which coding or non-coding sequences follow (that is, are 3' to) the peptide acceptor molecule. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a peptide acceptor molecule.

By "covalently bonded" to a peptide acceptor is meant that the peptide acceptor is joined to a "protein coding sequence" either directly through a covalent bond or indirectly through another covalently bonded sequence (for example, DNA corresponding to a pause site).

By "mRNA-display" is meant any method for coupling, via covalent or non-covalent linkage(s), the peptide or peptidomimetic product from translation of a mRNA to its cognate mRNA or cDNA or nucleotide sequence related to the peptide or peptidomimetic product. A commonly used linkage contains puromycin.

By an "altered function" is meant any qualitative or quantitative change in the function of a molecule.

By "binding partner," as used herein, is meant any molecule which has a specific, covalent or non-covalent affinity for a portion of a desired mRNA-peptide/peptidomimetic ribosomal complex or fusion. Examples of binding partners include, without limitation, members of antigen/antibody pairs, protein/inhibitor pairs, receptor/ligand pairs (for example cell surface receptor/ligand pairs, such as hormone receptor/peptide hormone pairs), enzyme/substrate pairs (for example, kinase/substrate pairs), lectin/carbohydrate pairs, oligomeric or heterooligomeric protein aggregates, DNA binding protein/DNA binding site pairs, RNA/protein pairs, and nucleic acid duplexes, heteroduplexes, or ligated strands, as well as any molecule which is capable of forming one or more covalent or non-covalent bonds (for example, disulfide bonds) with any portion of an RNA-protein fusion.

The term "ligand" refers to a molecule that is recognized by a particular target, such as a protein, e.g., a receptor. Any agent bound by or reacting with a target is called a "ligand," so the term encompasses the substrate of an enzyme and the reactants of a catalyzed reaction. The term "ligand" does not imply any particular molecular size or other structural or compositional feature other than that the substance in question is capable of binding or otherwise interacting with a target. A "ligand" may serve either as the natural ligand to which the target binds or as a functional analog that may act as an agonist or antagonist.

The term "substrate" refers to a ligand of an enzyme which is catalytically acted on and chemically converted by the enzyme to product(s).

The term "receptor" refers to a molecule that has an affinity for a given ligand.

The term "solid support" refers to a material having a rigid or semi-rigid surface. Such materials will preferably take the form of small beads, pellets, disks, chips, dishes, multi-well plates, wafers or the like, although other forms may be used. In some embodiments, at least one surface of the material will be substantially flat. The term "surface" refers to any, generally two-dimensional, structure on a solid material and may have steps, ridges, kinks, terraces, and the like without ceasing to be a surface.

As used herein, by a "population" is meant more than one molecule (for example, more than one RNA, DNA, RNA-protein or RNA-peptidomimetic fusion molecule). Because the methods of the invention facilitate selections which begin, if desired, with large numbers of candidate molecules, a "population" according to the invention preferably means at least $10^3$ different sequences, though more preferably at least $10^8$ different sequences, and most preferably at least $10^{15}$ different sequences.

The term "random peptide library" refers to a population of random or semi-random peptides, as well as a population of fusion proteins containing those random peptides (as applicable). A similar meaning is given to the term "random peptidomimetic library", but with the understanding that one or more residues of the peptidomimetic are non-naturally occurring amino acid-like moieties.

By "selecting" is meant substantially partitioning a molecule from other molecules in a population. As used herein, a "selecting" step provides at least a 2-fold, preferably, a 10-fold, more preferably, a 100-fold, and, most preferably, more than 1000-fold enrichment of a desired molecule relative to undesired molecules in a population following the selection step. As indicated herein, a selection step may be repeated any number of times, and different types of selection steps may be combined in a given approach.

The phrases "individually selective manner" and "individually selective binding", with respect to binding of a test peptide or peptidomimetic with a target, refers to binding specific for, and dependent on, the molecular identity of the target.

The language "differential binding means", as well as "affinity selection" and "affinity enrichment", refer to the separation of members of the peptide or peptidomimetic display library based on the differing abilities of test peptides or peptidomimetics on each of the display packages of the library to bind to the target. The differential binding of a target by molecules of the display can be used in the affinity separation of molecules which specifically interact with the target from those which do not. Examples of affinity selection means include affinity chromatography, precipitation, fluorescence activated cell sorting, and plaque lifts. As described below, the affinity chromatography includes panning techniques using, e.g., immobilized target proteins.

The term "reporter group" or "tag" refers to an atom, compound, or biological molecule or complex that can be readily detected when attached to other molecules and exploited in chemical separation processes. A reporter group can be, for example, a fluorescent or radioactive atom or a compound containing one or more such atoms.

By "proofreading" activity of an aminoacyl tRNA synthetase is meant the hydrolytic catalytic activity of the enzyme that recognises and then removes non-cognate amino acids (natural or unnatural) from the aminoacylated cognate tRNA isoacceptors of the synthetase.

(III) Exemplary Embodiments

In general, the inventive method consists of an in vitro or in situ transcription/translation protocol that generates peptides or peptidomimetics. This is accomplished by synthesis and in vitro or in situ translation of an mRNA molecule with one or more tRNA molecules that are charged with naturally and/or non-naturally occurring amino acids or amino acid analogs. We have discovered that bacterial translation can be reconstituted without added EF-P, W, W2, or rescue.

In general, a preferred minimal translation system includes the following macromolecular components: ribosomes, mRNA, aminoacyl tRNAs, and translation factors IF2H, IF3H, EF-TuH and EF-GH. IF1H and EF-Ts are stimulatory, and are often added. Additional alterations are detailed below.

The lack of availability of clones designed for high-level over-expression of tagged initiation factors has made the reproducible preparation of large quantities of highly purified factors to reconstruct a purified translation system a major technical challenge. Indeed, many studies have relied on gifts of key components. In order to overcome this problem, we subcloned and overproduced all three E. coli initiation factors with $(His)_6$ tags (termed his-tags) and tested the activity of each factor in a purified translation system.

Subcloning, over-expression and purification of his-tagged E. coli translation factors. Published clones for the expression of E. coli IF1, IF2 and IF3, though useful in numerous initiation studies, are for untagged factors that cannot be affinity purified, and, with one exception, are thermally inducible (Calogero et al. (1987) *Mol Gen Genet* 208, 63–9; Laalami et al. (1991) *J Mol Biol* 220, 335–49; De Bellis and Schwartz (1990) *Nucleic Acids Res* 18, 1311; Mortensen et al. (1991) *Biochimie* 73, 983–9; Brombach and Pon (1987) *Mol Gen Genet* 208, 94–100). An important consideration for IF3 over-expression is the presence of the rare AUU initiation codon (Brombach and Pon (1987) *Mol Gen Genet* 208, 94–100). Initiation codon pairing with fmet-tRNA$_f^{fmet}$ is directly proofread by IF3 (Meinnel et al. (1999) *J Mol Biol* 290, 825–37), thereby enabling IF3-mediated feedback repression of translation of its own gene in vivo (Brombach and Pon (1987) *Mol Gen Genet* 208, 94–100). Thus, to increase the expression levels and to simplify purification of all three initiation factors, we replaced the initiation codons with an AUG(CAC)$_6$ sequence by PCR, and subcloned the coding sequences into a pET-derived expression plasmid (see Materials and Methods). The resulting his-tagged clones were non-toxic and overproduced the factors (termed IF1H, IF2H and IF3H) at very high levels in the soluble fraction of the lysate (FIG. 1, lanes 1,2,5,6,8,9). In addition, *E. coli* EF-Tu and EF-G with N-terminal his$_6$ tags (termed EF-TuH and EF-GH) were over-expressed using available clones (FIG. 1, lanes 12,13, 15,16; (Hwang et al. (1997) *Arch Biochem Biophys* 348, 157–62; Semenkov et al. (1996) *Proc Natl Acad Sci USA* 93, 12183–8)). Gel analysis of the Ni$^{2+}$-purified initiation and elongation factors is also shown in FIG. 1 (lanes 3, 7, 10, 14 and 17). IF2H, IF3H, EF-TuH and EF-GH comigrated with samples of the authentic *E. coli* proteins (data not shown), and IF1H had the expected electrophoretic mobility based on comparison with molecular weight markers (FIG. 1, lanes 1–4). IF2-2, a shorter form of IF2, was probably over-expressed together with IF2H (FIG. 1, lane 6), but, because its synthesis by internal translation initiation (Sacerdot et al. (1992) *J Mol Biol* 225, 67–80) would not incorporate a his$_6$ tag, it did not copurify with IF2H (FIG. 1, lane 7).

Figure 2:
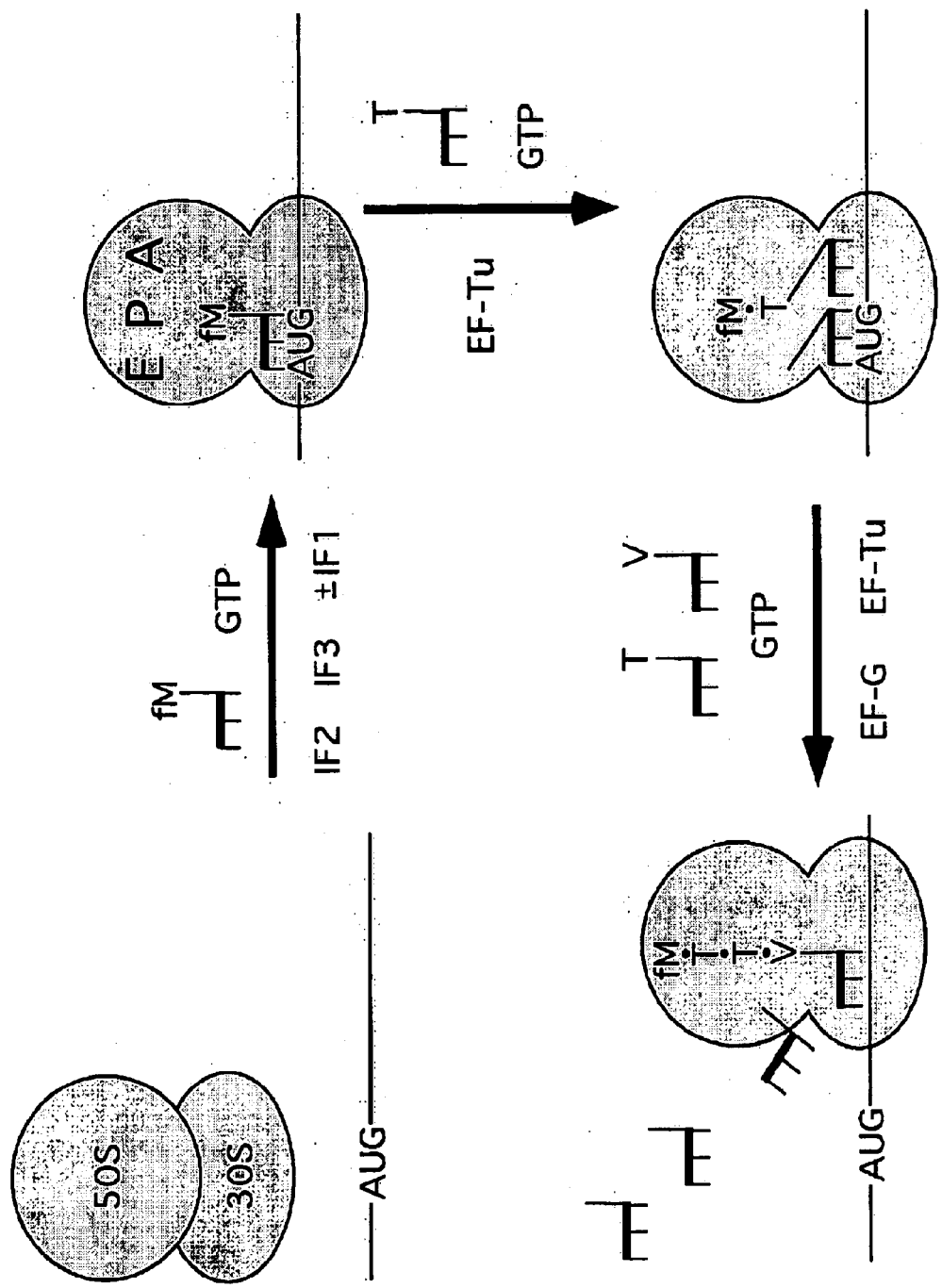
FIG. 2. Schematic illustrating steps in ribosome-directed peptide synthesis. The three enzymatic reactions depicted by arrows are initiation (top), the first elongation step (right), and subsequent translocation and elongation steps (bottom). Peptide products can be released from the peptidyl-tRNAs by base-catalyzed hydrolysis for analysis. Products GDP and $P_i$ are not shown. E, exit site; P, peptidyl site; A, aminoacyl site.

Dependencies of his-tagged initiation factors in an initiation assay. The activity and purity of the three initiation factors were measured by ribosome: fmet-tRNA$_f^{fmet}$: ApUpG trinucleotide complex formation (FIG. 2, top line). Dependencies of the his-tagged initiation factors in initiation complex formation with the 3× salt-washed ribosomes were comparable to those reported for native factors (Table 1; Kung et al. (1974) *Arch Biochem Biophys* 162, 578–84; Dubnoff and Maitra (1972) *J Biol Chem* 247, 2876–83). The variation in IF3 dependence may result from different amounts of free 30S ribosomal subunits in the different 70S ribosome preparations because IF3 does not strongly stimulate initiation complex formation when free 30S subunits are substituted for 70S ribosomes in the assay (Canonaco et al. (1987) *Biochimie* 69, 957–63). Given that initiation factors tend to copurify with ribosomes (Kung et al. (1974) *Arch Biochem Biophys* 162, 578–84), the results also attest to the purity of the ribosomes. Substitution of the AUG trinucleotide template with the MTTV mRNA template (FIG. 3; described below) at a much lower concentration (0.3 μM) enables complex formation with equivalent yield (data not shown).

Dependencies of his-tagged factors in tripeptide synthesis. We next tested whether initiation complexes were competent to undergo elongation in a purified translation system using the components depicted in FIG. 2. The mRNA design we selected (Pavlov et al. (1997) *Biochimie* 79, 415–22) contains an optimal Shine-Dalgarno sequence and an epsilon translational enhancer (Olins and Rangwala (1989) *J Biol Chem* 264, 16973–6). Our design (FIG. 3) has the advantage of encoding mRNAs short enough to be synthesized directly from a single long synthetic DNA template hybridized to a standard 18-mer oligodeoxyribonucleotide without the need for cloning (Milligan and Uhlenbeck (1989) *Methods in Enzymology* 180, 51–62). Translations of the templates are completed when the ribosomes translocate to a codon for which there is no supplied cognate aminoacyl tRNA (Weissbach et al. (1984) *BioTechniques* 2, 16–22).

Figure 4:
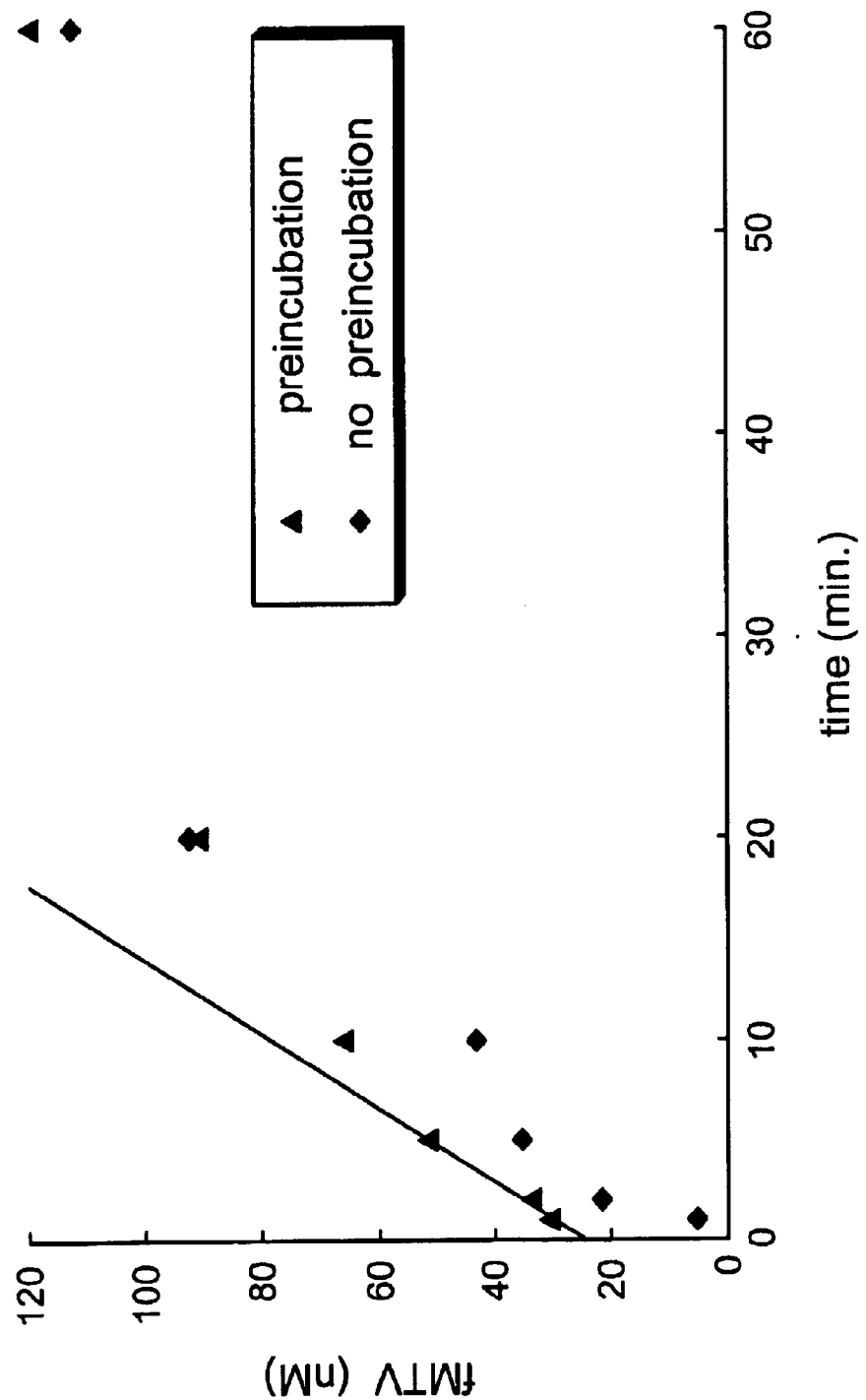
FIG. 4. Characterization of oligopeptide synthesis rates from mRNA MTV in a purified his-tagged translation system. fMTV (SEQ ID NO: 11) was measured by $^3$H-valine incorporated into peptide products in translations containing IF1H, IF2H, IF3H, EF-TuH, EF-GH and 0.020 $A_{260}/\mu l$ ribosomes. Triangles: translations were started by mixing preincubated initiation components with preincubated elongation components. Squares: translations were started by transfering the translation mix from 0° C. to 37° C. Aliquots were terminated with NaOH at the indicated times beginning at 1 min. Peptide product d.p.m. was calculated by subtracting d.p.m. obtained in aliquots terminated before 37° C. incubation. Individual data points from representative experiments are plotted, with variations estimated to be less than 20%. A tangent line to the preincubation reaction curve is drawn to estimate the steady state rate.

As shown in FIG. 4, reconstitution of oligopeptide synthesis with all of the components shown in FIG. 2 using 3× salt-washed ribosomes and the MTV mRNA (FIG. 3) results in the synthesis of fMTV, as judged by the incorporation of $^3$H-labeled valine into the isolated peptide products. When the time course of synthesis is begun by combining a preincubated initiation mix with a preincubated elongation factor mix (triangles in FIG. 4; see legend), there is a rapid initial burst of product synthesis within the first minute and a slower rate of synthesis at steady state. Without the 10 minute preincubations (squares in FIG. 4; see legend), there is little product synthesis within the first minute, and synthesis is fairly linear with time (see also FIG. 7).

Figure 5:
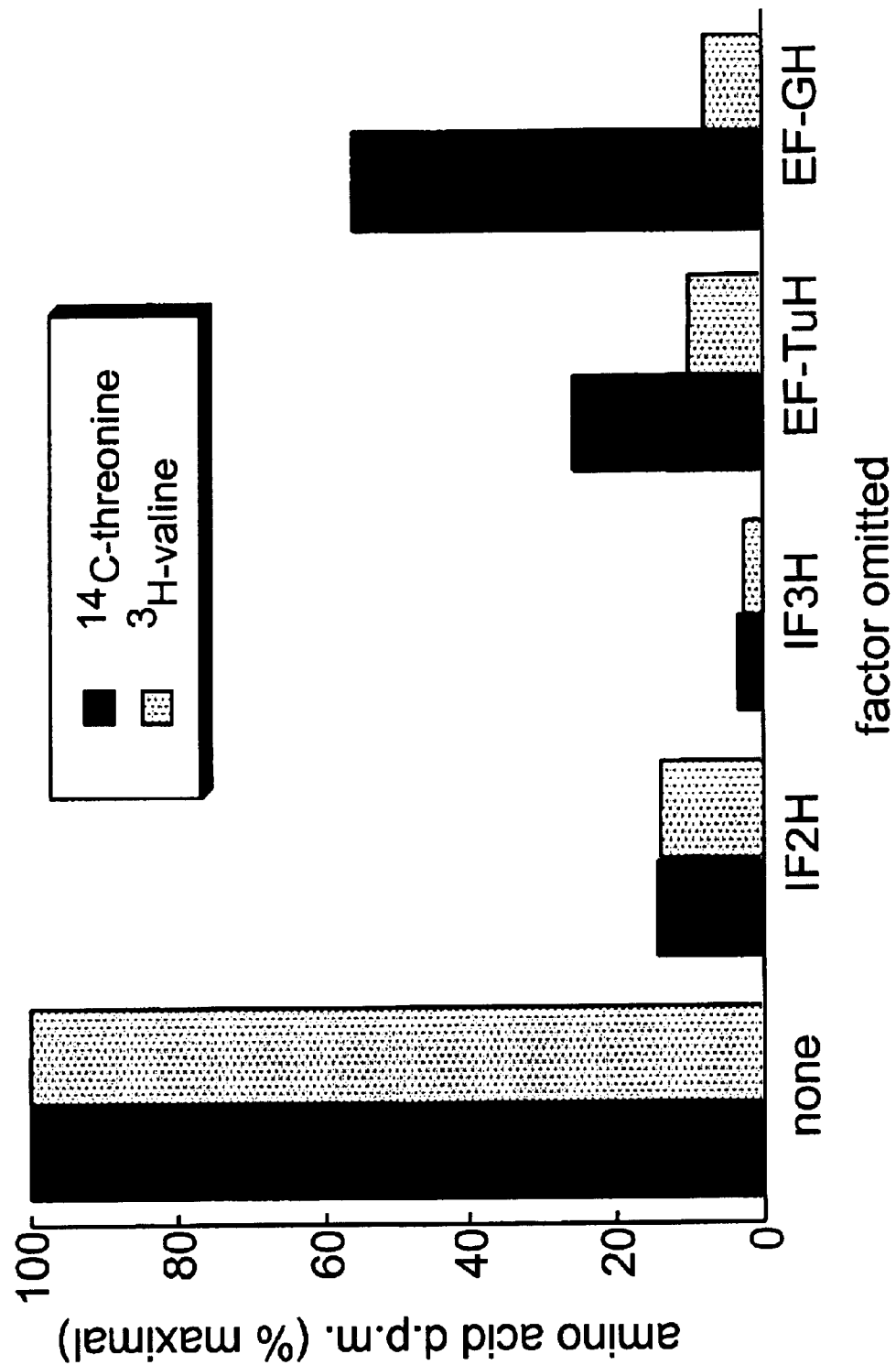
FIG. 5. Translation factor dependencies in the purified translation system with mRNA MTV. Light bars: $^3$H-valine incorporated into peptide products (a measure of fMTV) shows strong dependencies on IF2H, IF3H, EF-TuH and EF-GH (IF1H was omitted from these translations; see Materials and Methods). Dark bars: $^{14}$C-threonine incorporated into the same products (a combined measure of fMT and fMTV). Peptide synthesis in a 30 minute translation started by transfer from 0° C. to 37° C. was calculated by subtracting d.p.m. obtained in a control reaction lacking mRNA (1.3% of maximal d.p.m.) from total d.p.m. The maximum concentration of synthetic product obtained was 0.12 $\mu M$ for both T and V.

FIG. 5 illustrates the dependence on each factor necessary for in vitro translation (IF1 was omitted in this experiment), based on the incorporation of $^{14}$C-labeled threonine and $^3$H-labeled valine into peptide products. The complete system yielded peptide products with a threonine/valine (T/V) ratio of 1.0, as expected for fMTV synthesis. Omission of any one factor dramatically reduces fMTV synthesis (FIG. 5), giving dependencies comparable to those reported for the native factors (Robakis et al. (1981) *Proc Natl Acad Sci USA* 78, 4261–4; Cenatiempo et al. (1982) *Arch Biochem Biophys* 218, 572–8). The omission of translation factor EF-GH switched translation from tripeptide synthesis to fMT dipeptide synthesis (FIG. 5), consistent with the known primary role of EF-G in translocation. Although synthesis of dipeptides does not require addition of IF1 (Robakis et al. (1981) *Proc Natl Acad Sci USA* 78, 4261–4), and although the inclusion of IF1H in our translations does not lead to a dramatic increase in overall yield, IF1H does stimulate the rate of fMTV synthesis 2.5 fold during the first few minutes of translations performed without preincubation (data not shown), consistent with previously reported studies with native IF1 (Robakis et al. (1981) *Proc Natl Acad Sci USA* 78, 4261–4). Thus, the translation results confirm and extend the findings from the initiation assay (Table 1). Additional control translations omitting other macromolecular components of the translation system give the expected dependencies (see Materials and Methods). Ribosomes washed only once gave poor factor dependencies in translation assays of the type illustrated in FIG. 5 (data not shown).

Figure 6:
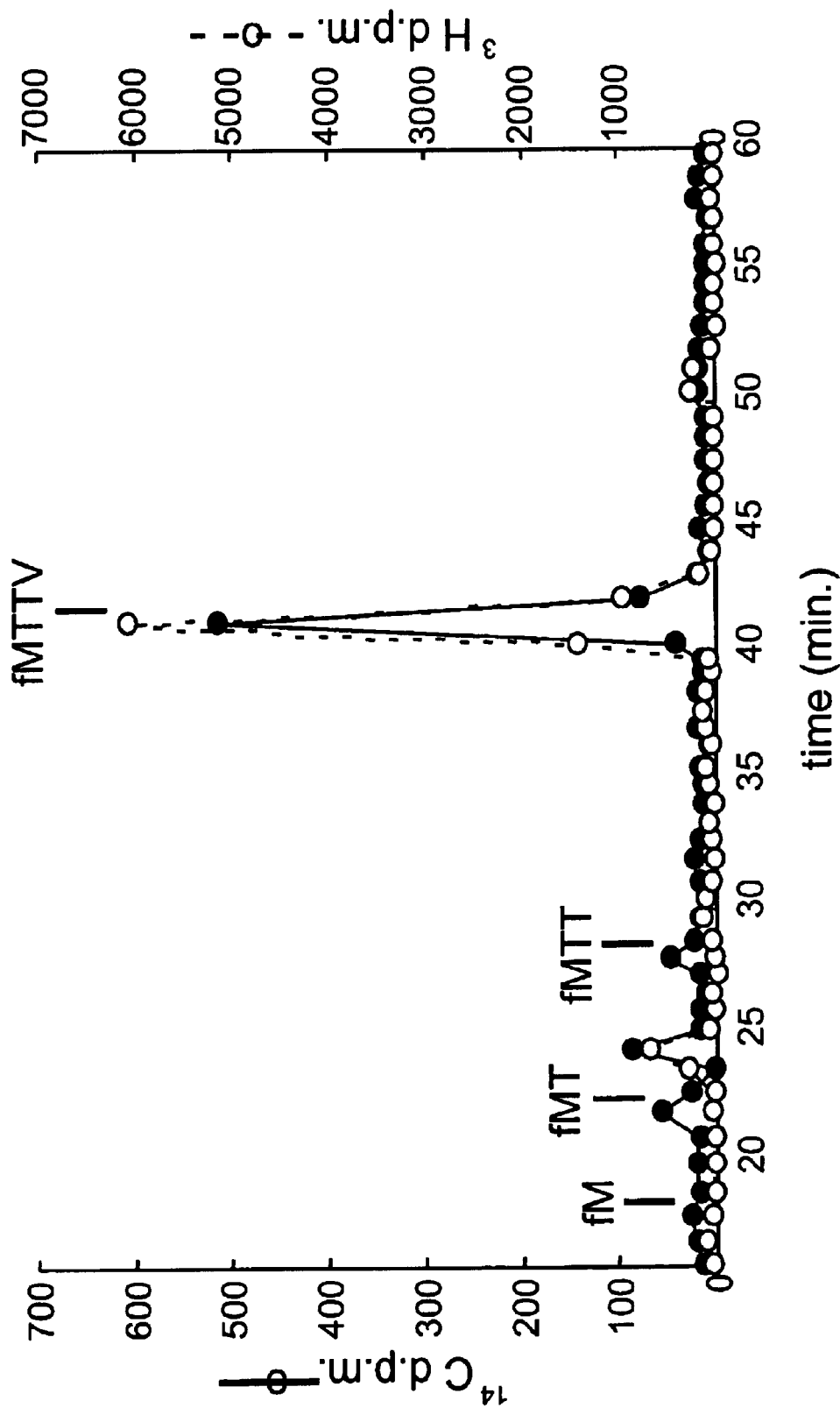
FIG. 6. HPLC analysis of products produced from the MTTV mRNA template. The peptide products of a dual-labeled translation were first released from the tRNAs with base and then mixed with unlabeled marker peptides. The mixture was acidified, microcentrifuged to remove insoluble material, and microcentrifuged through a 10 kD filter before injection for analysis (see Materials and Methods). The elution positions of marker peptides are indicated above the chromatogram. Filled circles: $^{14}$C-threonine total d.p.m. Open circles: $^3$H-valine total d.p.m. in the same fractions. The amount of product synthesized was 2.1 pmol in 30 $\mu l$ (70 nM).

Tetrapeptide synthesis. We next investigated the suitability of this system for the synthesis of tetrapeptides to show that all steps of initiation and elongation could occur in a highly purified system. In contrast to tripeptide synthesis, tetrapeptide synthesis is not possible without dissociation of deacylated tRNA from the exit site of the ribosome(Wilson and Noller (1998) *Cell* 92, 337–49). Using a template encoding the tetrapeptide fMTTV (FIG. 3), synthesis of dual-labeled products was assessed by reversed phase HPLC (FIG. 6). Radioactive peptide products were identified based on their co-migration with chemically synthesized non-radioactive standards. The predominant radioactive peak in the peptidyl separation range corresponds to the fMTTV tetrapeptide (80–85% of the $^{14}$C or $^3$H radioactivity in this range) with a T/V ratio close to that expected. Two minor peaks correspond to the pausing or premature termination products fMT and fMTT, with no $^3$H incorporated, as expected. fMT (SEQ ID NO: 15) and fMTT (SEQ ID NO: 16) together contain 12% of the $^{14}$C radioactivity in the peptidyl range, equivalent to 20% of the combined products fMTTV, fMTT and fMT on a molar basis. The remaining two minor peaks (at 24 and 50 min.) presumably correspond to derivatives of fMTTV (e.g. methionine oxidation products or unformylated peptide), other peptidyl products and/or non-peptide radioactive contaminants. Thus, the purified his-tagged tetrapeptide translation system is predominantly, but not completely, processive with yields of full-length tetrapeptide products equal to 80% of the peptide products. This detailed analysis demonstrated much higher processivity in absence of added EF-P, W and rescue than that previously reported (Ganoza et al. (1985) Proc Nail Acad Sci USA 82, 1648–52).

Further examples of peptides synthesized efficiently by our in vitro translation system are shown in the Table 2. The synthesis of the expected 7-mer full-length fMTTTTTV peptide (SEQ ID NO: 44), generated from mRNA template product (SEQ ID NO. 43) was highly processive because a predominance of premature termination products would have resulted in a much higher T/V ratio than the measured value of 6.4.

Figure 7:
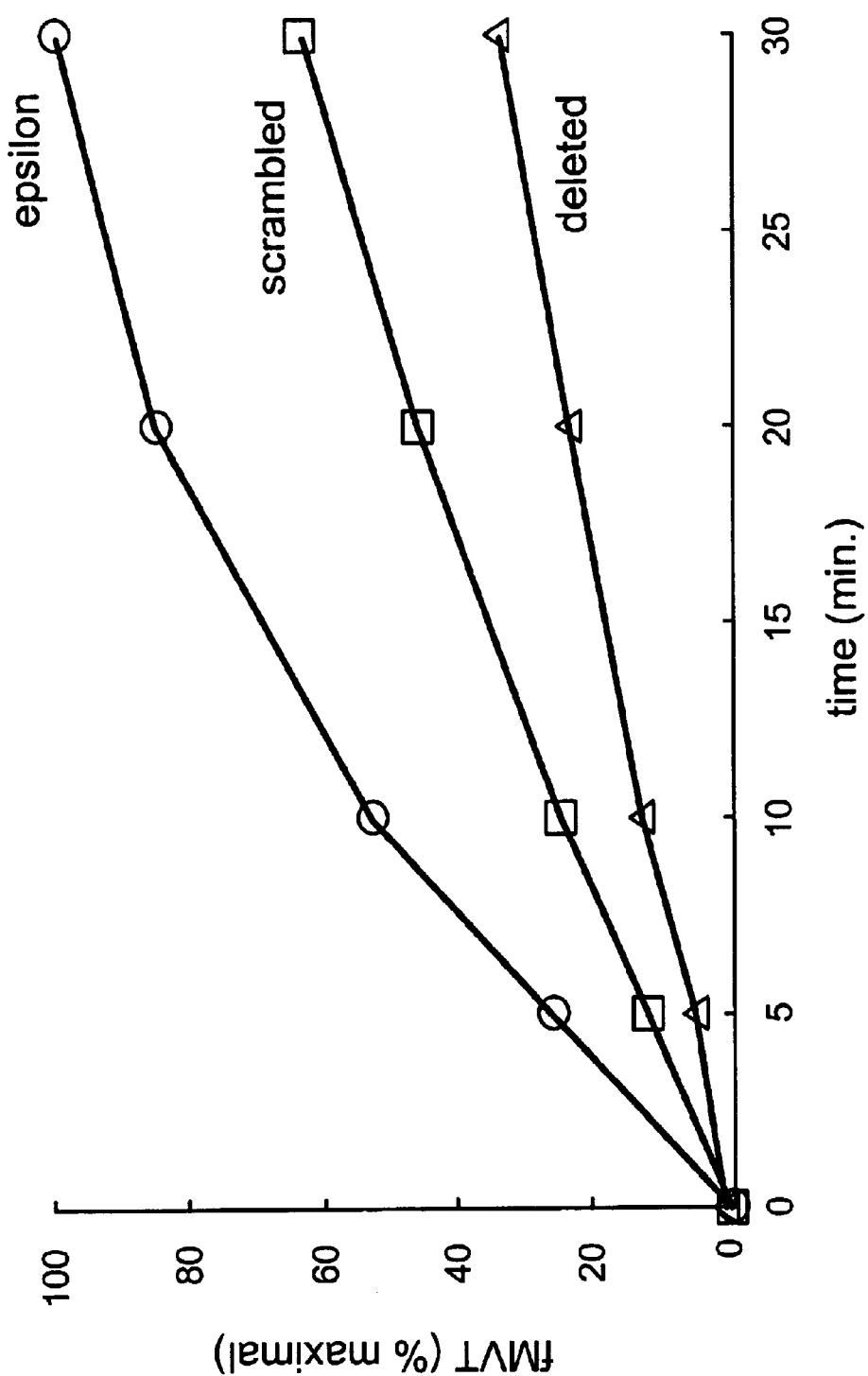
FIG. 7. Inclusion of the epsilon sequence enhances the synthesis of oligopeptide product in a purified translation system. Comparison between rates of fMVT synthesis from mRNAs MVT (circles), scrambled-epsiMVT (squares) and ΔepsiMVT (triangles). Dual-labeled translations containing IF1H, IF2H, IF3H, EF-TuH and EF-GH were analysed as described in FIG. 5. The maximum concentration of oligopeptide synthesized in 30 minutes was 0.25 μM using 0.5 μM of each aminoacyl tRNA.

Effects of upstream mRNA mutations on oligopeptide synthesis. An unresolved question in translation initiation is the influence of the epsilon sequence in a purified system. Therefore, the effect of scrambling or deleting epsilon was determined using the mRNAs scramble-epsiMVT and delta-epsiMVT (FIG. 3) and template concentrations (1 μM) that are saturating for mRNA MVT (data not shown) under conditions where initiation should be rate-limiting (see FIG. 4). FIG. 7 shows that scrambling of the U-rich epsilon sequence results in decreased fMVT synthesis, and deletion of the sequence results in a five-fold decrease in the initial rate of product synthesis. Concentrations of mRNA delta-epsiMVT up to 14 fold higher failed to substantially increase the yield of fMVT (data not shown).

Figure 8:
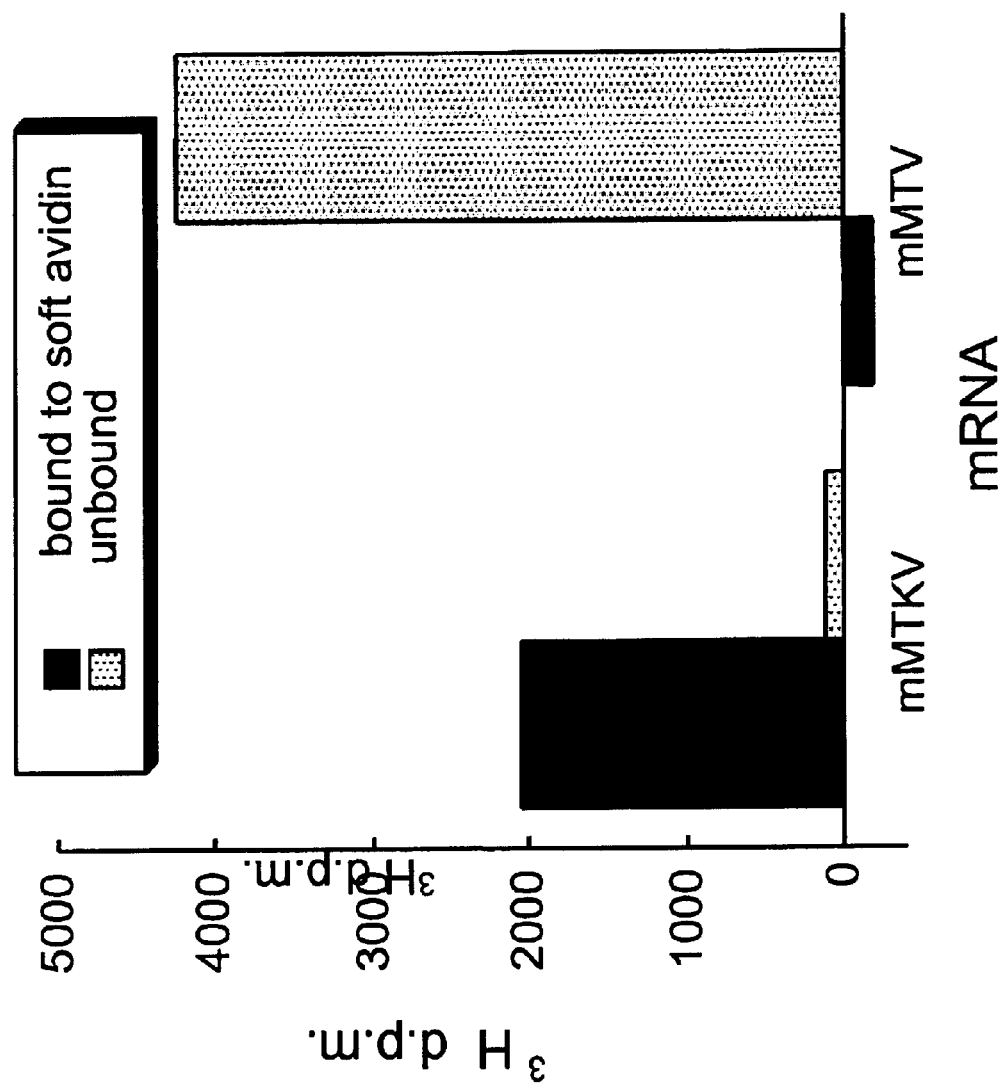
FIG. 8. Synthesis and selection of peptides containing an unnatural amino acid using the purified his-tagged translation system. Translation mixes containing biotin-labeled-lys-tRN$^{lys}$, fmet-tRNA$_i^{fmet}$, thr-tRNA$_3^{thr}$ and $^3$H-val-tRNA$_1^{val}$ substrates and either mRNA MTKV or MTV (see FIG. 3 for translation products) were incubated at 37° C. for 30 minutes. The peptides and amino acids were released from the tRNAs and ribosomes with base, neutralized, and the mixtures incubated with soft avidin beads to bind biotin-containing molecules. The beads were washed four times to remove unbiotinylated molecules before counting bound $^3$H (dark bars: a measure of products containing biotin-labeled-lysine covalently linked to $^3$H-valine). The pooled washes were filtered, acidified, and passed through a cation exchange column to count unbound $^3$H (light bars: a measure of formylated peptide products containing $^3$H-valine without biotin-labeled-lysine or lysine). Bound and unbound $^3$H d.p.m. are plotted after subtracting d.p.m. obtained in a control reaction lacking mRNA (23% and 15% of maximal bound and unbound d.p.m., respectively). When biotin-labeled-lys-tRNA$^{lys}$ is omitted from a translation of mRNA MTKV, binding of $^3$H to the beads is not observed (not shown).

Incorporation and selection of an unnatural amino acid. Our tetrapeptide synthesis format is directly amenable to many types of initiation and elongation assays, including the testing of unnatural amino acids for incorporation by ribosomes for mechanistic or selection experiments. For example, translation of mRNA mMTKV (FIG. 3) using the substrates $^3$H-fmet-tRNA$_i^{fmet}$, $^{14}$C-thr-tRNA$_3^{thr}$, biotin-labeled-lys-tRNA$^{lys}$ (Promega) and $^3$H-val-tRNA$_1^{val}$ yielded peptide product containing both biotin and $^3$H-valine (fM-T-bK-V), as judged by product copurification with soft avidin beads (Promega) in a manner dependent on a lysine codon in the mRNA and on biotin-labeled-lys-tRNA$^{lys}$ (FIG. 8). This experiment demonstrates that the purified translation system is capable of incorporating an easily selectable, large, unnatural amino acid.

Given that the $K_d$ of the biotin-avidin interaction ($10^{-15}$ M) is one of the lowest known for any ligand bound non-covalently and monovalently to its target, it is expected that our synthesized biotin-containing peptidomimetic has an affinity for one of its cognate targets (avidin) that is greater than the affinity of any natural peptide of similar length for its cognate target. Given that the identification of very high affinity ligands is most desirable in library screening experiments, the potential advantage of a ligand-screening method that can use unnatural amino acids over a method that can only use natural amino acids is illustrated by the above example of our peptide containing biotinyl-lysine.

Figure 9:
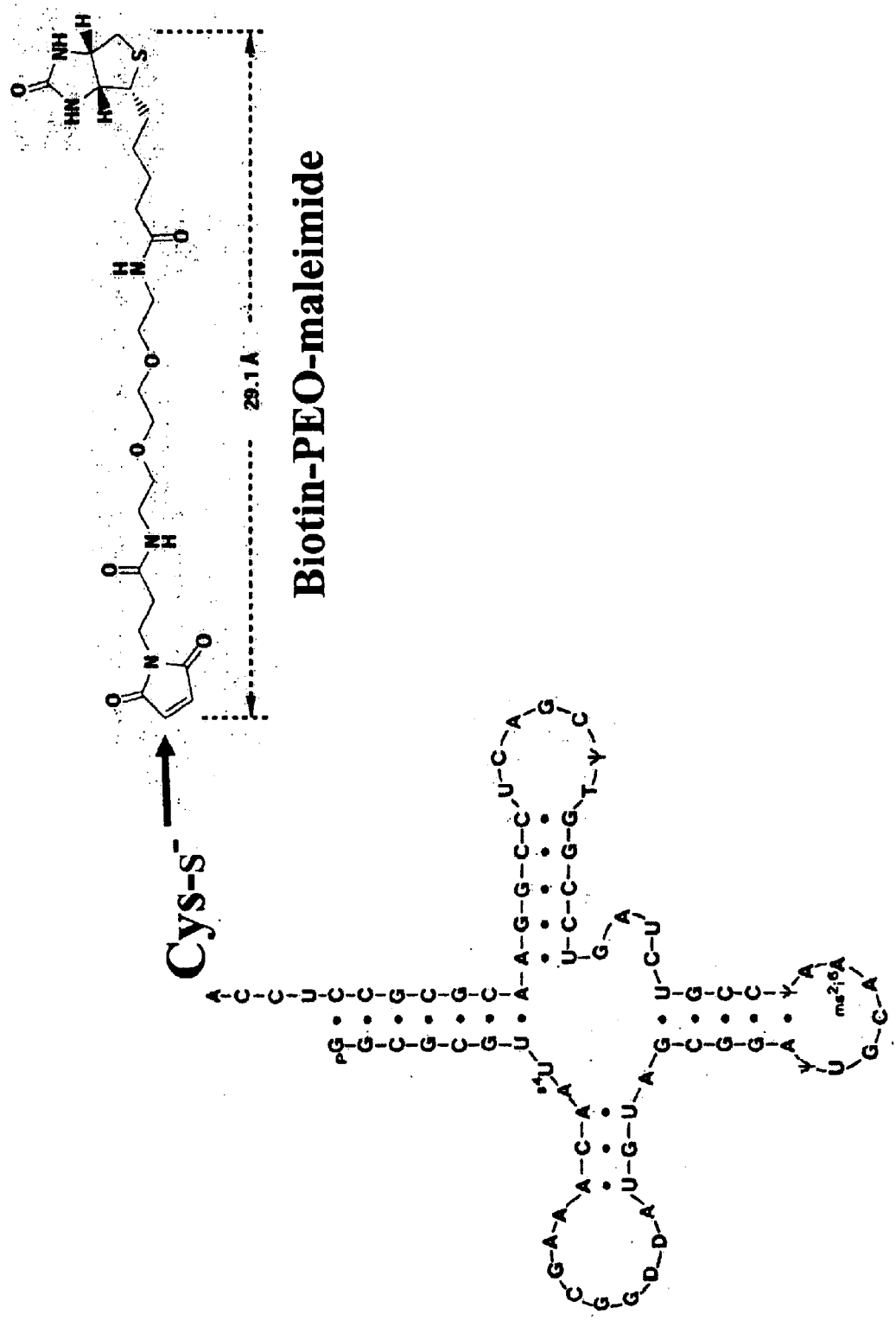
FIG. 9. Chemical biotinylation of Cys-tRNA$^{Cys}$ (SEQ ID NO: 17).
Figure 10:
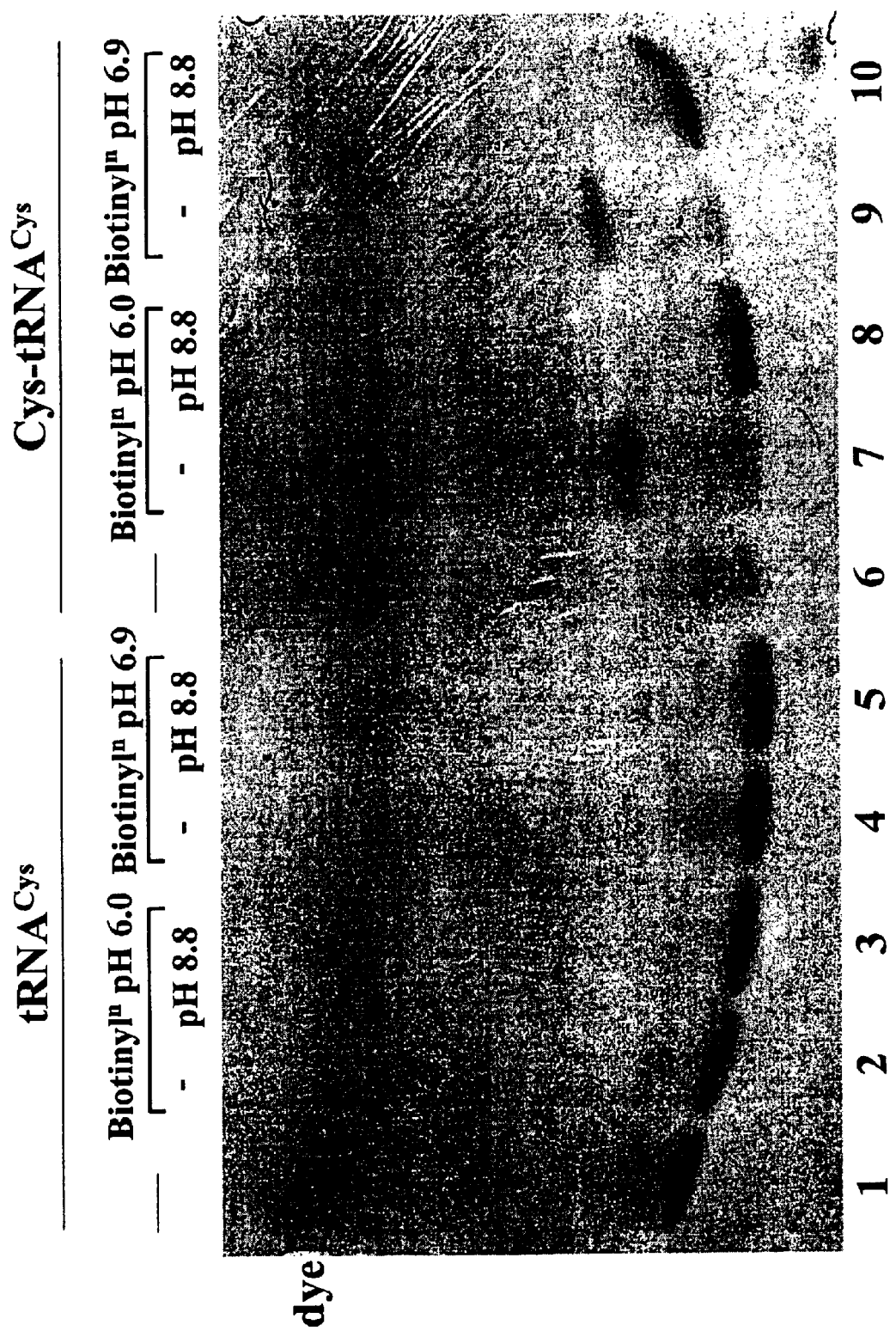
FIG. 10. Purification of biotinyl-Cys-tRNA$^{Cys}$. Biotinyl-Cys-tRNA was electrophoresed as in FIG. 16 (see below), and the product purified by cutting out the appropriated band (i.e. the major band in lane 7 or 9) and elution at 4° C. Controls including +/- charging of the tRNA with Cys, +/- biotinylation (at either pH 6.0 or 6.9), and +/- subsequent hydrolysis of the aminoacyl linkage with Tris-HCl pH 8.8 (lanes 1–6,8,10) showed that biotinylation was specific to the Cys, and that Cys-tRNA did not comigrate with biotinyl-Cys-tRNA.
Figure 11:
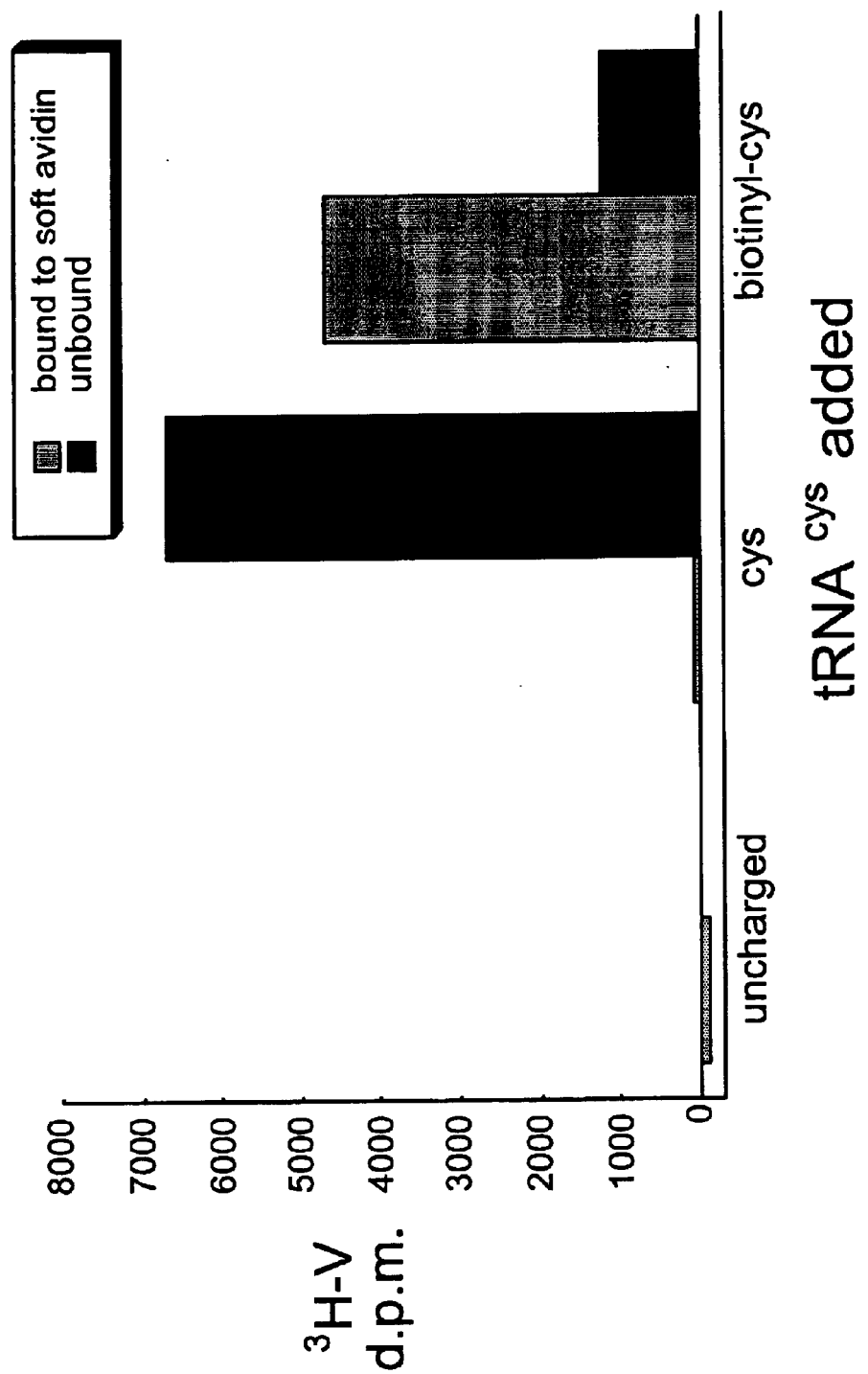
FIG. 11. Incorporation of purified biotinyl-Cys into fM-T-bC-V (SEQ ID NO: 20) peptidomimetic using the purified system. Translations contained mMTCV, tRNAs charged with fM, T, V, and either uncharged, Cys-charged or purified biotinyl-Cys-charged tRNA, with controls lacking mRNAs. Selection was with Soft Avidin as in FIG. 8. Incomplete binding of $^3$H-peptide with biotinyl-Cys substrate was likely due to the low affinity of Soft Avidin (an avidin derivatised to have a much higher K$_d$ of approximately 10$^{-7}$M) for peptides containing a single biotin.
Figure 12:
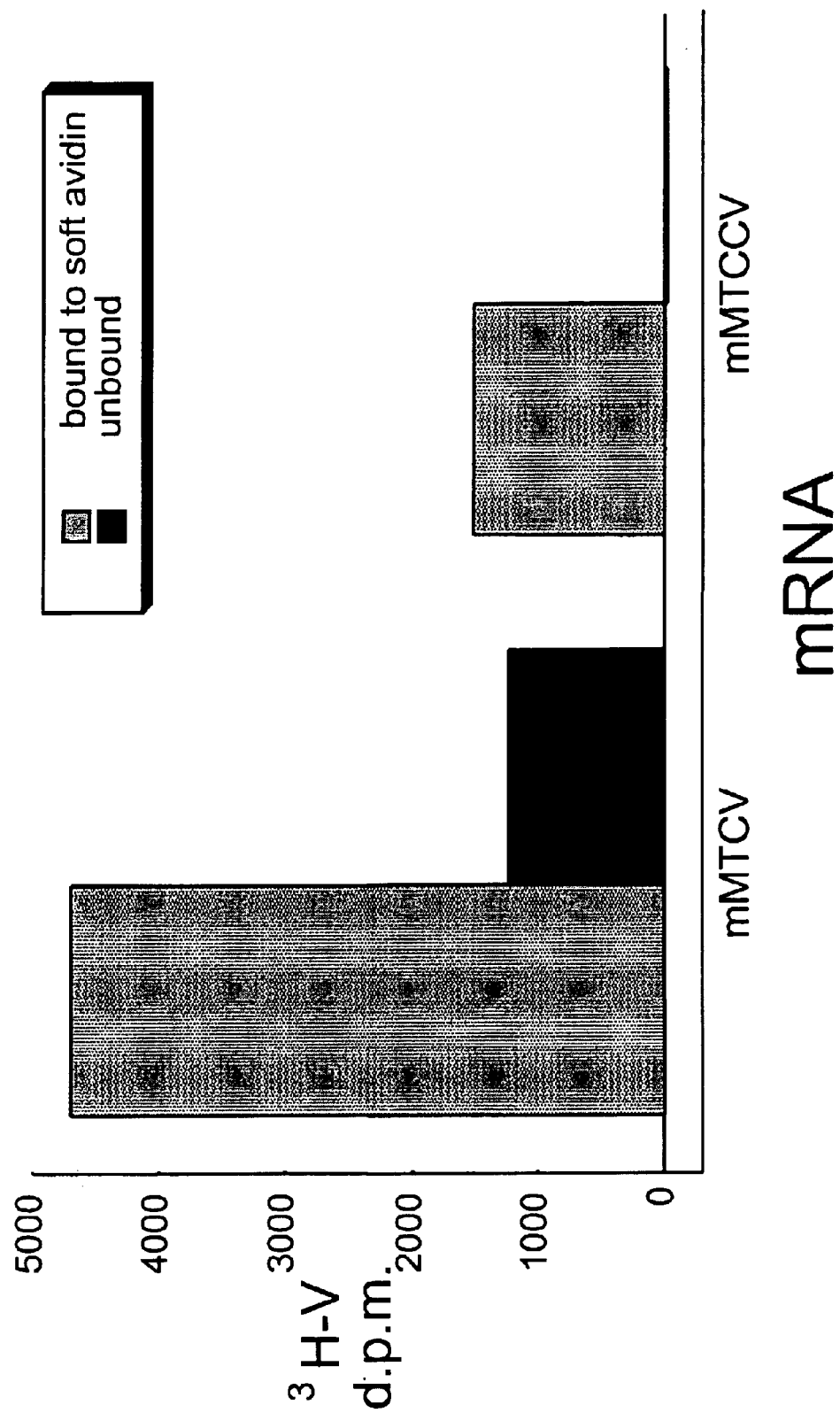
FIG. 12. Assay for incorporation of adjacent large unnatural amino acids into fM-T-bC-bC-V peptidomimetic (SEQ ID NO: 21). The experiment was carried out as in FIG. 11. Note binding by Soft Avidin was complete for fM-T-bC-bC-V but incomplete for fM-T-bC-V, as expected for the much higher affinity for peptides containing more than one biotin SEQ ID NOS: 18 and 19 correspond to mMTCV and mMTCCV, respectively.

An analogous experiment to that of FIG. 8 has also been performed with biotinyl-Cys-tRNA$^{Cys}$, except that, in this case, the biotinyl-aminoacyl-tRNA species used had been purified by alternative procedures. Pure tRNA$^{Cys}$ isoacceptor (Subriden RNA) was charged with Cys using a tRNA-free crude synthetase extract, the resulting Cys-tRNA$^{Cys}$ was chemically labelled with biotin (FIG. 9) by minor modification of a published method (Ohtsuka et al. (1997) Nucleic Acids Symp. 37, 125–126), biotinyl-Cys-tRNA$^{Cys}$ was gel-purified (FIG. 10), and then biotinyl-Cys (abbreviated bC) was incorporated into peptidomimetics and bound to Soft Avidin (FIGS. 11 and 12). The results in FIG. 12 suggest that our in vitro system may be able to incorporate specifically two adjacent large unnatural amino acids.

Figure 13:
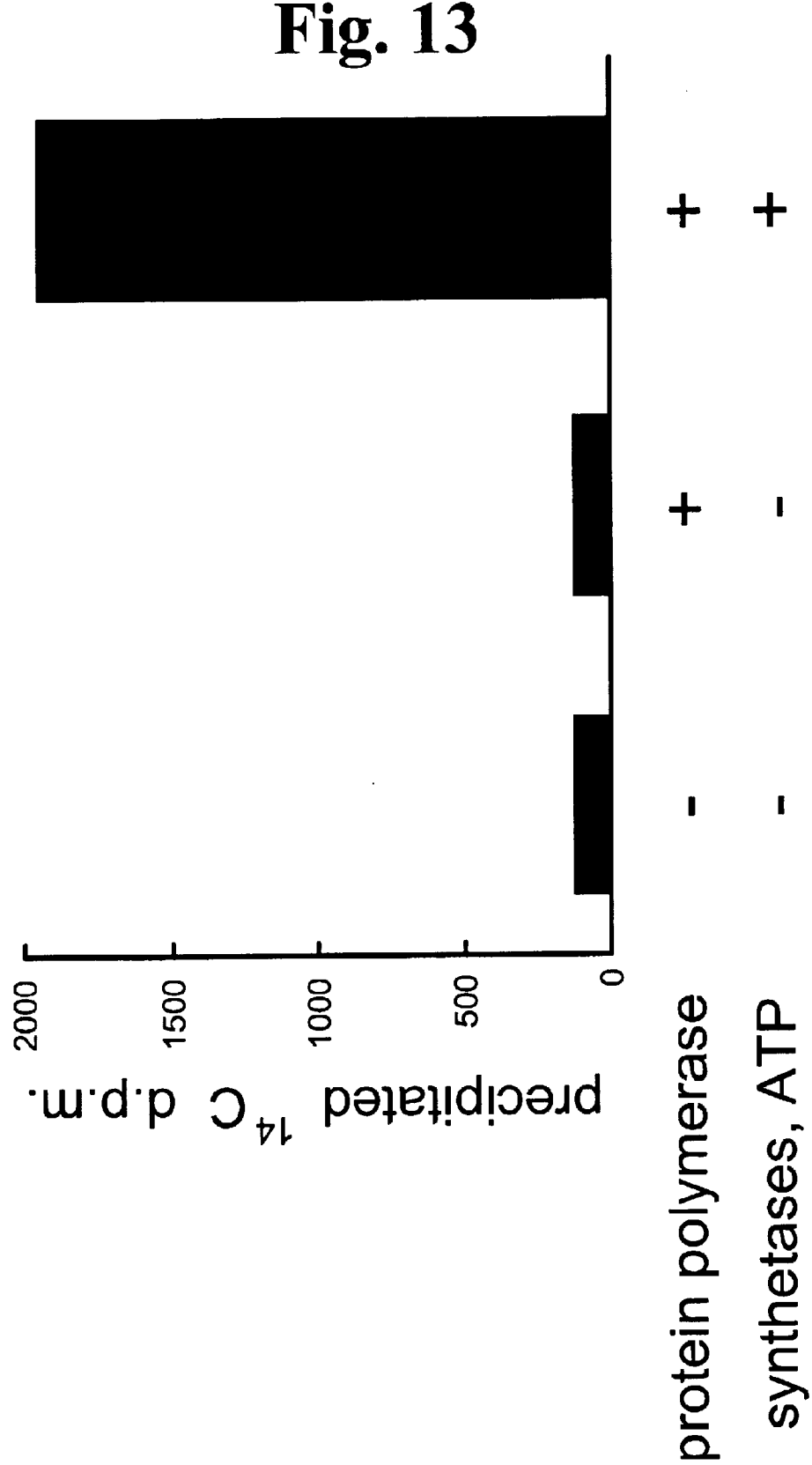
FIG. 13. Assay of our pure translation system ("protein polymerase") for charging activity (measured by TCA precipitation) with total tRNA and a mixture of fifteen different $^{14}$C-labelled amino acids (New England Nuclear). The added synthetases consisted of a tRNA-free crude aminoacyl-tRNA synthetase cell extract.

Importantly, the translation with uncharged tRNA$^{Cys}$ in FIG. 11 gave no incorporation of $^3$H, demonstrating that the purified system lacked charging activity and was specific for exogenous substrate. This has also been demonstrated for translations "seeded" with uncharged tRNA$^{Thr}$ or uncharged tRNA$^{Val}$ (not shown), as expected for an aminoacyl-tRNA-synthetase-free pure system. Given that the synthetases are amongst the most abundant proteins of E. coli and that ribosome preparations can be used for their purification (Ganoza et al. (1996) Biochemie 78, 51–61), additional experiments were performed to verify that our pure translation system lacked synthetase activity. FIG. 13 confirmed that our "protein polymerase" lacked contaminating aminoacyl-tRNA synthetases.

Figure 20:
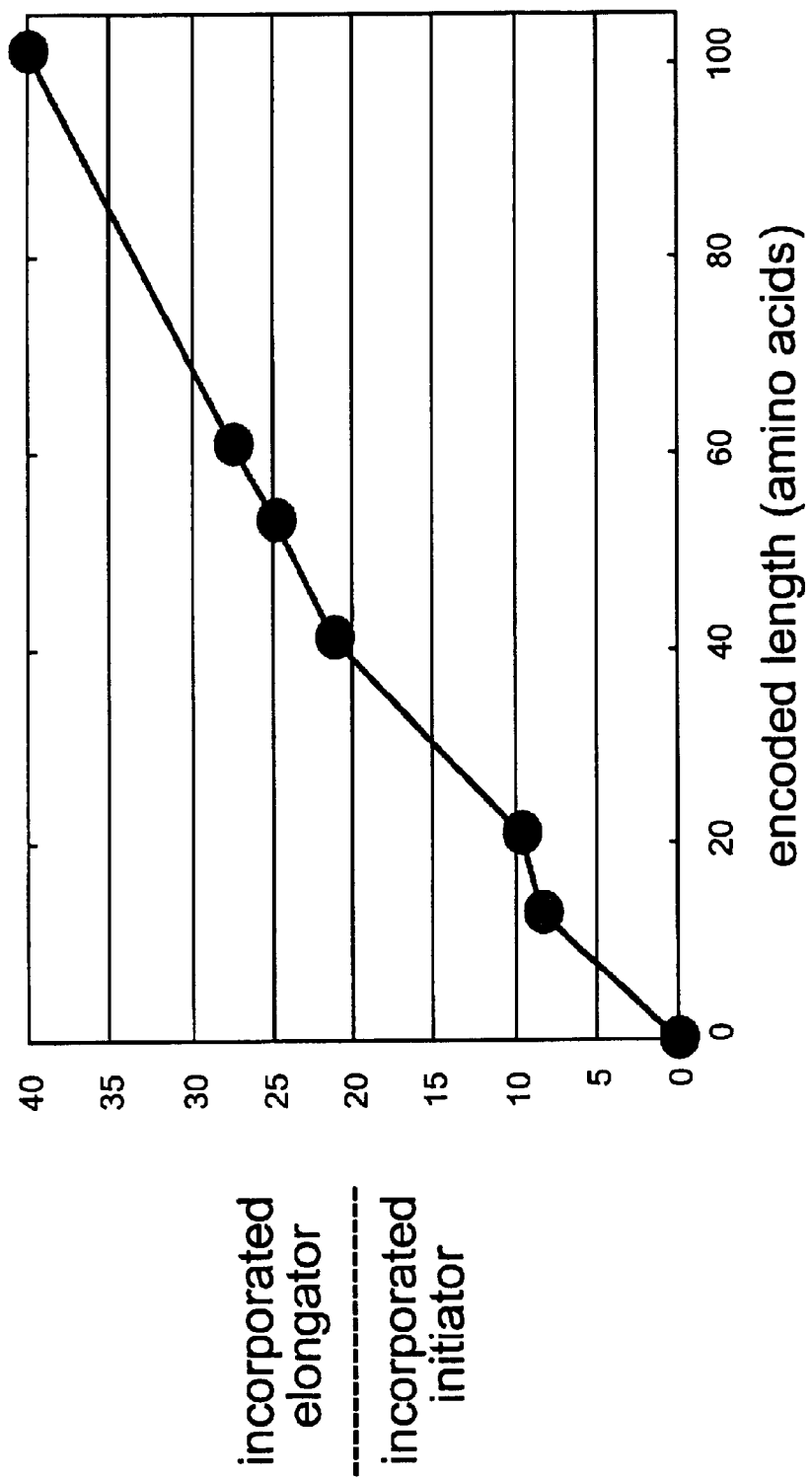
FIG. 20. Translation of spacer mRNAs of FIG. 19 using our purified system. The ratios of elongator valine ($^3$H-labelled) to initiator formylmethione ($^{35}$S-labelled) incorporated into peptide products was measured by analysis of TCA-precipitated products using a dual-labelled-d.p.m. counting program. The linear plot observed is that expected for high processivity.
Figure 21:
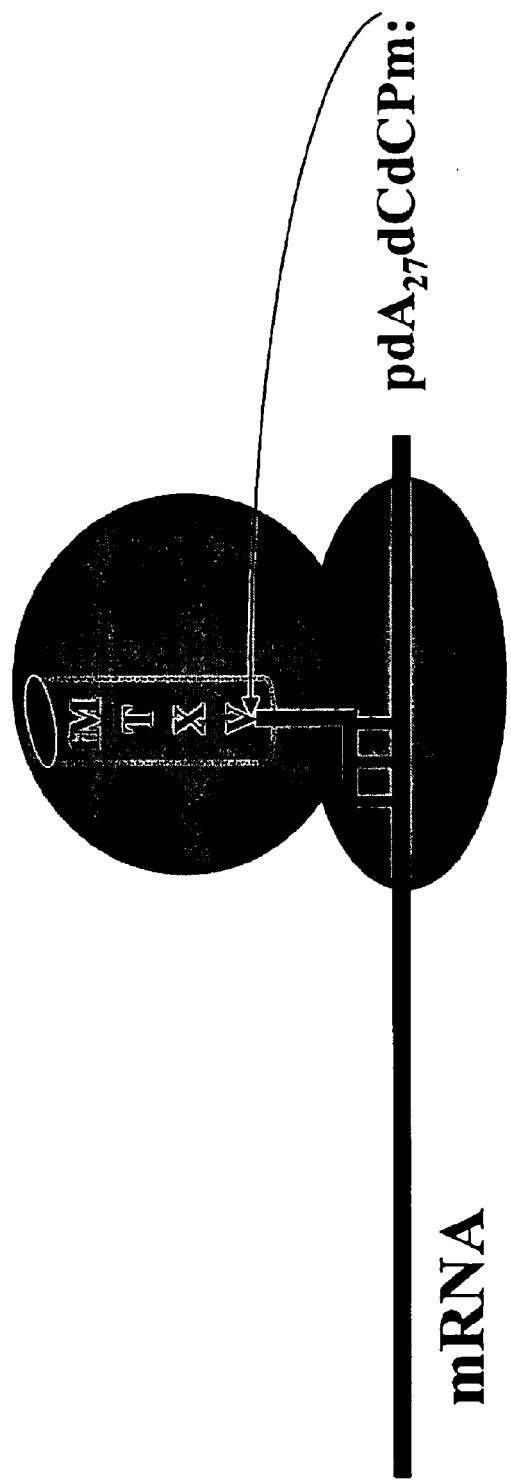
FIG. 21. Pure mRNA display. This is a pure version of the crude in vitro system (without living material) of Nemoto et al. (supra) and Roberts and Szostak (supra) based on that of Mattheakis et al.

Purification of peptide and peptidomimetic products. Several alternative methods (either non-denaturing or denaturing) standard in the art are available for the release of free peptides or peptidomimetics from peptidyl-tRNA, including, but not limited to, chemical hydrolysis with base (e.g. FIGS. 4–8), enzymatic catalysis by release factors (Table 3) or peptidyl-tRNA hydrolase enzyme (purified and used as in Karimi et al. (1998) J. Mol. Biol. 281, 241–252) and nucleophylic attack by the puromycin antibiotic or its derivatives (FIG. 21). Any of the numerous methods (either non-denaturing or denaturing) standard in the art for peptide or protein purification can be used for purification of peptide and peptidomimetic products, including, but not limited to, affinity purification using a solid support (e.g. using the interaction between soft avidin beads and biotin in FIGS. 8, 11 and 12), chromatography (e.g. using cation exchange chromatography in FIGS. 4 and 5, or reversed phase HPLC in FIG. 6), or precipitation from solution (e.g. using TCA in FIG. 20).

Despite the high demonstrated purity of our translation system (Table 1, FIGS. 1, 5, 11, and 13) and the apparent dispensability of EF-P, W and rescue for processive translation, additional experiments were performed to rule out the argument that one or more of these factors contaminates the ribosomes (see Background of the Invention). The published method for removing EF-P, W and rescue from ribosomes (Green et al. (1985) Biochem. Biophys. Res. Comm. 126, 792–798) is to pellet the ribosomes up to five times with an overnight wash in high salt (0.5–1 M) between each centrifugation (the more salt washes, the higher the purity of the ribosomes). Since our ribosomes had been pelleted four times with three high salt washes, our ribosomes should have a comparable purity to Ganoza's. Nevertheless, a different batch of ribosomes was prepared that incorporated an additional (fourth) high salt wash (the same total number as Ganoza's most highly washed ribosomes), and, in addition, the final 150 000 g centrifugation was split into two steps to remove easily pelleted material. In the first step, centrifugation was performed at the maximum speed for one minute, and the resulting pellet was discarded (this material was predominantly non-ribosomal based on a low absorbance at 260 nm). In the second step, the ribosomes from the supernatant were pelleted by extended centrifugation. The purity of these 4× washed ribosomes was demonstrated to be very high based on strong dependencies on translation factors for initiation and translation (assayed as in Table 1 and FIG. 5). As an additional control, all of our translation factors, which had previously been purified by Ni-affinity chromatography, were further purified individually by an additional gel-filtration chromatography step. The combination of these 4× washed ribosomes and Ni/gel-purified factors was found to be active and processive in synthesis of peptides as long as 101 amino acids (see FIG. 20 below), and the additional purification steps do not significantly affect our translations in comparison with the 3× washed ribosomes and Ni-purified factors. These studies confirm that our translation system is not dependent on EF-P, W and rescue.

Other embodiments of the invention are versions of our simplified purified translation system lacking EF-P, W and rescue in which one or more of the components have been substantially adjusted in concentration or even omitted entirely. For example, PEG is often omitted, resulting in only an approximately 25% decrease in yield, and efficient translation occurs without IF1 (Table 2; FIG. 5). Inclusion of our other standard translation initiation and elongation factors, although important for efficiency under commonly used conditions, is not essential for product synthesis (FIG. 5). Indeed, efficient translation in model systems is possible without any of the bacterial initiation factors (i.e. IF1, IF2 and IF3) if they are substituted by higher concentrations of cations (e.g. $Mg^{2+}$ or polyamines; Wagner et al. (1982) Eur. J. Biochem. 122, 193–197).

Still further embodiments of the invention are versions of our simplified purified translation system described in detail above in which one or more of other purified macromolecules and small molecules known to be involved in, or to stimulate, translation have been added. These include, but should not be limited to, cellular total tRNA or fractions thereof, cellular total aminoacyl-tRNA or fractions thereof, synthetic charged or uncharged tRNAs, one or more of the aminoacyl-tRNA synthetases for each of the twenty natural amino acids, Met-tRNA$_f^{fMet}$ formyltransferase (also called methionyl-tRNA transformylase), $N^{10}$-formyl THF synthetase and THF derivatives, elongation factor Ts (see Materials and methods), release factors (RF1, RF2, RF3, and RRF or RF4), DNA templates and RNA polymerases for coupled transcription and translation, RNA helicases, chaperones (Hardesty et al. (1999) Curr Opin Struct Biol 9, 111–4), ribosomes purified by different procedures (including separation into subunits) such as sucrose-density-gradient-centrifugation, components of "polymix buffer" including polyamines (Jelenc and Kurland (1979) PNAS 76, 3174–3178) and energy-related systems that differ from our pyruvate kinase system such as those with creatine kinase, myokinase and/or pyrophosphatase (Shimizu et al. (2001) Nat. Biotech. 19, 751–755). Addition of, or substitution with, untagged or mutated versions of natural components, such as our recombinant untagged IF1, IF2 and IF3 (see Materials and Methods) or an EF-Tu derivative with improved incorporation of unnatural amino acids, or altered ribosomes is also possible in a pure translation system.

For example, our simplified purified translation system, such as that of FIGS. 6 and 11, is stimulated by addition of bacterial release factors (Table 3). The addition of synthetases to our translations, such as those for Thr and Val, together with amino acids Thr and Val and ATP, enabled generation of, and regeneration of, the respective aminoacyl-tRNAs from the respective uncharged tRNAs (not shown).

The addition of DNA template, NTPs and RNA polymerase enabled coupled transcription and translation (Table 2). Addition of other molecules, such as polyethylene glycol, also proved stimulatory (not shown). Total aminoacyl tRNA, isolated from cells by acid phenol extraction (Varshney et al. (1991) J. Biol. Chem. 266, 24712–24718; see also FIG. 16, lane 2 below), is also active in our purified translations. An alternative approach for substrate preparation is to charge deacylated total tRNA in vitro before translation (Green et al. (1985) Biochem. Biophys. Res. Comm. 126, 792–798). The latter approach has the advantage of being more readily suitable for the selective depletion or inactivation of certain tRNA isoacceptors (e.g. using isoacceptor-specific DNA oligos and RNAse H (Kanda et al. (1998) FEBS Lett. 440, 273–276)) to allow incorporation of radiolabelled or unnatural amino acids charged on appropriate tRNAs.

Six months after our Provisional Patent Application, further evidence was published (Shimizu et al. (2001) Nat. Biotech. 19, 751–755; incorporated by reference herein) for the dispensibility on EF-P, W and rescue in a purified translation system. Their version of our system, in contrast to our preferred system, contained aminoacyl-tRNA synthetases. Translation was reconstituted efficiently with recombinant versions of all of the well-characterized translation factors and synthetases, without added EF-P, W, W2 and rescue. However, the ribosomes were prepared by a different method from Ganoza's and ours (using less salt washing), and the dependencies on three of the twenty different synthetases were incomplete, raising the possibility of contamination by EF-P, W, W2 and rescue. Nevertheless, strong dependencies on most of the factors were reported, as was efficient synthesis of several proteins.

A stop codon was recruited to incorporate valine efficiently using a chemically charged suppressor tRNA mutated to avoid synthetase recognition, but, contrary to claims in the publication, incorporation of an unnatural amino acid was not tested (Shimizu et al. (2001) Nat. Biotech. 19, 751–755). Potentially, the incorporation of an unnatural amino acid by a suppressor tRNA in this version of our system has the advantage that competition with certain termination factors can be circumvented by simply omitting them. However, like existing systems for unnatural amino acid incorporation that use crude extracts (see Background of the Invention), this strategy is likely to be restricted to incorporation of a single type of unnatural amino acid per protein at only one of the three termination codons (the UAG codon) because of competition from natural amino acids at sense codons catalysed by the tRNA charging and proofreading activities of the twenty different added aminoacyl tRNA synthetases, and because an attempt to use a second termination codon (UGA) failed due to readthrough by the ribosome (Cload et al. (1996) Chem. and Biol. 3, 1033–1038). Potentially, to allow incorporation of multiple different unnatural amino acids in such a system, the suppressor anticodon could be mutated to recognise certain sense codons (by base pairing), and competition at those codons potentially could be circumvented by omitting the cognate natural amino acids and synthetases. However, for most of the twenty synthetases, the anticodons of their cognate tRNA isoacceptor substrates are the most important recognition elements, so alterations in the anticodon of the suppressor tRNA are likely to lead to unwanted synthetase recognition (sometimes with an unpredictable specificity of cross-recognition) and therefore proofreading and/or charging with a natural amino acid (Giege et al. (1998) Nucleic Acids Res. 26, 5017–5035). In addition, tRNA mutations designed to prevent synthetase recognition may also decrease the efficiency of EF-Tu and/or ribosome recognition, thereby decreasing the efficiency of incorporation of the carried amino acid. Because of these difficulties with synthetase recognition and also the difficulties associated with over-expressing as many as twenty different synthetase proteins (Swartz (2001) *Nat. Biotech.* 19, 732–733), we preferred a synthetase-free translation system for our tests with unnatural amino acids.

Figure 16:
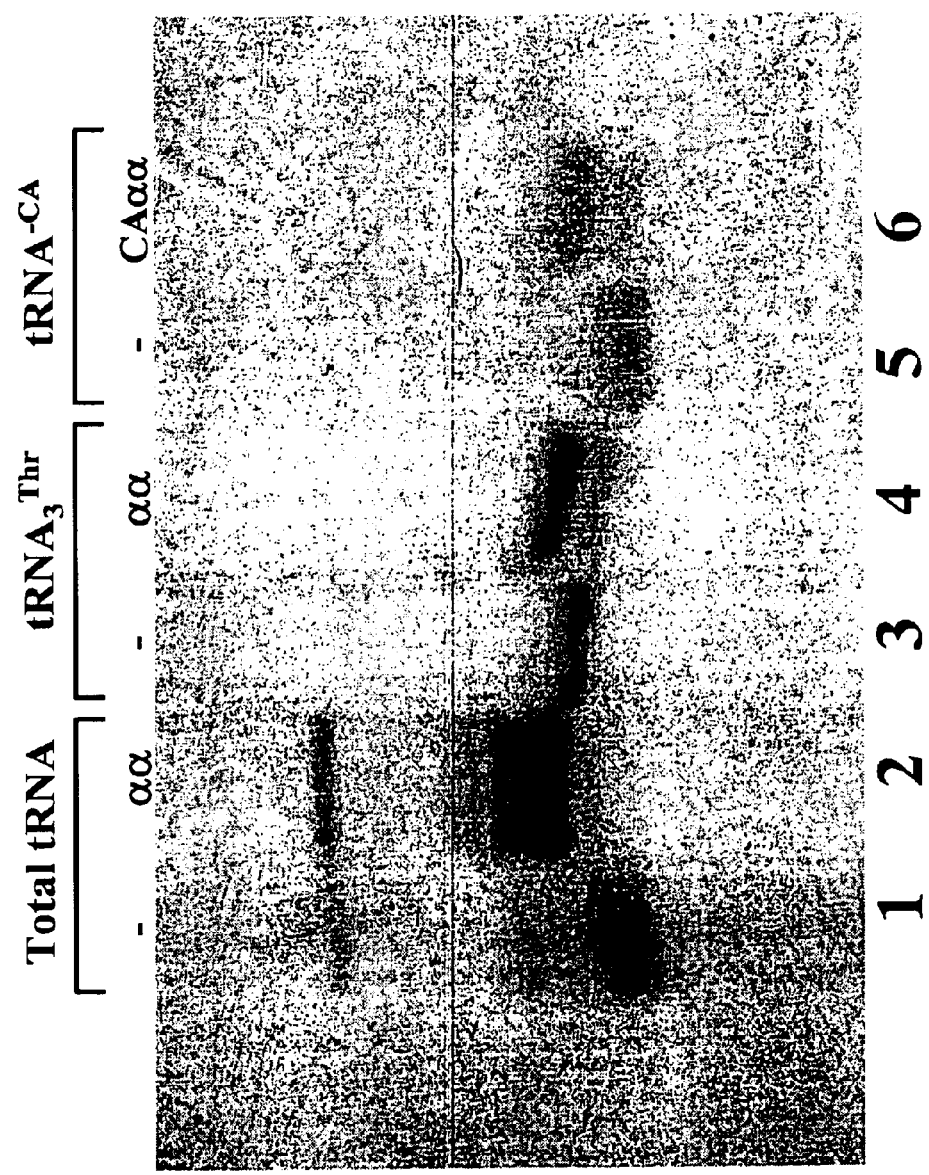
FIG. 16. Acid/urea polyacrylamide gel electrophoresis (Varshney et al. (1991) *J. Biol. Chem.* 266, 24712–24718) of uncharged tRNAs (lanes 1, 3 and 5) and aminoacyl tRNA substrates (lanes 2, 4 and 6). In this gel system, the observed mobility of the free RNA species (lanes 1, 3 and 5) is retarded by aminoacylation (lanes 2, 4) or by ligation of an aminoacylated CA dinucleotide (lane 6).
Figure 17:
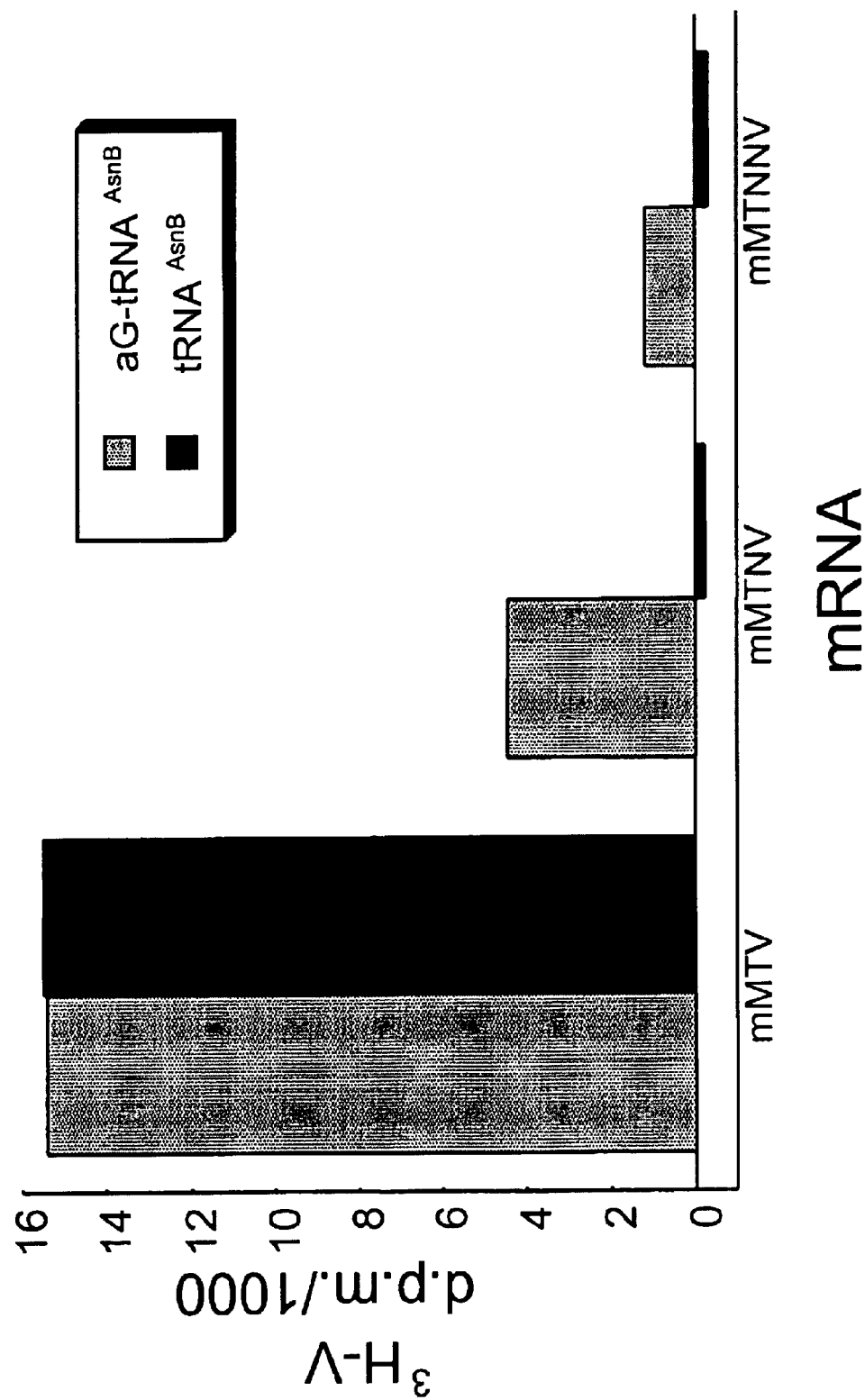
FIG. 17. A generalizable approach for the selective incorporation of adjacent aG amino acids into peptidomimetics. The experiment was carried out as in FIGS. 8 and 11, but without a selection step. Note that tRNA$^{Asn}$(N) is abbreviated here as tRNA$^{AsnB}$ for Asn-based.

We have tested incorporation of several unnatural amino acids using chemically charged tRNAs. The first step was to construct a synthetic elongator tRNA lacking the terminal CA dinucleotide to allow chemical misacylation with an unnatural amino acid in a generalisable manner. Current technology relies on artificial suppressor tRNAs that have been specially engineered to prevent charging and proofreading by any of the synthetases. In our pure system, our only concern was the possible effects of an expected lack of tRNA base-modifying activities because such modifications can be important for function (Bjork et al. (1999) FEBS Lett. 452, 47–51), and crude translation systems can modify synthetic tRNAs (Claesson et al. (1990) FEBS Lett. 273, 173–6). As new test prototypes, we chose *E. coli* $tRNA^{Asn}$ (FIG. 14; Ohashi et al. (1976) *Nucleic Acids Res.* 3, 3369–3376) and $tRNA^{Ala}$ (discussed below; Picking et al. (1991) *Nucleic Acids Res.* 19, 5749–5754). The 5' terminal sequence of $tRNA^{Asn}$ (SEQ ID NO: 23) was mutated for optimal transcription by T7 RNA polymerase, although alternative strategies to mutagenesis exist, such as the use of M1 RNA or RNase P to process synthetic unmodified tRNA precursors (Forster and Altman (1990) *Science* 249, 783–786). The anticodons of both tRNAs were also mutated to create several variants with altered codon recognition properties (three of our $tRNA^{Asn}$ mutants are shown in FIG. 15, with the amino acid codons recognised by the tRNAs indicated in brackets). An unnatural amino acid, allylglycine (aG, sometimes alternatively abbreviated 2P), was amino-protected with an NVOC group and ligated onto to the $tRNA^{Asn}$(N) (FIG. 14) using T4 RNA ligase in a standard and generalizable strategy (see Materials and Methods; Thorson et al. (1988) *Methods in Molecular Biology* 77, 43–73; Steward and Chamberlin (1998) *Methods in Molecular Biology* 77, 325–354) to give a species that migrated on a gel with the expected mobility (FIG. 16, lane 6).

The amino group of the NVOCaG-$tRNA^{Asn}$(N) was deprotected by ultraviolet photolysis, and the aG-$tRNA^{Asn}$ (N) added to a pure translation reaction containing mMTNV template (SEQ ID NO: 31). aG was successfully incorporated at the N codon to allow downstream $^3$H-V incorporation, but gave a lower yield than the mMTV control translation (FIG. 17). The lower yield was found to be predominantly due to using insufficient aG-$tRNA^{Asn}$(N) to saturate the system, as doubling the aG-$tRNA^{Asn}$(N) RNA concentration to 1 $\mu$M (double the concentration of each natural aminoacyl tRNA in the translation, assuming 100% yield of aG-$tRNA^{Asn}$(N) from the transcription and ligation reactions) doubled the yield and incorporated the analog with about 65% processivity (based on incorporation of $^{14}$C-T before the analog and $^3$H-V after; result not shown). Translation of mMTNNV (SEQ ID NO: 32) demonstrated incorporation of adjacent analogs, with the % processivity for incorporation of the $2^{nd}$ analog similar to the first under these analog substrate-limited conditions. Note that the translations of mMTNV and mMTNNV with an uncharged tRNA having the same structure as the $tRNA^{Asn}$(N) of FIG. 14, except ending with the normal ubiquitous CCA 3' sequence (produced by run-off transcription of BstNI cut template) gave no incorporation, demonstrating that the purified system lacked charging activity for this mutant $tRNA^{Asn}$(N), and was specific for incorporation of exogenous substrate at the N codon. As an additional control, uncharged $tRNA^{Asn}$(N) did not inhibit translation of mMTV (FIG. 17).

Having established that sense codons could be commandeered in a generalisable manner for selective unnatural amino acid incorporation, the next step was to optomise the efficiency of incorporation of aG and also other unnatural amino acids, so the NVOC amino-protected forms of O-methylserine (mS) and alanine were prepared (see Materials and Methods). Using higher concentrations (up to 7 $\mu$M) of various $tRNA^{Asn}$'s (FIGS. 14 and 15) chemically aminoacylated with aG, mS, or Ala, incorporation efficiencies of greater than 90% of that obtained with Thr-$tRNA^{Thr}$ were obtained (not shown).

Interestingly, the unmodified aG-$tRNA^{Ala}$(N), which has a GUU substitution in its anticodon in comparison with the published synthetic $tRNA^{Ala}$ (Picking et al. (1991) *Nucleic Acids Res.* 19, 5749–5754), was totally inactive in translations. However, charging with Ala using a crude tRNA-free cell extract produced Ala-$tRNA^{Ala}$(N) that was incorporated efficiently. The gain of activity was probably not due to the difference in amino acid because aG worked well on $tRNA^{Asn}$(N), but more likely due to the base-modifying activity of the crude extract. The results are consistent with our hypothesis (above) that tRNA base modifications are crucial for translation activity of certain tRNAs and that initial selection of an appropriate prototype tRNA is a non-obvious process requiring trial and error. Another problem is that certain unmodified aminoacyl tRNAs are rendered inactive by denaturation during standard purification procedures (Harrington et al. (1993) *Biochemistry* 32, 7617–7622). Nevertheless, once a stable active unmodified tRNA is identified, such as our $tRNA^{Ala}$(N), the production of anticodon variants that recognise other codons in a predictable manner is straightforward (FIG. 15; see below).

Table 4 shows a representative incorporation of five successive unnatural amino acids (aG's) within a 7-mer peptidomimetic product in a manner completely dependent on added aG-$tRNA^{Asn}$(T). This improves upon the published record of two successive unnaturals (Hohsaka et al. (1999) *JACS* 121, 12194–12195), not only in length, but more importantly in generalizability and utility. Given enough different amino acid monomers, a library of random 7-mer peptidomimetics can encode substantial peptidomimetic diversity. Using the four different unmodified $tRNA^{Asn}$ variants shown in FIGS. 14 and 15, chemically aminoacylated with mS for the T codon and aG for the N, S, and V codons, full-length product was synthesized based on incorporation of carboxy-terminal $^3$H-E (Table 5). This provides evidence for incorporation of multiple and different unnatural amino acids in a single product. The complete dependency on added mS established that mS was indeed incorporated, and that this T codon is specific for $tRNA^{Asn}$ (T) (i.e. not misread by the closely related anticodon variants $tRNA^{Asn}$(N), $tRNA^{Asn}$(S), and $tRNA^{Asn}$(V) shown in FIGS. 14 and 15).

Our strategy of sense codon replacement with unnatural amino acids is a generalisable one and should therefore be extendable to all 61 sense codons. Given the significant redundancy in codon usage by nature (only 21 natural amino acids), it should be possible to create an aminoacyl tRNA library that can translate a single mRNA into substantially more than 21 different amino acids. The three termination codons are dispensible in our system, but potentially all could be translated with suppressors, with potential readthrough problems (Cload et al. (1996) *Chem. and Biol.* 3, 1033–1038) overcome by omission of the natural aminoacyl tRNA(s) that are responsible for readthrough. Effective replacement of the AUG initiation codon and fMet initiator amino acid is subject to maintenance of a different set of intermolecular contacts from elongation, but it is also possible based on known allowable substitutions in vivo and in vitro (Picking et al. (1991) *Nucleic Acids Res.* 19, 5749–5754; Wu and RajBhandary (1997) *J. Biol. Chem.* 272, 1891–1895).

A. In vitro Libraries

Figure 18:
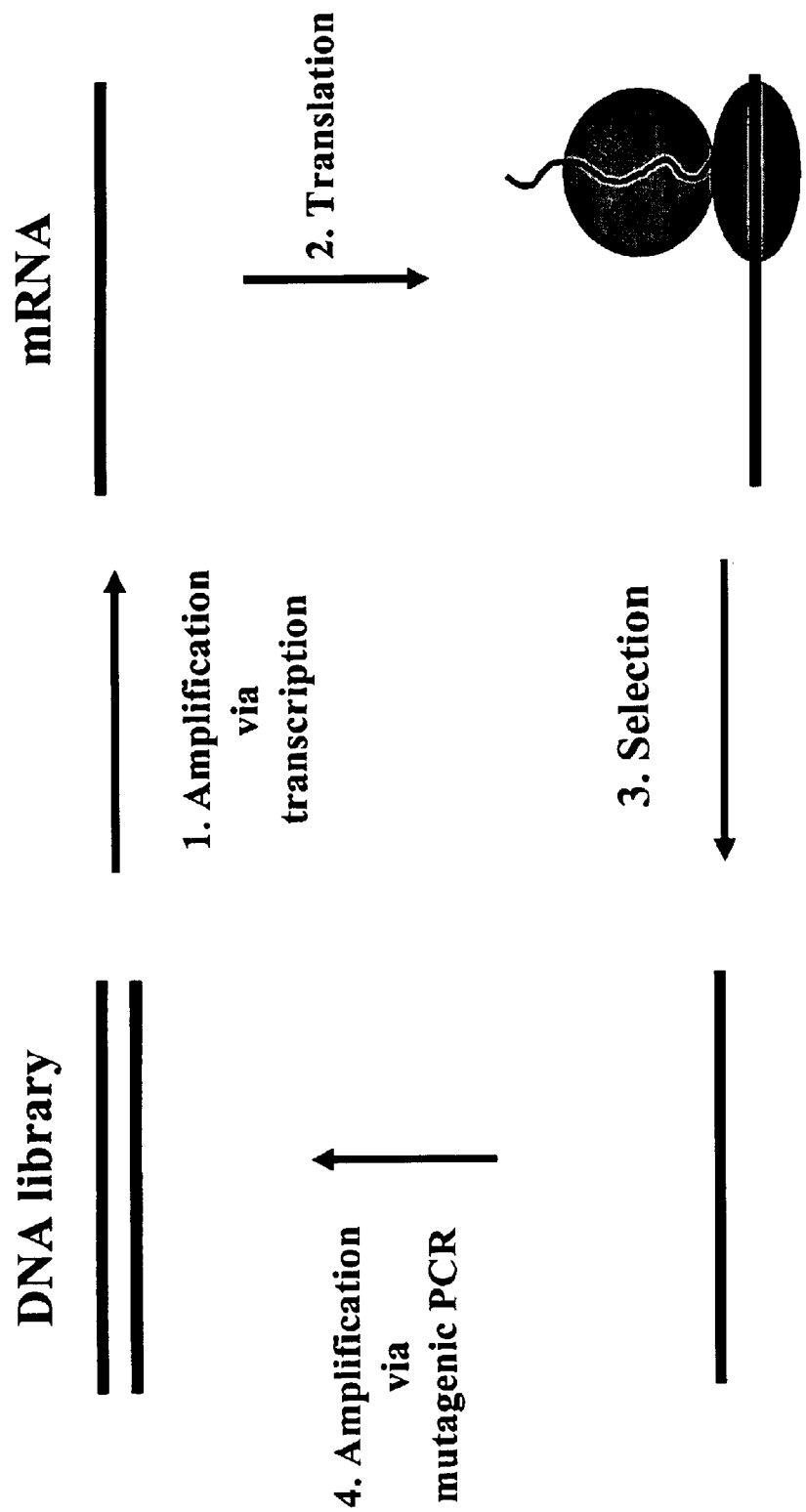
FIG. 18. Pure ribosome display. This is the pure version of the crude in vitro system (without living material) of Mattheakis et al. (supra) that can be used for the reiterative synthesis and selection (directed evolution) of peptides and peptidomimetics. The peptidomimetics need to be long enough to traverse the approximately 100-Angstrom-long ribosome tunnel that surrounds unreleased de novo-synthesized peptides in order to be selected. Dissociation of the peptide from the mRNA (and ribosome) can be prevented by omitting stop codons, release factors or certain aminoacyl-tRNAs, and by using antibiotics that stall the ribosomes.

The directed evolution in vitro of peptides or peptidomimetics from a combinatorial library of peptide analogs expressed on ribosomes is a powerful method for the rapid evolution of ligands or drug candidates that bind to any target molecule of choice. An example of our "pure ribosome display" (FIG. 18), related to ribosome display performed in crude extracts (Mattheakis and Dower (1995) PCT WO 95/11922) consists of the following steps and variants thereof:

Construction of DNA library: a synthetic oligodeoxyribonucleotide containing a randomized or partially randomized coding sequence is chemically synthesized, hybridized to an oligodeoxyribonucleotide containing an RNA polymerase promoter (e.g. a bacteriophage RNA polymerase), translation initiation sequence and start codon, extended with DNA polymerase, ligated by DNA ligase to a plasmid restriction fragment encoding an open reading frame (e.g. a repetitive spacer amino acid sequence such as our longer sequences shown in FIG. 19), purified on a gel, and quantitated.

Step 1 (FIG. 18): The synthetic DNA library is transcribed with an RNA polymerase into an mRNA library.

Step 2: The mRNA library is translated into peptide analogs with our purified ribosomes and translation factors and a reconstituted aminoacyl-tRNA pool containing a mixture of certain (but not all) wild-type aminoacyl-tRNAs and specially synthesized tRNAs charged with amino-acid analogs. Preferably, each mRNA codon is decoded by a unique charged tRNA in the pool, so the sequence of the mRNA defines a unique peptide analog sequence. For example, our spacer sequences of FIG. 19, some of which are long enough to traverse the ribosome tunnel, have been synthesized with good processivity (FIG. 20). Protein synthesis is stopped (e.g. by reaching the end of a template lacking stop codons, or by omitting release factors, or by reaching a codon for which there is no supplied aminoacyl tRNA (such as an Asn codon in the case of the longest products in FIGS. 19 and 20), or by stalling with an antibiotic.

Step 3: Ribosomes containing the random peptide analogs are isolated by centrifugation and then incubated with an immobilized target, and unbound ribosomes are washed away. Bound ribosomes are dissociated (e.g. with EDTA), and the released selected mRNA purified.

Step 4: cDNA synthesis and PCR amplification. Error-prone PCR may be used to introduce mutations.

Repetition of steps 1–4: These selection and amplification steps are repeated one or more times, as necessary (see below).

Step 5 (not shown): Amplified DNA is cloned into a plasmid for analysis by DNA sequencing to deduce the structures of selected and amplified peptidomimetics. The identification of a selected consensus sequence(s) is evidence that sufficient rounds of reiterative selection and amplification (steps 1–4) have been employed and that ligands have been identified by the experiment. Further cycles can be used to evolve ligands with higher affinities.

Modification of the method that enables a selection step in the absence of ribosomes: The DNA template is modified to encode a peptide tag that, when introduced into the peptide analog during protein synthesis, has a high affinity for mRNA or a molecule bound to the mRNA (e.g. a hybridized complementary DNA primer covalently linked to an antibody which has a high affinity for the peptide tag). The peptide-mRNA could then be separated from ribosomes before the selection step. These approaches and other possible modifications have been described (Mattheakis and Dower, supra; Doi and Yanagawa (1999) *FEBS Lett.* 457, 227–230). Alternatively, the mRNA could be 3'-end-labelled with puromycin so that it could be directly linked to the peptide for "pure mRNA display" (FIG. 21; see below).

The Szostak et al. PCT publications WO00/047775 and WO98/31700 (incorporated by reference herein) describe methods which can be readily adapted in the present invention in order to generate forms of the subject peptides and peptidomimetics which are covalently linked to the RNA molecule by which they are encoded. That is, the present invention provides a protocol that generates peptidomimetic covalently linked to the 3' end of its own mRNA, i.e., an RNA-peptidomimetic fusion.

This is accomplished by synthesis and in vitro or in situ translation of an mRNA molecule with a peptide acceptor attached to its 3' end. One preferred peptide acceptor is puromycin, a nucleoside analog that adds to the C-terminus of a growing peptide chain and terminates translation. In one preferred design, a DNA sequence is included between the end of the message and the peptide acceptor which is designed to cause the ribosome to pause at the end of the open reading frame, providing additional time for the peptide acceptor (for example, puromycin) to accept the nascent peptide chain before hydrolysis of the peptidyl-tRNA linkage (FIG. 21).

If desired, the resulting RNA-peptidomimetic fusion allows repeated rounds of selection and amplification because the coding sequence information may be recovered by reverse transcription and amplification (for example, by PCR amplification as well as any other amplification technique, including RNA-based amplification techniques such as 3SR or TSA). The amplified nucleic acid may then be transcribed, modified, and in vitro or in situ translated to generate mRNA-peptidomimetic fusions for the next round of selection. The ability to carry out multiple rounds of selection and amplification enables the enrichment and isolation of very rare molecules, e.g., one desired molecule out of a pool of $10^{15}$ members. This in turn allows the isolation of new or improved peptides and peptidomimetics which specifically recognize virtually any target or which catalyze desired chemical reactions.

Accordingly, in one aspect, the invention features a method for selection of a desired protein or peptidomimetic, involving the steps of (a) providing a population of candidate RNA molecules, each of which includes a translation initiation sequence and a start codon operably linked to a candidate protein coding sequence and each of which is operably linked to a peptide acceptor at the 3' end of the candidate protein coding sequence; (b) in vitro or in situ translating the candidate protein coding sequences in the presence of natural and/or non-naturally occurring amino acids to produce a population of candidate RNA-peptidomimetic fusions; and (c) selecting a desired RNA-peptidomimetic fusion, thereby selecting the desired peptidomimetic.

In preferred embodiments of the above methods, the population of candidate RNA molecules includes at least $10^2$, preferably, at least $10^5$, more preferably, $10^{10}$, or as many as $10^{15}$ different RNA molecules; importantly, the in vitro translation reaction is preferably carried out in a reconstituted purified mixture, not a crude translation system; the selection step involves binding of the peptidomimetic to an immobilized binding partner or assaying for a functional activity of the peptidomimetic.

In another related aspect, the invention features kits for carrying out any of the selection methods described herein.

In a final aspect, the invention features a microchip that includes an array of immobilized peptidomimetics of the present invention.

B. Target Molecules

The target molecule can be virtually any molecule for which interaction with a peptide or peptidomimetic of the present invention may be useful. In certain embodiments, the target molecule is a biopolymer, such as a nucleic acid (DNA or RNA), a protein, a lipid, a carbohydrate or the like.

In choosing a polypeptide screening target, factors which can be considered include solubility, peptide chain length, requirement of post-translational modifications, or addition of co-factors, and/or monomeric or oligomeric nature of protein(s) upon which the target is based. In general, it will be desirable that the polypeptide target be soluble, partially purified or pure, and immobilized on a solid support by methods standard in the art.

Accordingly, the present invention contemplates screening targets which correspond to (e.g. include) such domain structures as: SH2 domains; SH3 domains; ankyrin-like repeats; WD40 motifs; Kunitz-type inhibitor domains; growth factor-like domains such as EGF-like domains; Kringle domains; fibronectin finger-like domains; heparin-binding domains; death domains; TRAF domains; pleckstrin homology (PH) domains; ITAMs; catalytic domains such as kinase domains; phosphatase domains; phospholipase domains; guanine nucleotide exchange factor (GEF) domains; and hydrolase domains (such as protease domains); or DNA binding domains such as leucine zippers, zinc fingers and helix-loop-helix motifs.

Where the protein of interest is a transmembrane protein, the screening target can be derived from a soluble extracellular or cytoplasmic domain. To illustrate, the screening target can correspond to the extracellular domain of a guanylyl cyclase, a cytokine receptor, a tyrosine kinase receptor, or a serine/threonine kinase receptor. In other embodiments, the screening target can correspond to a soluble portion of a G-protein coupled receptor (GCR) which retains ligand binding activity. For example, as described above, certain of the extracellular loops between the transmembrane portions of the GCRs have been shown to retain ligand binding activity even when provided free in solution. In still other embodiments, the screening target can be reconstituted in a lipid bilayer, such as a liposome or other vesicle (see, for example, Kalva Kolanu et al. (1990) *Biotechniques* 11:248; and The Huang U.S. Pat. Nos. 4,957,735 and 4,708,933) and the lipid/protein combination used as the screening target.

Merely for purposes of illustration, the following protein targets are described for use in the subject method.

In one embodiment, potential therapeutic targets are receptors from the neu receptor family. In women in the U.S.A., breast cancer is the most common cancer and is only second to lung cancer in the number of cancer deaths. A prime breast cancer target is neu/erbB-2/HER-2, a 185 kD trans-membrane phosphoglycoprotein tyrosine kinase (Shih et al. (1981) *Nature* 290:261). Amplification or over expression of the neu oncogene occurs in about 30% of breast and ovarian adenocarcinomas, a finding that correlates with a poor response to primary therapy (Slamon et al. (1987) *Science* 235:177; and Hayes et al. (1993) *Annals of Oncology* 4:807). Transfection of NIH 3T3 cells with the neu oncogene results in transformation (Shih et al., supra), and introduction of an activated neu oncogene into mice results in the transformation of the entire mammary epithelium (Muller et al. (1988) *Cell* 54:105) or the stochastic appearance of mammary tumors (Bouchard et al. (1989) *Cell* 57:931).

Evidence is accumulating that breast cancer may be inhibited by molecules that bind to neu or a ligand of neu, such as members of the heregulin family (Holmes et al. 1992 *Nature* 256:1205). MAbs and their radiolabelled conjugates that bind to the extracellular domain of neu retard the growth of breast cancer cells in culture and in nude mice without the selection of neu-negative cell clones (DeSantes et al. (1992) *Cancer Res.* 52:1916; and Drebin et al. (1986) *PNAS* 83:9129). Such MAbs and their derivatives, such as the recombinant humanised MAb, Herceptin, that is used in the clinic for advanced breast cancer treatment (Colomer et al. (2001) *Cancer Investigation* 19, 49–56), may alter the neu signal transduction pathway and affect tumor growth in several different ways. They may (i) over stimulate neu, thereby causing differentiation (Bacus et al. (1992) *Cancer Res.* 52:2580), (ii) prevent homo- or hetero-dimerization of neu, thereby inactivating neu (Caraway et al. (1994) *Cell* 78:5), (iii) cause cellular internalization and down regulation of neu (Tagliabue et al. (1991) *Int. J. Cancer* 47:93), (iv) deliver conjugated cytotoxic radionuclides or toxins to the cell surface or cytoplasm, or (v) prevent binding of a ligand to neu.

The peptidomimetics which can be derived by the present invention can be useful for inhibiting the biological function of neu by, for example, competitively disrupting the binding of neu with its ligand or other protein, or preventing allosteric activation of an enzymatic activity associated with neu. Alternatively, they may be useful as agonists causing over stimulation or down-regulation of neu.

Yet another potential target is Interleukin-8 (IL-8). IL-8 is a chemoattractant and activator of neutrophils, and has been implicated in a wide range of acute and chronic inflammatory diseases (Murphy (1994) *Annu. Rev. Immunol.* 12:593–633). Human IL-8 is a 72-amino-acid-long polypeptide produced by monocytes, fibroblasts, keratinocytes and endothelial cells upon induction by factors such as tumor necrosis factor, interleukin-1, and lipopolysaccharides (Murphy, supra). Certain analogs of IL-8 act as IL-8 antagonists in vitro by inhibiting neutrophil activation (chemotaxis, exocytosis and respiratory burst), suggesting that anti-IL-8 agents may have therapeutic potential for inflammatory diseases (Moser et al. (1993) *J. Biol. Chem.* 268:7125–7128).

The monomeric IL-8 peptide forms dimers in vitro with a $K_d$ of 20 $\mu$M (Paolini et al. (1994) *J Immunology* 153: 2704; and Burrows et al. (1994) *Biochemistry* 33:12741–12745), so it is possible that the monomer and/or the dimer are active in vivo. Mutants that cannot dimerize are active in functional assays in vitro (Rajarathnam et al. (1994) *Science* 264:90). Interestingly, NMR and X-ray determination of the three-dimensional structure of the IL-8 dimer (Clore et al. (1990) *Biochemistry* 29:1689–1696; and Baldwin et al. (1991) *PNAS* 88:502) revealed that it resembled the peptide-binding groove of MHC class I and II proteins (Bjorkman et al. (1987) *Nature* 329:506), so it is conceivable that IL-8 dimers may be able to bind to in vitro-selected peptide or peptidomimetic sequences in a manner similar to the MHC molecules. Therefore, the IL-8 dimer, in addition to the monomer, is an attractive target.

In the case of the IL-8 pathway, an alternative target from IL-8 is a functional fragment of the IL-8 receptor. Even small fragments of the human and rabbit IL-8 Type 1 receptor of 39 and 44 amino acids, respectively, are functional in IL-8 binding assays (Gayle et al. (1993) *J Biol Chem* 268:7283–7289). Thus, members of the largest receptor family, the seven transmembrane receptors, are potential targets.

The cellular proto-oncogene c-myc is involved in cell proliferation and transformation but is also implicated in the induction of programmed cell death (apoptosis). The c-Myc protein is a transcriptional activator with a carboxyl-terminal basic region/helix-loop-helix (HLH)/leucine zipper (LZ) domain. It forms heterodimers with the HLH/LZ protein Max and transactivates gene expression after binding DNA E-box elements. The protein Max is the obligatory partner of c-Myc for many its biological functions analyzed to date. For instance, Myc must heterodimerize with Max to bind DNA and perform its oncogenic activity.

According to the present invention, the subject method can be used to derive peptides and peptidomimetics which can inhibit formation of complexes between Myc and other proteins such as Max, and/or which can inhibit the binding of a Myc complex to a myc-responsive element in a gene. The total synthesis of Myc-Max and Max-Max dimers are described by Canne et al. (1995) *J Am Chem Soc* 117:2998–3007.

The total synthesis of TGF☐ has been described by Woo et al. (1989) *Protein Eng* 3:29–37, and provides another possible target molecule.

Yet another target which can derived for use in the subject method is fibronectin, a glycoprotein involved in cell adhesion, tissue organization and wound healing. The total synthesis of fibronectin modules is described by, for example, Williams et al. (1994) *J Am Chem Soc* 116:10797–10798.

It has been previously shown that the expression of human immunodeficiency virus type 1 (HIV-1) major gag protein, p24, is persistent on the surface of HIV-1-infected cells (Nishino et al. (1992) *Vaccine* 10:677–683). The total synthesis of a C-terminal 100 amino acid fragment of p24 is described by Mascagni et al. (1990) *Tetrahedron Lett* 31:4637–4640, and that portion of the p24 protein can be used to generate a screening target.

Likewise, the HIV protease has been synthesized by total chemical synthetic means (Kent et al. PCT Publication WO93/20098) and provides a unique target for developing inhibitors of the catalytic activity as well as inhibitors of protein-protein interactions involving the protease.

While many, of the targets illustrated above may be prepared by chemical synthesis, this is by no means a requirement or even a preference. An advantage of our invention is that any other method may be used to prepare a partially purified or pure target, such as purification from its biological source, biosynthesis, or recombinant DNA-based expression.

Materials and Methods

Construction of plasmids for the over-expression of his-tagged and untagged *E. coli* IF1, IF2 and IF3 proteins. *E. coli* initiation factor coding sequences, each containing an insertion of six histidines immediately after the N-terminal methionine, were synthesized by PCR from published plasmids and sub-cloned into a vector derived from pET24a (Novagen). Plasmid pXR201 containing the native IF1 sequence encoded by an artificial sequence of *E. coli*-preferred codons (instead of infA codons) was kindly supplied by R. Spurio and C. Gualerzi (Calogero et al. (1987) *Mol Gen Genet* 208, 63–9) and sub-cloned to give pAF1H. Plasmid pSL4 containing the native IF2 sequence encoded by infB was kindly supplied by S. Laalami and M. Grunberg-Manago (Laalami et al. (1991) *J Mol Biol* 220, 335–49) and sub-cloned to give pAF2H. Plasmid pDD1 containing the native IF3 sequence encoded by infC was kindly supplied by N. Brot and I. Schwartz (De Bellis and Schwartz (1990) *Nucleic Acids Res* 18, 1311) and sub-cloned to give pAF3H. The sequences of the three subclones, characterized by a combination of restriction digests and sequence analyses, begin (ligation sites underlined) with TATACA/TATG(CAC)$_6$ (SEQ ID NO: 47) before the second amino acid; the final amino acid is followed by the sequence TAAG/AATTCGAGCTCCGTCGA/42 bp deletion/AGATCC (SEQ ID NO: 48), and the remainder of the sequence is from pET24a. Analogous methods were also used to clone and over-express untagged versions of IF1, IF2 and IF3.

Over-expression and purification of *E. coli* translation factor proteins. Plasmid pHTA7 (in *E. coli* BL21(DE3)) encoding his-tagged *E. coli* EF-Tu, containing a his$_6$ sequence inserted between the first two codons of TufA, and plasmid pHTS, containing a his$_6$ sequence inserted between the first two codons of Tsf was kindly supplied by Y.-W. Hwang and D. Miller (see Hwang et al. (1997) *Arch Biochem Biophys* 348, 157–62). Plasmid pRSET/EF-G(His) (in *E. coli* BL21(DE3) cells together with the pLysS plasmid) encoding his-tagged *E. coli* EF-G (EF-GH), containing an N-terminal extension of about 30 amino acids including his$_6$, was kindly supplied by A. Savelsbergh and W. Wintermeyer (Semenkov et al. (1996) *Proc Natl Acad Sci USA* 93, 12183–8). Expression of our three his-tagged initiation factor subclones (in *E. coli* BL21(DE3)pLysS; Novagen) and the three supplied clones was induced with IPTG. All the factors were expressed predominantly in the soluble cellular fractions and purified by step elution from Ni—NTA agarose columns using standard protocols (Qiagen), except that 10 $\mu$M GDP was included up to the last dialysis step for EF-TuH. All factors were dialysed against buffer A (10 mM Tris-HCl pH 7.4, 1 mM MgCl$_2$, 1 mM DTT). Precipitated IF3H was recovered by redissolving in 5M urea (Hershey et al. (1977) *Arch Biochem Biophys* 182, 626–38), diluted and then dialysed against buffer A containing 100 mM NH$_4$Cl. In contrast to the extensive proteolytic degradation observed by others during the over-expression and purification of native IF2 (Mortensen et al. (1991) *Biochimie* 73, 983–9), recombinant IF2H was not proteolytically labile. Pure *E. coli* release factors (RFs) RF1, RF2, RF3, and RRF, were prepared as described (Yu et al. (1998) *J. Mol. Biol.* 284, 579–590). All factors were stored at −80° C. They were thawed many times without loss of activity, except for EF-TuH, which was stored at 4° C. after thawing and used within a few weeks.

Purification of *E. coli* ribosomes (Kung et al. (1974) *Arch Biochem Biophys* 162, 578–84). SOLR™ cells (Stratagene) grown to mid-log phase were resuspended in buffer B (60 mM KOAc, 14 mM Mg(OAc)$_2$, 10 mM Tris-HOAc, 1 mM DTT, pH 7.9), sonicated, and centrifuged at 10 000 g. The supernatant was centrifuged at 30 000 g, and the resulting supernatant was then centrifuged at 150 000 g. The ribosome pellet was washed by stirring in buffer B containing 1M NH$_4$Cl at 4° C. overnight and then repelleting at 150 000 g. The washing was repeated twice more to give 3× washed ribosomes which were resuspended in buffer C (10 mM Mg(OAc)$_2$, 1 mM Tris-HCl pH 7.4, 1 mM DTT) and stored at −80° C.

Synthesis of mRNAs. mRNAs were transcribed (Milligan and Uhlenbeck (1989) *Methods in Enzymology* 180, 51–62) from synthetic oligodeoxyribonucleotides (Research Genetics) and purified by gel electrophoresis (Forster and Symons (1987) *Cell* 49, 211–20). Because the templates are relatively long, extended deprotection times were necessary (12 h) following the synthesis of the blocked oligonucleotides to enable optimal transcription.

Preparation of aminoacyl tRNAs. Pure *E. coli* tRNA isoacceptors were from Subriden RNA. Each isoacceptor was prepared by the manufacturer from *E. coli* total tRNA (Plenum) using three column chromatography steps. The first fractionation used BD cellulose, the second, DEAE Sephadex at pH 7, and the third, DEAE Sephadex at pH 5 or Sepharose. Natural aminoacyl tRNAs were prepared from these isoacceptors as follows. High specific activity $^3$H-fmet-tRNA$_i^{fmet}$ (24 000 d.p.m./pmol in Table 1) and low specific activity $^3$H- or $^{35}$S-fmet-tRNA$_i^{fmet}$ (a few hundred d.p.m./pmol; used for all other studies) were prepared as described (Robakis et al. (1981) *Proc Natl Acad Sci USA* 78, 4261–4) using MetRS, met-tRNA$_i^{fmet}$ formyltransferase and $N^{5,10}$-methenyl THF (synthesized using $N^{10}$-formyl THF synthetase. $^{14}$C-thr-tRNA$_3^{thr}$ (510 d.p.m./pmol) and $^3$H-val-tRNA$_1^{val}$ (21 000 d.p.m./pmol in FIGS. 5–7; 28 000 d.p.m./pmol in FIGS. 4 and 8) were aminoacylated as described (Robakis et al. (1981) *Proc Natl Acad Sci USA* 78, 4261–4) with ThrRS, ValRS or, for the lower specific activity val-tRNA, a tRNA-free preparation of total *E. coli* synthetases partially purified from an 150 000 g supernatant by step elution with 0.3M KCl from DEAE Sepharose (see Kung et al. (1975) *J Biol Chem* 250, 1556–62).

Figure 22:
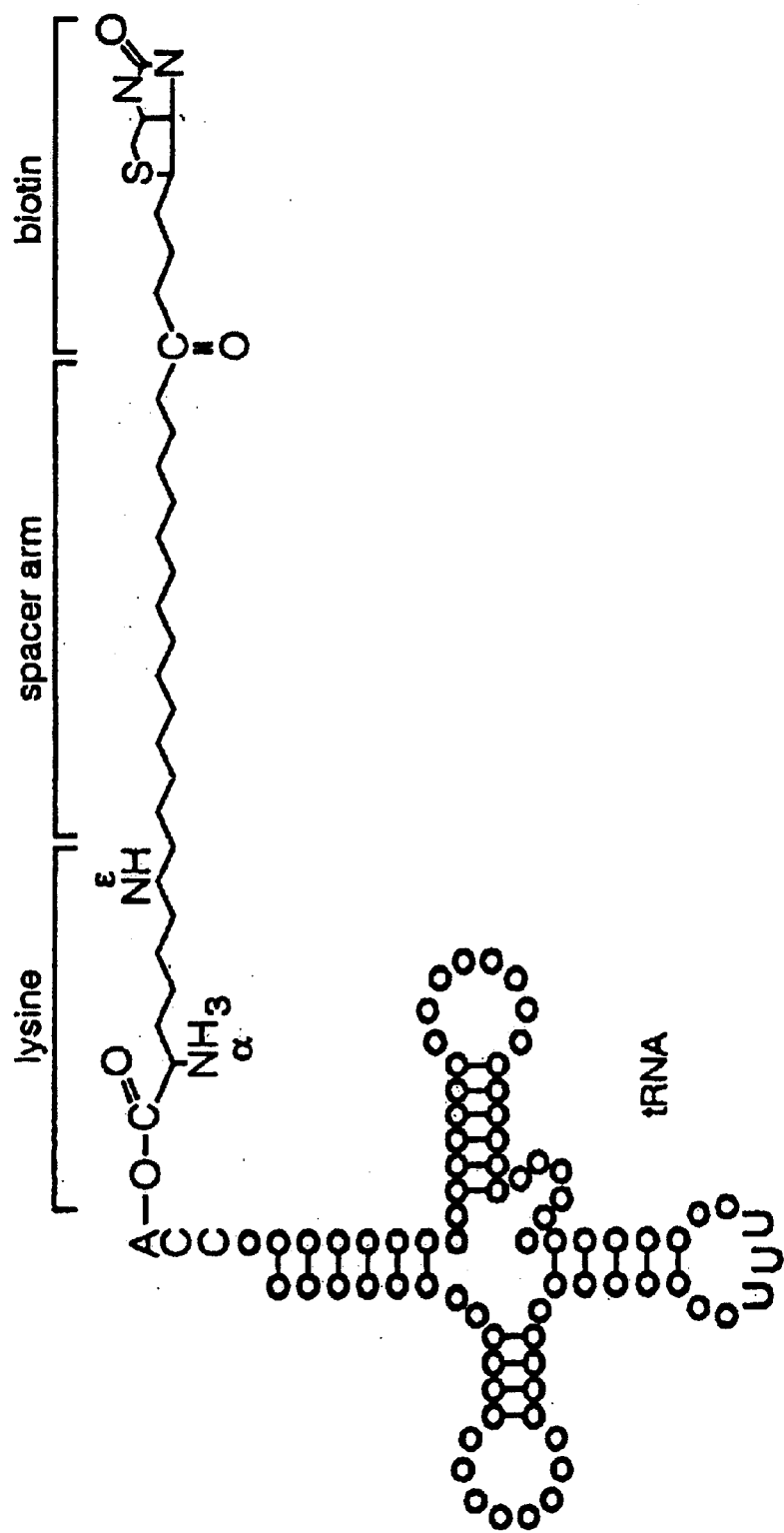
FIG. 22. Promega's Transcend biotinyl-lysine tRNA$^{Lys}$ (*E. coli*; see Materials and Methods).

Biotin-labeled-lys-tRNA$^{lys}$ (Transcend™ tRNA; FIG. 22) was purchased from Promega. This material was prepared by the manufacturer from *E. coli* total tRNA by charging with lysine using a crude preparation of total synthetases, enriching for lys-tRNA$^{lys}$ by ion exchange chromatography, and chemical coupling to biotin via an uncharged, 13-carbon-long spacer.

NVOC-amino protected aminoacyl tRNAs were prepared, stored and used by methods standard in the art (detailed in Thorson et al. (1988) *Methods in Molecular Biology* 77, 43–73; Steward and Chamberlin (1998) *Methods in Molecular Biology* 77, 325–354). Briefly, pdCpA was chemically synthesised from adenosine and a deoxycytidine derivative. The various unnatural amino acids were purchased in unprotected form from standard suppliers (e.g. Sigma, Aldrich, Fluka, Bachem and Novabiochem). Our most commonly used NVOC-amino acids, such as aG, mS and Ala, lacked reactive amino acid side chains requiring chemical protection, so they were synthesized directly from the unprotected amino acids by amino protection with NVOC-Cl. All suitably protected amino acids, including those with additional side-chain protections synthesized by the standard methods, were activated by cyanomethyl ester synthesis and then coupled to pdCpA. The resulting NVOC-protected aminoacylated pdCpA compounds (and also their conjugates with RNAs) were stable when stored in an aqueous solution with a pH of approximately 5 in the dark at −80° C. NVOC-protected aminoacylated pdCpA compounds were ligated by T4 RNA ligase to various tRNA derivatives lacking the terminal CA dinucleotide, and conjugates were purified and stored (see above). The resulting NVOC-protected aminoacyl tRNAs were deprotected by UV-irradiation immediately prior to use in translations.

Assay of his-tagged *E. coli* translation factor proteins. Initiation factor assays (Kung et al. (1974) *Arch Biochem Biophys* 162, 578–84) used custom-synthesized ApUpG RNA template (TriLink Biotechnologies). A mixture containing 0.95 μM 1F1H, 0.15 μM IF2H, 0.78 μM IF3H, 3× washed ribosomes at 0.029 A$_{260}$/μl (33 nM estimated to be active in translation; see below), 0.29 μM $^3$H-fmet-tRNA$_i^{fmet}$, 150 μM AUG and 0.4 mM GTP in 50 mM Tris-HCl pH 7.4, 100 mM NH$_4$Cl, 5 mM Mg(OAc)$_2$ and 2 mM DTT was incubated at 37° C. for 10 min. After dilution, the mixture was rapidly filtered through nitrocellulose to separate initiation complex-bound fmet-tRNA$_i^{fmet}$ from unbound species. Reactions that lacked template were used as controls for non-specific binding (29% of maximal d.p.m. for Table 1; 9% of maximal d.p.m. using higher (saturating) concentrations of ribosomes that bound 70% of $^3$H-fmet-tRNA$_i^{fmet}$). Because of the high affinity of EF-Tu for EF-Ts, EF-Ts activity assays were performed (Weissbach and Pestka (1977) *Molecular Mechanisms of Protein Biosynthesis, Academic Press, New York, N.Y.*) with EF-TuH, indicating a copurification level of about 2%. EF-TuH activity was measured by GDP binding (Weissbach and Pestka (1977) *Molecular Mechanisms of Protein Biosynthesis, Academic Press, New York, N.Y.*), and EF-GH activity was measured by a ribosome-dependent GTPase assay (Weissbach and Pestka (1977) *Molecular Mechanisms of Protein Biosynthesis, Academic Press, New York, N.Y.*).

Translations. The components of translation mixes were adapted from published work (Robakis et al. (1981) *Proc Natl Acad Sci USA* 78, 4261–4; Cenatiempo et al. (1982) *Arch Biochem Biophys* 218, 572–8). 5× Premix buffer was prepared from a solution containing 180 mM Tris-HOAc (pH 7.5), 50 mM sodium 3,3-dimethyl-glutarate (pH 6.0), 180 mM NH$_4$OAc, 10 mM DTT, 140 mM potassium phosphoenolpyruvate (pH 6.6), 195 mM KOAc and 4 mM spermidine.3HCl by adjusting it to pH 6.8 with NaOH. As a representative example, the mixture in the translation of the MTTV mRNA template (FIG. 6; 30 μl total volume) included 1× premix buffer, 9.5 mM Mg(OAc)$_2$, 1 mM GTP, 14 ng/μl pyruvate kinase, 4.3% PEG 8000, 0.95 μM 1F1H, 0.15 μM IF2H, 0.78 μM IF3H, 3.1 μM EF-TuH, 0.88 μM EF-GH, 3× washed ribosomes at 0.029 A$_{260}$/μl (33 nM estimated to be active in translation; see FIG. 4), 0.29 μM $^3$H-fmet-tRNA$_i^{fmet}$, 0.58 μM $^{14}$C-thr-tRNA$_3^{thr}$, 0.29 μM $^3$H-val-tRNA$_1^{val}$, and 1 μM mRNA. This mixture was incubated at 37° C. for 50 min., although some translations were as short as 1 min. (FIG. 4). The set up for some translations also included preincubations at 37° C. for 10 min. of an initiation mix (GTP, 1F1H, IF2H, IF3H, ribosomes, $^3$H-fmet-tRNA$_i^{fmet}$ and mRNA) and an elongation factor mix (GTP, EF-TuH, EF-GH, $^{14}$C-thr-tRNA$_3^{thr}$ and $^3$H-val-tRNA$_1^{val}$ (FIG. 4)).

For HPLC analysis (FIG. 6), peptides and amino acids were released from tRNAs by addition of 1M NaOH (6 μl) and incubation at 37° C. for 20 min. Unlabeled marker peptides (Research Genetics) were then added (18 μl with a combined peptide concentration of 10 μg/μl in H$_2$O), the solution was acidified with glacial acetic acid (5 μl), microcentrifuged, and the supernatant was then microcentrifuged through a Microcon 10 ultrafiltration device (10 kD cut-off, Amicon). A portion of the filtrate (20 μl) was loaded onto a C18 reversed phase column (Vydac) and eluted with a 0 to 31.5% H$_2$O/MeCN gradient containing 0.1% TFA at 1 ml/min. with detection by absorbance at 229 nM and scintillation counting of 42-drop fractions using a dual-labeled d.p.m. program (Packard).

For analysis of the fMTV and fMVT syntheses, formylated peptides and formyl methionine were separated from unformylated amino acids by base hydrolysis, acidification, and cation-exchange chromatography on mini-columns (Peacock et al. (1984) *Proc Natl Acad Sci USA* 81, 6009–13).

Control translations. Additional translations were performed to assess the dependence on components other than the translation factors. Omission of $^3$H-fmet-tRNA$_i^{fmet}$ or $^{14}$C-thr-tRNA$_3^{thr}$ abolishes fMTV synthesis from mRNA MTV, based on incorporation of $^3$H-val into product. In the experiment omitting $^{14}$C-thr-tRNA$_3^{thr}$, addition of uncharged tRNA$_3^{thr}$ does not reconstitute measurable fMTV synthesis, demonstrating a lack of ThrRS activity under translation conditions, as expected for a purified system (as a further control, addition of uncharged thr-tRNA$_3^{thr}$ was not inhibitory to fMTV synthesis). Omission of $^3$H-val-tRNA$_1^{val}$ abolishes fMVT synthesis from mRNA MVT (FIG. 4), based on incorporation of $^{14}$C-thr-tRNA$_3^{thr}$ into product. The T/V ratios in the mRNA MVT and mRNA mMV (FIG. 3) products are about 1.0 and 0, respectively, as expected. Omitting ribosomes gives the lowest background radioactivity measurements, and translations lacking mRNA do not accumulate formylated peptide products with time. Omitting rabbit muscle pyruvate kinase (the protein (Jelenc and Kurland (1979) *Proc Natl Acad Sci USA* 76, 3174–8) from Sigma migrates as a single major band on SDS-PAGE) decreases the yield of product by 50%. The standard concentration of Mg$^{2+}$ (9.5 mM) is optimal, but translation can occur efficiently at higher and lower concentrations.

TABLE 1

Factor dependencies for initiation complex formation.

| Initiation factor omitted | Initiation complex[a] | | |
|---|---|---|---|
| | His-tagged[b] | Native (Kung et al.)[c] | Native (Dubnoff and Maitra)[d] |
| None | 100 | 100 | 100 |
| IF1 | 48 | 61 | 36 |
| IF2 | 0 | 4 | 7 |
| IF3 | 7 | 17 | 48 |

[a] % Maximal binding of $^3$H-labeled fmet-tRNA$_i^{fmet}$ to ribosomes in the presence of GTP.
[b] Performed with purified his-tagged initiation factors, ApUpG template and 5 mM Mg$^{2+}$ (see Materials and Methods). The maximum concentration of fmet-tRNA$_i^{fmet}$ specifically bound into initiation complexes was 19 nM.
[c] Performed with purified native initiation factors, poly(U:G) (3:1) template and 10 mM Mg$^{2+}$.
[d] Performed with purified native initiation factors, ApUpG template and 5 mM Mg$^{2+}$.

TABLE 2

Measurement of processivity of synthesis of a 7-mer peptide (SEQ ID NO: 44). Peptide product d.p.m. from 5.1 μl coupled transcription/translations containing translation factors IF2, IF3, EF-Tu and EF-G are converted to pmoles.

| Peptide encoded by mRNA template | $^{14}$C-Thr (pmol) | $^3$H-Val (pmol) | $^{14}$C-Thr/ $^3$H-Val measured | Thr/Val expected |
|---|---|---|---|---|
| fMetThrThrThrThrThrVal | 0.45 | 0.07 | 6.4 | 5 |
| fMetThrVal | 0.06 | 0.06 | 1.0 | 1 |
| fMetVal | 0.008 | 0.07 | 0.11 | 0 |

TABLE 3

Stimulation of pure translation system by pure *E. coli* release factors (RFs) RF1, RF2, RF3, and RRF (Yu et al. (1998) J. Mol. Biol. 284, 579–590; see Materials and Methods). mRNAs either lacked a stop codon (mMTTV) or encoded a stop codon (mMTCV$_{UAG}$) directly following the fourth amino acid codon. Product dpm: radioactive disintergrations per minute of tritiated valine incorporated into peptide products. All translations contained translation factors IF1, IF2, IF3, EF-Tu, EF-G and EF-Ts.

| mRNA | Supplied aminoacyl-tRNAs | RFs | Product dpm | Peptide product |
|---|---|---|---|---|
| mMTTV | fM, T, V | − | 4597 | fMTTV |
| mMTTV | fM, T, V | + | 7187 | fMTTV |
| mMTCV$_{UAG}$ | fM, T, C, V | − | 2676 | fMTCV |
| mMTCV$_{UAG}$ | fM, T, C, V | + | 3866 | fMTCV |

TABLE 4

Figure 14:
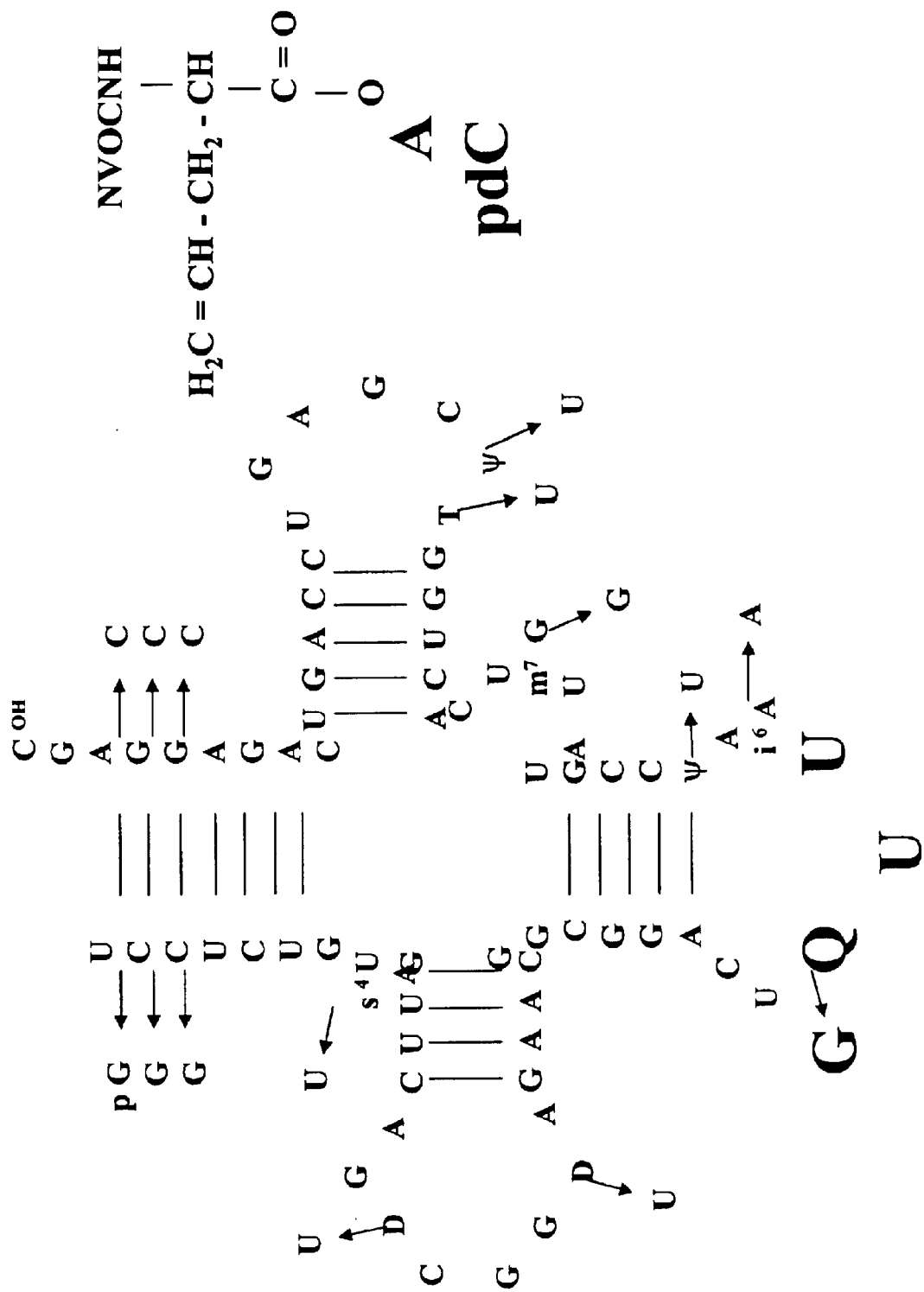
FIG. 14. A generalizable approach for the synthesis of aminoacyl-tRNAs charged with unnatural amino acids specific for the codon(s) of choice. The elongator tRNA$^{Asn-CA}$, (SEQ ID NO: 24) synthesized in vitro (FIG. 16, lane 5) from our recombinant DNA clone prepared from synthetic oligodeoxyribonucleotides, contains substantial base alterations from the natural tRNA$^{Asn}$ sequence (SEQ ID NO: 22) that are indicated by arrows. The anticodon of the tRNA is indicated with large letters. An amino NVOC-protected unnatural amino acid was chemically aminoacylated on pdCA (SEQ ID NO: 33) (see upper right) and then ligated to the tRNA$^{Asn-CA}$ (produced by run-off transcription of Fok I cut template) with T4 RNA ligase (FIG. 16, lane 6). The approach is generalizable because no aminoacyl-tRNA-synthetase or natural tRNA was required.

Incorporation of five successive unnatural amino acids into a peptidomimetic product. Allylglycine is abbreviated as aG; its structure is shown in FIG. 14. The artificial tRNA$^{Asn}$ charged with aG is termed aG-tRNA(T) because it recognises a T codon (FIG. 15). Total d.p.m.: total $^3$H d.p.m. eluted from mini-column (see Materials and Methods). All translations contained translation factors IF1, IF2, IF3, EF-Tu, EF-G and EF-Ts.

| mRNA | Supplied aminoacyl-tRNAs | Total dpm | Peptidomimetic product |
|---|---|---|---|
| mMTTTTTV | fM, aG-tRNA(T), V | 2721 | fM-aG-aG-aG-aG-aG-V |
| mMTTTTTV | fM, T, V | 7685 | fMTTTTTV |
| mMTTTTTV | fM, V | 1116 | none (background dpm) |
| — | fM, V | 1113 | none (background dpm) |

TABLE 5

Incorporation of two different types of unnatural amino acids into a peptidomimetic product. O-methyl serine is abbreviated as mS. Four artificial aminoacyl tRNAs were used: mS-tRNA(T), aG-tRNA(N), aG-tRNA(S), and aG-tRNA(V), with the respective mRNA codons recognised by each artificial tRNA given in parentheses. The highly labelled $^3$H-amino acid was E. Total d.p.m.: total $^3$H d.p.m. eluted from mini-column. All translations contained translation factors IF1, IF2, IF3, EF-Tu, and EF-G. The sequence of mRNA mMTNSVE is provided as SEQ ID NO: 45.

| mRNA | Supplied aminoacyl-tRNAs | Total dpm | Peptidomimetic product |
|---|---|---|---|
| mMTNSVE | fM, mS-tRNA(T), aG-tRNA(N), aG-tRNA(S), aG-tRNA(V), E | 2353 | fM-mS-aG-aG-aG-E |
| mMTNSVE | fM, aG-tRNA(N), aG-tRNA(S), aG-tRNA(V), E | 899 | none (background) |
| — | fM, mS-tRNA(T), aG-tRNA(N), aG-tRNA(S), aG-tRNA(V), E | 1033 | none (background) |
| mMTTV | fM, T, V | 7100 | fMTTV |

SEQUENCE LISTING

<160> NUMBER OF SEQ ID NOS: 48

<210> SEQ ID NO 1
<211> LENGTH: 18
<212> TYPE: DNA
<213> ORGANISM: Bacteriophage T7

<400> SEQUENCE: 1
taatacgact cactatag                                                    18

<210> SEQ ID NO 2
<211> LENGTH: 65
<212> TYPE: DNA
<213> ORGANISM: Artificial Sequence
<220> FEATURE:
<223> OTHER INFORMATION: Description of Artificial Sequence:FROM
      SYNTHETIC DNA

<400> SEQUENCE: 2
ggaattcaac ggtggtcatt tttttttacct ccttactaaa gttaaccta tagtgagtcg     60 tatta                                                                  65

<210> SEQ ID NO 3
<211> LENGTH: 48
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 3
ggguuaacuu uaguaaggag guaaaaaaaa ugaccaccgu ugaauucc                  48

<210> SEQ ID NO 4
<211> LENGTH: 45
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 4
ggguuaacuu uaguaaggag guaaaaaaaa ugaccguuga auucc                     45

<210> SEQ ID NO 5
<211> LENGTH: 42
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 5
ggguuaacuu uaguaaggag guaaaaaaaa ugguugaauu cc                        42

<210> SEQ ID NO 6
<211> LENGTH: 45
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 6

-continued ggguuaacuu aaguaaggag guaaaacaca ugguuaccga auucc                45

<210> SEQ ID NO 7
<211> LENGTH: 45
<212> TYPE: RNA
<213> ORGANISM: Artificial Sequence
<220> FEATURE:
<223> OTHER INFORMATION: Description of Artificial Sequence:FROM
    SYNTHETIC RNA

<400> SEQUENCE: 7
ggguauuaua cuguaaggag guaaaacaca ugguuaccga auucc                45

<210> SEQ ID NO 8
<211> LENGTH: 35
<212> TYPE: RNA
<213> ORGANISM: Artificial Sequence
<220> FEATURE:
<223> OTHER INFORMATION: Description of Artificial Sequence:FROM
    SYNTHETIC RNA

<400> SEQUENCE: 8
ggguaaggag guaaaacaca ugguuaccga auucc                           35

<210> SEQ ID NO 9
<211> LENGTH: 46
<212> TYPE: RNA
<213> ORGANISM: Artificial Sequence
<220> FEATURE:
<223> OTHER INFORMATION: Description of Artificial Sequence:FROM
    SYNTHETIC RNA

<400> SEQUENCE: 9
ggguuaacuu aaguaaggag guaaaacaca ugaccaaagu ugaauu               46

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence:FROM
    SYNTHETIC DNA

<400> SEQUENCE: 10

Met Thr Thr Val
 1

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence:FROM
    SYNTHETIC DNA

<400> SEQUENCE: 11

Met Thr Val
 1

<210> SEQ ID NO 12
<211> LENGTH: 2
<212> TYPE: PRT
<213> ORGANISM: Artificial Sequence
<220> FEATURE:
<223> OTHER INFORMATION: Description of Artificial Sequence:FROM
    SYNTHETIC DNA

<400> SEQUENCE: 12

Met Val
1

<210> SEQ ID NO 13
<211> LENGTH: 3
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 13

Met Val Thr
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 14

Met Thr Lys Val
1

<210> SEQ ID NO 15
<211> LENGTH: 2
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 15

Met Thr
1

<210> SEQ ID NO 16
<211> LENGTH: 3
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 16

Met Thr Thr
1

<210> SEQ ID NO 17
<211> LENGTH: 74
<212> TYPE: RNA
<213> ORGANISM: Escherichia coli

<400> SEQUENCE: 17
ggcgcguuaa caaagcgguu auguagcgga uugcaaaucc gucuaguccg guucgacucc      60
ggaacgcgcc ucca                                                       74

<210> SEQ ID NO 18
<211> LENGTH: 52
<212> TYPE: RNA
<213> ORGANISM: Artificial Sequence
<220> FEATURE:
<223> OTHER INFORMATION: Description of Artificial Sequence:FROM

SYNTHETIC RNA

<400> SEQUENCE: 18
ggguuaacuu aguaaggag guaaaacaca ugaccugcgu uuagguugaa uu          52

<210> SEQ ID NO 19
<211> LENGTH: 49
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 19
ggguuaacuu aguaaggag guaaaacaca ugaccugcug cguugaauu             49

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 20

Met Thr Cys Val
  1

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 21

Met Thr Cys Cys Val
  1               5

<210> SEQ ID NO 22
<211> LENGTH: 76
<212> TYPE: RNA
<213> ORGANISM: Escherichia coli

<400> SEQUENCE: 22
uccucuguag uucagucggu agaacggcgg acuguuaauc cguaugucac ugguucgagu    60
ccagucagag gagcca                                                    76

<210> SEQ ID NO 23
<211> LENGTH: 74
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 23 ggucuguag uucagucggu agaacggcgg acuguuaauc cguaugucac ugguucgagu    60
ccagucagac ccgc                                                      74

<210> SEQ ID NO 24
<211> LENGTH: 76
<212> TYPE: RNA
<213> ORGANISM: Artificial Sequence

```
<220> FEATURE:
<223> OTHER INFORMATION: Description of Artificial Sequence:FROM
      SYNTHETIC RNA

<400> SEQUENCE: 24
gggucuguag uucagucggu agaacggcgg acuguuaauc cguaugucac ugguucgagu      60
ccagucagac ccgcca                                                     76

<210> SEQ ID NO 25
<211> LENGTH: 76
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 25
gggucuguag uucagucggu agaacggcgg acugguaauc cguaugucac ugguucgagu      60
ccagucagac ccgcca                                                     76

<210> SEQ ID NO 26
<211> LENGTH: 76
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 26
gggucuguag uucagucggu agaacggcgg acugcuaauc cguaugucac ugguucgagu      60
ccagucagac ccgcca                                                     76

<210> SEQ ID NO 27
<211> LENGTH: 76
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 27
gggucuguag uucagucggu agaacggcgg acugacaauc cguaugucac ugguucgagu      60
ccagucagac ccgcca                                                     76

<210> SEQ ID NO 28
<211> LENGTH: 74
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 28
gggucuguag uucagucggu agaacggcgg acugguaauc cguaugucac ugguucgagu      60
ccagucagac ccgc                                                       74

<210> SEQ ID NO 29
<211> LENGTH: 74
<212> TYPE: RNA
<213> ORGANISM: Artificial Sequence
<220> FEATURE:
<223> OTHER INFORMATION: Description of Artificial Sequence:FROM
      SYNTHETIC RNA
```

```
<400> SEQUENCE: 29 ggucucuguag uucagucggu agaacggcgg acugcuaauc cguaugucac ugguucgagu      60
ccagucagac ccgc                                                        74

<210> SEQ ID NO 30
<211> LENGTH: 74
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 30 ggucucuguag uucagucggu agaacggcgg acugacaauc cguaugucac ugguucgagu      60
ccagucagac ccgc                                                        74

<210> SEQ ID NO 31
<211> LENGTH: 46
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 31
ggguuaacuu uaguaaggag guaaaacaca ugaccaacgu ugaauu                      46

<210> SEQ ID NO 32
<211> LENGTH: 49
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 32
ggguuaacuu uaguaaggag guaaaacaca ugaccaacaa cguugaauu                   49

<210> SEQ ID NO 33
<211> LENGTH: 2
<212> TYPE: DNA
<213> ORGANISM: Artificial Sequence
<220> FEATURE:
<223> OTHER INFORMATION: Description of Artificial Sequence:FROM
      SYNTHETIC DNA

<400> SEQUENCE: 33 ca                                                                      2

<210> SEQ ID NO 34
<211> LENGTH: 96
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 34
ggguuaacuu uaguaaggag guaaaacaca ugguuaccgu gacuguaguu gugacuaccg       60
uaaccguagu gacuguugua acuaccguug ugaauu                                 96

<210> SEQ ID NO 35
<211> LENGTH: 21
<212> TYPE: PRT
```

```
<213> ORGANISM: Artificial Sequence
<220> FEATURE:
<223> OTHER INFORMATION: Description of Artificial Sequence:FROM
      SYNTHETIC DNA

<400> SEQUENCE: 35

Met Val Thr Val Thr Val Val Thr Val Thr Val Val Thr Val
  1               5                  10                  15

Val Thr Thr Val Val
             20

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 36

Met Val Thr Val Thr Val Val Val Thr Thr Val Thr Val
  1               5                  10

<210> SEQ ID NO 37
<211> LENGTH: 41
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 37

Met Val Thr Val Thr Val Val Val Thr Thr Val Thr Val Val Thr Val
  1               5                  10                  15

Val Thr Thr Val Val Val Thr Val Thr Val Val Val Thr Thr Val Thr
             20                  25                  30

Val Val Thr Val Val Thr Thr Val Val
         35                  40

<210> SEQ ID NO 38
<211> LENGTH: 53
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 38

Met Val Thr Val Thr Val Val Val Thr Thr Val Thr Val Val Thr Val
  1               5                  10                  15

Val Thr Thr Val Val Val Thr Val Thr Val Val Val Thr Thr Val Thr
             20                  25                  30

Val Val Thr Val Val Thr Thr Val Val Thr Val Thr Val Val Val
         35                  40                  45

Thr Thr Val Thr Val
         50

<210> SEQ ID NO 39
<211> LENGTH: 61
<212> TYPE: PRT
<213> ORGANISM: Artificial Sequence
<220> FEATURE:
<223> OTHER INFORMATION: Description of Artificial Sequence:FROM
      SYNTHETIC DNA
```

-continued

<400> SEQUENCE: 39

Met Val Thr Val Thr Val Val Thr Thr Val Thr Val Val Thr Val
1               5                   10                  15

Val Thr Thr Val Val Val Thr Val Thr Val Val Thr Thr Val Thr
                20                  25                  30

Val Val Thr Val Val Thr Thr Val Val Val Thr Val Thr Val Val
            35                  40                  45

Thr Thr Val Thr Val Val Thr Val Val Thr Thr Val
    50                  55                  60

<210> SEQ ID NO 40
<211> LENGTH: 101
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 40

Met Val Thr Val Thr Val Val Thr Thr Val Thr Val Val Thr Val
1               5                   10                  15

Val Thr Thr Val Val Val Thr Val Thr Val Val Thr Thr Val Thr
                20                  25                  30

Val Val Thr Val Val Thr Thr Val Val Val Thr Val Thr Val Val
            35                  40                  45

Thr Thr Val Thr Val Val Thr Val Val Thr Thr Val Thr Val Val
    50                  55                  60

Thr Val Val Thr Thr Val Thr Val Val Thr Val Val Thr Thr Val
65                  70                  75                  80

Val Val Thr Val Thr Val Val Thr Val Thr Val Val Val Thr Val
                85                  90                  95

Val Thr Thr Val Val
            100

<210> SEQ ID NO 41
<211> LENGTH: 29
<212> TYPE: DNA
<213> ORGANISM: Artificial Sequence
<220> FEATURE:
<223> OTHER INFORMATION: Description of Artificial Sequence:FROM
      SYNTHETIC DNA

<400> SEQUENCE: 41
aaaaaaaaaa aaaaaaaaaa aaaaaaacc                                29

<210> SEQ ID NO 42
<211> LENGTH: 3
<212> TYPE: RNA
<213> ORGANISM: Artificial Sequence
<220> FEATURE:
<223> OTHER INFORMATION: Description of Artificial Sequence:SYNTHETIC
      RNA

<400> SEQUENCE: 42 aug                                                             3

<210> SEQ ID NO 43
<211> LENGTH: 57
<212> TYPE: RNA
<213> ORGANISM: Artificial Sequence
<220> FEATURE:
<223> OTHER INFORMATION: Description of Artificial Sequence:FROM -continued

```
SYNTHETIC RNA

<400> SEQUENCE: 43
ggguuaacuu uaguaaggag guaaaaaaaa ugaccaccac caccaccguu gaauucc      57

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence:FROM
      SYNTHETIC DNA

<400> SEQUENCE: 44

Met Thr Thr Thr Thr Thr Val
  1               5

<210> SEQ ID NO 45
<211> LENGTH: 49
<212> TYPE: RNA
<213> ORGANISM: Artificial Sequence
<220> FEATURE:
<223> OTHER INFORMATION: Description of Artificial Sequence:FROM
      SYNTHETIC RNA

<400> SEQUENCE: 45
ggguuaacuu uaguaaggag guaaaacaca ugaccaacag cguugaauu              49

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:FROM
      SYNTHETIC DNA

<400> SEQUENCE: 46
tttttttttt aattcaac                                                18

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence:FROM
      SYNTHETIC DNA

<400> SEQUENCE: 47
tatacatatg caccaccacc accaccac                                     28

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:FROM
      SYNTHETIC DNA

<400> SEQUENCE: 48
taagaattcg agctccgtcg aagatcc                                      27
```

What is claimed is:

1. A reconstituted cell-free translation system, which lacks more than one active wild-type elongator amino acyl tRNA species, for generating a peptidomimetic product comprising:

(a) purified translation factors; and
(b) more than one elongator tRNA species which (i) is charged with a non-naturally occurring amino acid or amino acid analog, and (ii) recognizes a trinucleotide sense codon, wherein the elongator tRNA species charged with a non-naturally occurring amino acid or amino acid analog replaces the wild-type elongator amino acyl tRNA species, wherein the cell-free translation system translates exogenously added mRNA species with highly selective incorporation at each of said trinucleotide sense codons to form the peptidomimetic product, wherein the peptidomimetic product comprises said non-naturally occurring amino acids or amino acid analogs, and wherein the system lacks the ability to synthesize the wild-type amino acyl tRNA species.

2. The translation system of claim 1 for generating a peptidomimetic product, which system is substantially free of the translation factors EF-P, W, W2 and rescue.

3. The translation system of claim 1 for generating a peptidomimetic product, which system is substantially free of a translation factor selected from the group consisting of EF-P, W, W2 and rescue.

4. The translation system of claim 1, wherein the amino acid analog is selected from the group consisting of β-cyanoalanine, canavanine, djenkolic acid, norleucine, 3-phosphoserine, homoserine, dihydroxyphenylalanine, 5-hydroxytryptophan, 1-methylhistidine, 3-methylhistidine, allyl glycine (or its alkyne counterpart), O-methyl-serine, biotinyl-lysine, biotinyl-cysteine (or other biotin-labelled amino acids) cyclohexylalanine, homoglutamate, D-alanine (or other D-amino acids), N-methyl glycine (or other N-methyl amino acids) and epsilon-N-methyl-lysine.

5. The translation system of claim 1, further comprising more than one exogenously added mRNA species encoding different peptidomimetic products.

6. The translation system of claim 5, comprising four or more tRNA species charged with a non-naturally occurring amino acid or amino acid analog.

7. The translation system of claim 1, wherein the translation factors are bacterial translation factors.

8. The translation system of claim 1, comprising four or more tRNA species charged with a non-naturally occurring amino acid or amino acid analog.

9. The translation system of claim 1, wherein highly selective incorporation at each codon comprises at least 90% selective incorporation.

10. The translation system of claim 1, wherein highly selective incorporation at each codon comprises at least 95% selective incorporation.

11. The translation system of claim 1, wherein highly selective incorporation at each codon comprises at least 98% selective incorporation.

12. The translation system of claim 1, wherein the peptidomimetic product comprises more than two non-naturally occurring amino acids or amino acid analogs.

13. The translation system of claim 1, wherein the amino acyl tRNA species is synthesized from a tRNA species lacking a terminal CA dinucleotide.

14. The translation system of claim 1, wherein the amino acyl tRNA species is synthesized from a tRNA species that is synthesized in vitro.

15. The translation system of claim 1, wherein the peptidomimetic product comprises a non-natural backbone.

16. The translation system of claim 1, wherein the non-naturally occurring amino acid or the amino acid analog is synthesized by chemical modification of a natural amino acyl tRNA.

17. A method for generating a peptidomimetic product comprising:

(a) contacting the translation system of claim 1 with one or more exogenous mRNA species encoding peptidomimetic products; and (b) allowing sufficient time for the exogenous mRNA species to be translated, thereby generating the peptidomimetic product.

18. The method of claim 17, wherein the method is carried out on a library of at least 100 different mRNA species.

19. The method of claim 18, wherein the peptidomimetic products are identified or isolated from the translation system based on catalytic or binding activity.

20. The method of claim 17, wherein the mRNA species are generated by in vitro transcription in the translation system.

21. The method of claim 17, wherein the peptidomimetic products are formed as a covalent adduct of the exogenous mRNA by which said products are encoded.

22. The method of claim 17, wherein the translation system is contacted with a library of different exogenously mRNA species to generate a variegated population of peptidomimetics products of at least $10^3$ different sequences.

23. The method of claim 22, wherein at least $10^8$ different sequences are produced.

24. The method of claim 17, comprising contacting the translation system with more than one exogenous mRNA species.

25. The method of claim 17, wherein the peptidomimetic products are identified, isolated, or both.

26. A cell-free translation system comprising purified translation factors and tRNA species that translates exogenously added mRNA species to form a peptidomimetic product, which system (a) lacks more than one active wild-type elongator amino acyl tRNA species and lacks the ability to synthesize said wild-type amino acyl tRNA species, and (b) comprises more than one exogenous elongator amino acyl tRNA species charged with a non-natural amino acid species or amino acid analog, the exogenous elongator amino acyl tRNA species replacing said wild-type elongator amino acyl tRNA species.

27. The translation system of claim 26, wherein the translation factors are bacterial translation factors.

28. The translation system of claim 26 comprising a plurality of different mRNA species.

29. The translation system of claim 28, wherein the peptidomimetic product comprises five non-naturally occurring amino acids or amino acid analogs.

30. The translation system of claim 26, wherein said exogenous elongator amino acyl tRNA species is specific for one of the 61 sense codons.

31. The translation system of claim 26, wherein said exogenous elongator amino acyl tRNA species is specific for one of the three termination codons.

32. The cell-free translation system of claim 26, wherein the translation system translates exogenously added mRNA species with highly selective incorporation at each codon to form a peptidomimetic product.

33. A method for generating a peptidomimetic comprising:

(a) contacting the translation system of claim 26 with one or more exogenous mRNA species encoding peptidomimetic products; and (b) allowing sufficient time for the exogenous mRNA species to be translated, thereby generating the peptidomimetic product.

34. The method of claim 33, comprising contacting the translation system with more than one exogenous mRNA species.

35. The method of claim 33, wherein the peptidomimetic products are identified, isolated, or both.

36. The method of claim 33, wherein the exogenous mRNA species is generated by in vitro transcription in the translation system.

37. A cell-free translation system comprising purified translation factors and tRNA species that translates exogenously added mRNAs to form a peptidomimetic product, which system
  (a) lacks one or more active wild-type amino acyl tRNA species and lacks the ability to synthesize said wild-type amino acyl tRNA species,
  (b) comprises at least one exogenous amino acyl tRNA species charged with a non-natural amino acid species or amino acid analog, the exogenous amino acyl tRNA species replacing said active wild-type amino acyl tRNA species, and
  (c) comprises a plurality of different mRNA species encoding a plurality of peptidomimetic products.

38. A kit for translating exogenously added mRNA to form a peptidomimetic product, the kit comprising:
  (a) a reconstituted cell-free translation system that lacks more than one active wild-type elongator amino acyl tRNA species, comprising: purified translation factors and more than one elongator tRNA species charged with a non-naturally occurring amino acid or amino acid analog that translates exogenously added mRNA species with highly selective incorporation at each codon to form a peptidomimetic product, wherein the elongator tRNA species charged with a non-naturally occurring amino acid or amino acid analog replaces the wild-type elongator amino acyl tRNA species, and wherein the system lacks the ability to synthesize the wild-type amino acyl tRNA species; and
  (b) instructions associated therewith for using the kit for translating exogenously added mRNA to form a peptidomimetic product.

39. The kit of claim 38, wherein the kit translates exogenously added mRNA species with highly selective incorporation at each codon to form a peptidomimetic product.

40. A kit for translating exogenously added mRNA to form a peptidomimetic product, the kit comprising:
  (a) a cell-free translation system comprising purified translation factors and tRNA species that translates exogenously added mRNA species to form a peptidomimetic product, which system
    (i) lacks more than one active wild-type elongator amino acyl tRNA species and lacks the ability to synthesize said wild-type amino acyl tRNA species,
    (ii) comprises more than one exogenous elongator amino acyl tRNA species charged with a non-natural amino acid species or amino acid analog, the exogenous elongator amino acid acyl tRNA species replacing said wild-type elongator amino acyl tRNA species; and
  (b) instructions associated therewith for using the kit for translating exogenously added mRNA to form a peptidomimetic product.

* * * * *